US008865149B2

(12) United States Patent
McManus et al.

(10) Patent No.: US 8,865,149 B2
(45) Date of Patent: Oct. 21, 2014

(54) POLYMERIC REAGENTS COMPRISING A KETONE OR A RELATED FUNCTIONAL GROUP

(75) Inventors: Samuel P. McManus, Huntsville, AL (US); Antoni Kozlowski, Huntsvill, AL (US); Xiaoming Shen, Madison, AL (US); Daniel C. Cook, Harvest, AL (US)

(73) Assignee: Nektar Therapeutics, San Francisco, CA (US)

( * ) Notice: Subject to any disclaimer, the term of this patent is extended or adjusted under 35 U.S.C. 154(b) by 1902 days.

(21) Appl. No.: 11/714,322

(22) Filed: Mar. 6, 2007

(65) Prior Publication Data

US 2007/0166277 A1 Jul. 19, 2007

Related U.S. Application Data

(63) Continuation of application No. 10/751,009, filed on Dec. 31, 2003, now Pat. No. 7,208,145.

(60) Provisional application No. 60/437,325, filed on Dec. 31, 2002.

(51) Int. Cl.
*A61K 31/74* (2006.01)
*C08G 65/331* (2006.01)
*A61K 47/48* (2006.01)
*C08G 65/329* (2006.01)
*C08G 65/334* (2006.01)

(52) U.S. Cl.
CPC ........ *A61K 47/48215* (2013.01); *C08G 65/331* (2013.01); *C08G 65/329* (2013.01); *C08G 65/3344* (2013.01); *C08L 2203/02* (2013.01)
USPC .................. 424/78.27; 424/78.26; 424/78.37; 424/78.08

(58) Field of Classification Search
USPC ...................................................... 424/78.27
See application file for complete search history.

(56) References Cited

U.S. PATENT DOCUMENTS

| 3,551,384 | A |   | 12/1970 | Zeh |
| 3,668,183 | A |   | 6/1972 | Hoy et al. |
| 3,779,986 | A |   | 12/1973 | Smith et al. |
| 4,980,514 | A |   | 12/1990 | Sanderson et al. |
| 4,992,204 | A |   | 2/1991 | Kluger et al. |
| 5,002,998 | A |   | 3/1991 | Carey et al. |
| 5,045,396 | A |   | 9/1991 | Lin et al. |
| 5,138,095 | A |   | 8/1992 | Speranza et al. |
| 5,149,806 | A |   | 9/1992 | Moren et al. |
| 5,151,470 | A |   | 9/1992 | Sanders et al. |
| 5,382,657 | A | * | 1/1995 | Karasiewicz et al. ......... 530/351 |
| 5,580,923 | A |   | 12/1996 | Yeung et al. |
| 5,674,531 | A |   | 10/1997 | Ahlers et al. |
| 5,723,289 | A |   | 3/1998 | Eaton et al. |
| 5,733,968 | A |   | 3/1998 | Moszner et al. |
| 5,858,660 | A |   | 1/1999 | Eaton et al. |
| 5,932,462 | A |   | 8/1999 | Harris et al. |
| 5,932,641 | A |   | 8/1999 | Blanchard et al. |
| 6,048,698 | A |   | 4/2000 | Eaton et al. |
| 6,102,997 | A |   | 8/2000 | Helling et al. |
| 6,258,774 | B1 |   | 7/2001 | Stein et al. |
| 6,348,558 | B1 |   | 2/2002 | Harris et al. |
| 6,362,254 | B2 |   | 3/2002 | Harris et al. |
| 6,395,266 | B1 |   | 5/2002 | Martinez et al. |
| 6,448,369 | B1 |   | 9/2002 | Bentley et al. |
| 6,642,035 | B2 |   | 11/2003 | Janda et al. |
| 7,208,145 | B2 |   | 4/2007 | McManus et al. |
| 2001/0011115 | A1 | * | 8/2001 | Harris et al. .................... 525/56 |
| 2003/0157582 | A1 |   | 8/2003 | Roisin et al. |

FOREIGN PATENT DOCUMENTS

| CA | 1148166 | 6/1983 |
| DE | 3334209 | 4/1985 |
| DE | 10126158 | 12/2002 |
| EP | 0361704 | 4/1990 |
| EP | 0400486 | 12/1990 |
| EP | 0420232 | 4/1991 |
| EP | 0457128 | 11/1991 |
| EP | 0605963 | 7/1994 |
| EP | 0634393 | 1/1995 |
| EP | 1174436 | 1/2002 |
| EP | 1310533 | 5/2003 |
| JP | 60212435 | 10/1985 |
| JP | 01255620 | 10/1989 |
| JP | 02283659 | 11/1990 |
| JP | 69737 | 1/1994 |
| JP | 649471 | 2/1994 |
| JP | 06324421 | 11/1994 |
| JP | 762279 | 3/1995 |
| JP | 762594 | 3/1995 |
| JP | 07159917 | 6/1995 |
| JP | 2000129568 | 5/2000 |

(Continued)

OTHER PUBLICATIONS

European Search Report and Examination Report, (Aug. 27, 2007).
Australian Examination Report corresponding to Australian Patent Application No. 2003303519 dated Jun. 5, 2008.
Indian Examination Report corresponding to Indian Patent Application No. 2863/DELNP/2005 dated Oct. 5, 2007.
Japanese Office Action corresponding to Japanese Patent Application No. 2004-564925 mailing date Aug. 11, 2009.
Mexican Office Action corresponding to Mexican Patent Application No. PA/a/2005/007165 Dated Apr. 16, 2009.
PCT International Search Report corresponding to PCT International Application No. PCT/U52003/041743 date of mailing Nov. 18, 2004.
PCT Written Opinion corresponding to PCT International Application No. PCT/US2003/041743 date of mailing Dec. 9, 2004.

(Continued)

*Primary Examiner* — James Rogers
(74) *Attorney, Agent, or Firm* — Mark A. Wilson; Timothy A. Marquart

(57) ABSTRACT

Polymeric reagents comprising a polymer attached, either directly or through one or more atoms, to a ketone or a related functional group such as ketone hydrate, thione, monothiohydrate, dithiohydrate, hemiketal, monothiohemiketal, dithiohemiketal, ketal, or dithioketal are provided. The polymeric reagents are useful for, among other things, forming polymer-active agent conjugates. Related methods, compositions, preparations, and so forth are also provided.

7 Claims, 3 Drawing Sheets

(56) References Cited

FOREIGN PATENT DOCUMENTS

| | | |
|---|---|---|
| JP | 2001255620 | 9/2001 |
| JP | 2002234940 | 8/2002 |
| WO | 90/00049 | 1/1990 |
| WO | 95/21631 | 8/1995 |
| WO | 96/33156 | 10/1996 |
| WO | 96/33157 | 10/1996 |
| WO | 97/49664 | 12/1997 |
| WO | 98/53857 | 12/1998 |
| WO | 00/17398 | 3/2000 |
| WO | 00/44808 | 8/2000 |
| WO | 01/04179 | 1/2001 |
| WO | 01/04183 | 1/2001 |
| WO | 01/92584 | 12/2001 |
| WO | WO 0192584 A1 * | 12/2001 |
| WO | 03/004471 | 1/2003 |
| WO | 03/008646 | 1/2003 |
| WO | 03/034995 | 5/2003 |
| WO | 2004/060406 | 7/2004 |

OTHER PUBLICATIONS

PCT International Preliminary Examination Report corresponding to PCT International Application No. PCT/US2003/041743 date of mailing Apr. 8, 2005.

Cordova, et al., "A Highly Chemo- and Stereoselective Synthesis of β-Keto Esters via a Polymer-Supported Lipase Catalyzed Transesterfication", J. Org. Chem. (2001), 66:1906-1909.

Haag, et al., "New Polyethylene Glycol Polymers as Ketal Protecting Groups—A Polymer Supported Approach to Symmetrically Substituted Spiroketals", Synthetic Communications (2001), 31(19):2965-2977.

Hai, et al., "Polymerization to Diaspirin Cross-Linked Hemoglobin (DCLHb) with Water-Soluble, Nonimmunogenic Polyamide Cross-Linking Agents", Bioconjugate Chem. (1999), 10:1013-1020.

Herman, et al., "Poly(Ethylene Glycol) with Reactive Endgroups: I. Modification of Proteins", J. of Bioactive and Compatible Polymers (Apr. 1995), 10:145-187.

Huang, et al., "The Synthesis of Polyethylene Glycol (PEG) with Different Functional Groups at Each End. II. Synthesis of a Series of Monosubstituted PEG via Polyvinyl Alcohol (PVA) as Support", J. of Applied Polymer Sci. (1993), 47:1503-1511.

Mohseni, et al., "Condution and electrooptical properties of vanadium-containing polymer electrolyte networks from sol-gel methods with modified poly(ethylene glycol)s and poly(tetramethylene oxide)", J. Mater. Chem. (1999) 9:1363-1367.

Moszner, et al., "Reaction behaviour of monomeric β-ketoesters", Polymer Bulletin (1994), 32:411-417.

Naka, et al., "Synthesis of a star-shaped polymer having tris (β-diketonato)chromium(III) at the center core", Polymer Bulletin (1998), 41:263-266.

NEKTAR™—Transforming Therapeutics, Nektar Molecule Engineering: Polyethylene Glycol and Derivatives for Advanced PEGylation, pp. 1-20, (Catalog—2003).

NOF Corporation, "PEG Derivatives, Phospholipid and Drug Delivery Materials for Pharmaceuticals", pp. 1-46, (Catalogue 2003-1$^{st}$).

NOF Corporation, "PEG Derivatives, Phospholipid and Drug Delivery Materials for Pharmaceuticals", pp. 1-50, (Catalogue 2003-2$^{nd}$).

Pande, et al., "Camphorquinone-10-sulfonic acid and derivatives: Convenient reagents for reversible modification of arginine residues", Proc. Natl. Acad. Sci. USA, 77(2);895-899, Feb. 1980, Biochemistry.

Parr, et al., "Factors influencing the retention and chemical stability of poly(ethylene glycol)-lipid conjugates incorporated into large unilamellar vesicles", Biophysica Acta 1195 (1994), pp. 21-30.

Seliger, et al., "Two-carrier liquid-phase synthesis of main-chain liquid crystalline oligomers and characterization of the products", Fresenius J. Anal. Chem. (1995), 351:260-270.

Shearwater Polymers, Inc., p. 2-49, (Catalog—Mar. 1995).

Shearwater Polymers, Inc., Polyethylene Glycol and Derivatives, pp. 1-53, (Catalog—Jul. 1997).

Shearwater Polymers, Inc., Polyethylene Glycol and Derivatives: Functionalized Biocompatible Polymers for Research and Pharmaceuticals, pp. 1-50, (Catalog—2000).

Shearwater Corporation, Polyethylene Glycol and Derivatives for Biomedical Applications, pp. 1-17, (Catalog—2001).

Chinese First Office Action corresponding to Chinese Patent Application No. 200380109450.4 dated Mar. 2, 2007.

Chinese Second Office Action corresponding to Chinese Patent Application No. 200380109450.4 dated Oct. 24, 2008.

Chinese Third Office Action corresponding to Chinese Patent Application No. 200380109450.4 dated Oct. 10, 2009.

European Communication corresponding to European Patent Application No. 03815012.4 dated Nov. 21, 2006.

PCT Invitation to Pay Additional Fees/Partial International Search corresponding to PCT Application No. PCT/US2003/041743 dated Aug. 10, 2003.

Office Action corresponding to Canadian Patent Application No. 2,509,248 dated Aug. 2, 2010.

Office Action corresponding to Canadian Patent Application No. 2,509,248 dated Apr. 6, 2011.

Notification of the Fourth Office Action corresponding to Chinese Patent Application No. 200380109450.4 dated Aug. 5, 2011.

Communication corresponding to European Patent Application No. 03 815 012.4-2404 dated Nov. 26, 2012.

Communication corresponding to European Patent Application No. 03 815 012.4-1408 dated Apr. 26, 2013.

Notice of Reasons for Rejection mailed Jun. 15, 2010 corresponding to Japanese Patent Application No. 2004-564925.

Notice of Reasons for Rejection mailed Nov. 1, 2011 corresponding to Japanese Patent Application No. 2004-564925.

Notice of Grounds for Rejection issued Nov. 5, 2010 corresponding to Korean Patent Application No. 2005-7012459.

Summons to Attend Oral Proceedings pursuant to Rule 115(1) EPC dated Dec. 3, 2013 corresponding to European Patent Application No. 03815012.4-1408 / 1581260.

* cited by examiner

POLYMERIC REAGENTS COMPRISING A KETONE OR A RELATED FUNCTIONAL GROUP

CROSS REFERENCE TO RELATED APPLICATIONS

This application is a continuation of U.S. patent application Ser. No. 10/751,009, filed Dec. 31, 2003, now U.S. Pat. No. 7,208,145, which claims the benefit of priority to U.S. Provisional Patent Application Ser. No. 60/437,325, filed Dec. 31, 2002, each of which is incorporated herein by reference.

FIELD OF THE INVENTION

The present invention relates generally to novel polymeric reagents comprising a ketone or a related functional group such as, for example, a ketone hydrate, thione, monothiohydrate, dithiohydrate, hemiketal, monothiohemiketal, dithiohemiketal, ketal, and dithioketal. In addition, the invention relates to conjugates formed from the attachment of a polymeric reagent described herein to another substance, such as an active agent. Furthermore, the invention relates to methods for synthesizing polymeric reagents, methods, for conjugating a polymeric reagent to another substance, compositions comprising the polymeric reagents, and the like.

BACKGROUND OF THE INVENTION

Scientists and clinicians face a number of challenges in their attempts to develop active agents into forms suited for delivery to a patient. Active agents that are polypeptides, for example, are often delivered by injection rather than orally. In this way, the polypeptide is introduced into the systemic circulation without exposure to the proteolytic environment of the stomach. Injection of polypeptides, however, has several drawbacks. For example, many polypeptides have a relatively short half-life, thereby necessitating the need for repeated injections, which are often inconvenient and painful. Moreover, some polypeptides may elicit one or more immune responses with the consequence that the patient's immune system may be activated to degrade or inactivate the polypeptide. Thus, the delivery of polypeptides and other active agents is often problematic even when these agents are administered by injection.

Some success in addressing the problems of delivering active agents via injection has been achieved. For example, conjugating the active agent to a water-soluble polymer has resulted in polymer-active agent conjugates having reduced immunogenicity and antigenicity. In addition, these conjugates often have greatly increased half-lives compared to their unconjugated counterparts as a result of decreased clearance through the kidney and/or decreased enzymatic degradation in vivo. As a result of having a greater half-life, the conjugate requires less frequent dosing, which in turn reduces the overall number of painful injections and inconvenient visits to a health care professional. Moreover, active agents that are only marginally soluble often demonstrate a significant increase in water solubility when conjugated to a water-soluble polymer.

Due to its documented safety as well as its approval by the FDA for both topical and internal use, poly(ethylene glycol) has been conjugated to active agents. When an active agent is conjugated to a polymer of poly(ethylene glycol) or "PEG", the conjugated active agent is conventionally referred to as having been "PEGylated." The commercial success of PEGylated active agents attests to their value. Exemplary commercially available PEGylated polypeptides include PEGASYS® PEGylated interferon alpha-2a (Hoffmann-La Roche, Nutley, N.J.), PEG-INTRON® PEGylated interferon alpha-2b (Schering Corp., Kennilworth, N.J.), SOMAVERT® PEGylated human growth hormone receptor antagonist, and NEULASTA® PEG-filgrastim (Amgen Inc., Thousand Oaks, Calif.). PEGylated small molecules such as distearoylphosphatidylethanolamine (Zalipsky (1993) *Bioconjug. Chem.* 4(4):296-299) and fluorouracil (Ouchi et al. (1992) *Drug Des. Discov.* 9(1):93-105) have also been prepared.

Despite these successes, conjugation of a polymer to an active agent remains challenging. In particular, the conjugation reaction is relatively imprecise in that a relatively disperse mixture of products results. For example, the conjugation reaction often results in a mixture of singly substituted, disubstituted, and polysubstituted conjugate forms. Moreover, the possible number of different conjugate forms increases inasmuch as different attachment sites of an active agent can result in different arrangements of attachments. For example, a singly substituted active agent having three different sites for attachment to a polymer can have three different forms: each form having the single polymer attached to one of the three different attachment sites. Recognizing that each conjugate form can have a unique pharmacodynamic and pharmacokinetic profile only serves to underscore the complexity associated with providing polymer-active agent conjugates that are suited for use as therapeutic agents. Thus, there is a desire to provide polymeric reagents that are "site-directed" so that the desired conjugates can be more predictably formed.

Some degree of selectivity in the conjugation reaction is achieved based on the presence of the particular functional group present on the polymeric reagent. For example, poly (ethylene glycol) derivatives bearing an aldehyde derivative (shown below) undergo reductive amination reactions with primary amines of, for example, a polypeptide.

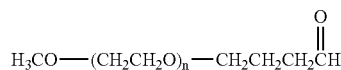

a poly(ethylene glycol) derivative bearing an aldehyde derivative wherein (n) represents the number of repeating ethylene oxide units As a consequence, a degree of selectivity is achieved in that conjugation typically occurs only between the relatively reactive and readily accessible primary amine groups of the polypeptide and the aldehyde of the polymeric reagent. For polypeptides having many relatively reactive primary amine groups (e.g., a polypeptide having many primary amine-containing lysine residues), however, the conjugation reaction nonetheless results in a relatively polydisperse mixture of conjugate forms.

In order to provide an alternative to polymeric reagents-bearing aldehyde derivatives, the present invention provides polymeric reagents comprising a ketone or a related functional group (e.g., a ketone hydrate, thione, monothiohydrate, dithiohydrate, hemiketal, monothiohemiketal, dithiohemiketal, ketal, or dithioketal).

Others have described polymers comprising a ketone or a related functional group for use in variety of contexts. Typically, however, the described polymers are unsuited for conjugation.

For example, WO 96/33156 describes poly(alkylene glycol) derivatives of benzophenone and related aromatic moieties. The derivatives are described as being useful as photoinitiators. Aromatic rings, however, are preferably absent in polymeric reagents useful for conjugation to an active agent because the hydrophobic nature of aromatic moieties undesirably decreases aqueous solubility. In addition, aromatic rings contained in a conjugate may be metabolized in vivo into arene oxide intermediates, which can covalently bind with nucleophilic groups present on proteins, DNA and RNA, thereby leading to cellular toxicity. See Daly et al. (1979) *Experientia* 28(10):1129-1149.

U.S. Pat. No. 5,149,806 describes a carbon acid useful as a Michael donor. One of the described structures is provided below:

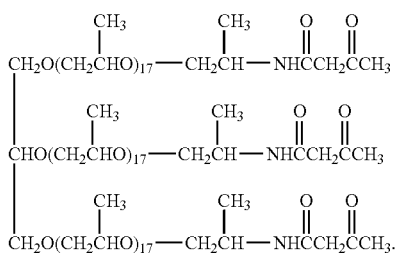

Even if structures like these could be used for conjugation reactions, the propylene oxide polymers are not suitably water-soluble to provide a conjugate acceptable for in vivo administration.

Other previously described polymeric reagents suffer from similar deficiencies.

Thus, there remains a need in the art to provide polymeric reagents that are useful for providing, among other things, conjugates with other substances. The present invention addresses this and other needs in the art by providing, inter alia, novel polymeric reagents comprising a ketone or a related functional group (e.g., a ketone hydrate, thione, monothiohydrate, dithiohydrate, hemiketal, monothiohemiketal, dithiohemiketal, ketal, or dithioketal).

SUMMARY OF THE INVENTION

Accordingly, it is a primary object of this invention to provide a polymeric reagent comprising a functional group and a water-soluble polymer segment, wherein the functional group is attached to the water-soluble polymer segment through one or more atoms, wherein the functional group is selected from the group consisting of ketone, ketone hydrate, thione, monothiohydrate, dithiohydrate, hemiketal, monothiohemiketal, dithiohemiketal, ketal, and dithioketal.

It is another object of the invention to provide such a polymeric reagent wherein the water-soluble polymer segment has a molecular weight of greater than 2,200.

It is an additional object of the invention to provide such a polymeric reagent wherein the functional group is selected from the group consisting of ketone, ketone hydrate, hemiketal, and ketal.

It is still another object of the invention to provide such a polymeric reagent wherein the water-soluble polymer segment is a poly(ethylene glycol).

It is a further object of the invention to provide methods for preparing the polymeric reagent described herein.

It is still a further object of the invention to provide a conjugate of a substance and a polymeric reagent as described herein.

It is another object of the invention to provide such a conjugate wherein the substance is an active agent.

It is yet another object of the invention to provide a pharmaceutical composition comprising a polymer-active agent conjugate as described herein.

It is an additional object of the invention to provide a method for administering the polymer conjugates described herein.

Additional objects, advantages and novel features of the invention will be set forth in the description that follows, and in part, will become apparent to those skilled in the art upon the following, or may be learned by practice of the invention.

In one embodiment of the invention, then, a polymeric reagent is provided comprising a functional group and a water-soluble polymer segment. The functional group and the water-soluble polymer segment are attached through either a direct covalent bond or through one or more atoms. The functional group is selected from the group consisting of ketone, ketone hydrate, thione, monothiohydrate, dithiohydrate, hemiketal, monothiohemiketal, dithiohemiketal, ketal, and dithioketal. Among other things, the polymeric reagent can form polymer-containing conjugates with another substance (e.g., an active agent).

In another embodiment, a polymeric reagent is provided comprising a functional group and a water-soluble polymer segment having a weight average molecular weight of greater than 2,200, wherein the functional group is attached to the water-soluble polymer segment through either a direct covalent bond or through one or more atoms, and further wherein (a) the functional group is selected from the group consisting of ketone, ketone hydrate, thione, monothiohydrate, dithiohydrate, hemiketal, monothiohemiketal, dithiohemiketal, ketal, and dithioketal, and (b) the polymeric reagent lacks each of the following: an aromatic moiety; a residue of proline; a cyclic dienone, a saturated hydrocarbon chain of 8 carbons or greater; and a —$ONH_2$ group, with the proviso that the polymeric reagent is none of

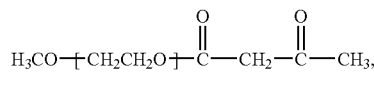

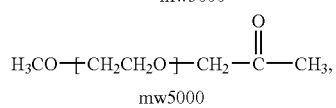

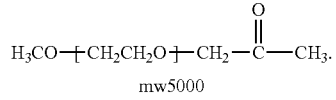

and a ketal derivative of

In another embodiment of the invention, a polymeric reagent is provided comprised of a functional group and a water-soluble polymer segment, wherein the functional group is attached to the water-soluble polymer segment through either a direct covalent bond or through one or more atoms, and further wherein (a) the functional group is selected from the group consisting of thione, monothiohydrate, dithiohydrate, monothiohemiketal, dithiohemiketal, and dithioketal, and (b) the polymeric reagent lacks a saturated hydrocarbon chain of 8 carbons or greater.

In yet another embodiment of the invention, a polymeric reagent is provided comprising a water-soluble polymer segment and a functional group, wherein the functional group is part of a cyclic structure and further wherein the cyclic structure is attached to the water-soluble polymer segment through either a direct covalent bond or through one or more atoms, wherein the functional group is selected from the group consisting of ketone, ketone hydrate, thione, monothiohydrate, dithiohydrate, hemiketal, monothiohemiketal, dithiohemiketal, ketal, and dithioketal, and further wherein the polymeric reagent lacks a cyclic dienone.

As will be explained in greater detail below, the polymeric reagents of the invention encompass many different forms. For example, the polymeric reagent can be monofunctional. Exemplary monofunctional polymeric reagents encompassed by the invention comprise the following structure:

$$R^7-O-POLY^1-(X^1)_a-(EW^1)_b-\left[\begin{array}{c}R^2\\|\\C\\|\\R^3\end{array}\right]_z-FG-R^1 \quad \text{(Formula I)}$$

wherein:
POLY$^1$ is a water-soluble polymer segment having a terminus defined as —O—R$^7$;
(a) is either zero or one;
(b) is either zero or one;
X$^1$, when present, is a spacer moiety;
EW$^1$, when present, is an electron-withdrawing group;
(z) is 0 or a positive integer, e.g., 1, 2, 3, 4, 5, 6, or 7;
each R$^2$, when present, is independently H or a organic radical, for example, H or a nonaromatic-containing organic radical;
each R$^3$, when present, is independently H or a organic radical, for example, H or a nonaromatic-containing organic radical;
R$^7$ is H or a organic radical, for example, H or a nonaromatic-containing organic radical;
FG is a functional group selected from ketone, ketone hydrate, thione, monothiohydrate, dithiohydrate, hemiketal, monothiohemiketal, dithiohemiketal, ketal, and dithioketal; and
R$^1$ is an organic radical, for example, a nonaromatic-containing organic radical;
and further wherein the $$\left[\begin{array}{c}R^2\\|\\C\\|\\R^3\end{array}\right]_z$$

moiety optionally contains one or more double bonds, with the proviso that the polymeric reagent is neither $$HO-(CH_2CHO)_{1-50}\overset{O}{\underset{H}{N}}\underset{}{\overset{O}{\|}}\text{nor}$$

$$H_3CO-(CH_2CH_2O)-CH_2-CH_2-CH_2-\overset{O}{\overset{\|}{C}}-CH_3.$$

mw = 2000

The polymeric reagents of the invention can also be provided in the form of a bifunctional polymeric reagent containing two functional groups (either the same or different). Exemplary bifunctional polymeric reagents encompassed by the invention comprise the following structure:

$$R^6-FG-\left[\begin{array}{c}R^4\\|\\C\\|\\R^5\end{array}\right]_y-(EW^2)_d-(X^2)_c-POLY^1-(X^1)_a-(EW^1)_b-\left[\begin{array}{c}R^2\\|\\C\\|\\R^3\end{array}\right]_z-FG-R^1 \quad \text{(Formula II)}$$

wherein:
POLY$^1$ is a water-soluble polymer segment;
(a) is either zero or one;
(b) is either zero or one;
(c) is either zero or one;
(d) is either zero or one;
X$^1$, when present, is a spacer moiety;
X$^2$, when present, is a spacer moiety;
EW$^1$, when present, is an electron-withdrawing group;
EW$^2$, when present, is an electron-withdrawing group;
(z) is 0 or a positive integer, e.g., 1, 2, 3, 4, 5, 6, or 7;
(y) is 0 or a positive integer, e.g., 1, 2, 3, 4, 5, 6, or 7;
each R$^2$, when present, is independently H or a organic radical, for example, H or a nonaromatic-containing organic radical;
each R$^3$, when present, is independently H or a organic radical, for example, H or a nonaromatic-containing organic radical;
each R$^4$, when present, is independently H or a organic radical, for example, H or a nonaromatic-containing organic radical;
each R$^5$, when present, is independently H or a organic radical, for example, H or a nonaromatic-containing organic radical;
—FG-R$^1$ is either (i) a functional group selected from the group consisting of ketone, ketone hydrate, thione, monothiohydrate, dithiohydrate, hemiketal, monothiohemiketal, dithiohemiketal, ketal, and dithioketal having a terminus defined as R$^1$, wherein R$^1$ is an organic radical, or (ii) a nondienone cyclic structure wherein a functional group selected from the group consisting of ketone, ketone hydrate, thione, monothiohydrate, dithiohydrate, hemiketal, monothiohemiketal, dithiohemiketal, ketal, and dithioketal is part of the cyclic structure; and
-FG-R$^6$ is either (i) a functional group selected from the group consisting of ketone, ketone hydrate, thione, monothiohydrate, dithiohydrate, hemiketal, monothiohemiketal, dithiohemiketal, ketal, and dithioketal having a terminus defined as R$^6$, wherein R$^6$ is an organic radical, or (ii) a nondienone cyclic structure wherein a functional group selected from the group consisting of ketone, ketone hydrate, thione, monothiohydrate, dithiohydrate, hemiketal, monothiohemiketal, dithiohemiketal, ketal, and dithioketal is part of the cyclic structure.
Optionally, each of the $$\left[\begin{array}{c}R^2\\|\\C\\|\\R^3\end{array}\right]_z \quad \text{and} \quad \left[\begin{array}{c}R^4\\|\\C\\|\\R^5\end{array}\right]_z$$

moieties in Formula II contains one or more double bonds.

In still another embodiment, the invention provides polymeric reagents comprising two or more water-soluble polymer segments (either the same or different) and a functional group selected from the group consisting of ketone, ketone hydrate, thione, monothiohydrate, dithiohydrate, hemiketal, monothiohemiketal, dithiohemiketal, ketal, and dithioketal. For example, the polymeric reagent can comprise a first water-soluble polymer segment, a second water-soluble polymer segment, and a functional group selected from the group consisting of ketone, ketone hydrate, thione, monothiohydrate, dithiohydrate, hemiketal, monothiohemiketal, dithiohemiketal, ketal, and dithioketal, wherein each of the first and second water-soluble polymer segments are attached, either through a direct covalent bond or through one or more atoms, to the functional group and further wherein when the functional group is a ketone, ketone hydrate, hemiketal or ketal: (a) the polymeric reagent lacks an aromatic moiety; or (b) each water-soluble polymer segment in the polymeric reagent has a weight average molecule weight of 1000 Daltons or greater. As will be explained in greater detail below, a polymeric reagent as described herein comprising two water-soluble polymer segments can be linear and as taking the form of the letter "V," such that each line segment of the letter comprises one single chain of atoms comprising a water-soluble polymer segment and each chain is attached a carbon atom of the functional group. Nonlinear forms of polymeric reagents comprising two or more water-soluble polymer segments are provided as well.

In another embodiment of the invention, compositions comprising a polymeric reagent are provided. Preferably, the polymeric reagent compositions are free or substantially free of oxidation side products. An exemplary polymeric reagent composition comprises a polymeric reagent comprised of the following structure:

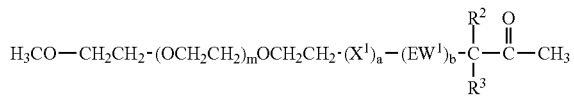

wherein:
(a) is either zero or one;
(b) is either zero or one;
$X^1$, when present, is a spacer moiety;
$EW^1$, when present, is an electron-withdrawing group;
(z) is from 0 or a positive integer, e.g., 1, 2, 3, 4, 5, 6, or 7;
each $R^2$, when present, is independently H or an organic radical, for example, H or a nonaromatic-containing organic radical;
each $R^3$, when present, is independently H or an organic radical, for example, H or a nonaromatic-containing organic radical; and
(m) is a positive integer, e.g., from 11 to about 3000, wherein the composition is substantially free of oxidation side products. Preferably the composition also lacks β-keto esters,

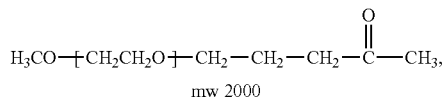

and a ketal derivative of

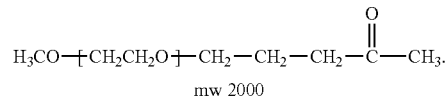

The current invention also provides methods for making polymeric reagents. Thus, in another embodiment of the invention, a method is provided comprised of the steps of (i) providing a precursor molecule comprised of at least one active anionic site suitable for initiating polymerization and a functional group or a protected form thereof, wherein the functional group is selected from the group consisting of ketone, ketone hydrate, thione, monothiohydrate, dithiohydrate, hemiketal, monothiohemiketal, dithiohemiketal, ketal, and dithioketal; (ii) contacting the anionic site of the precursor molecule with a reactive monomer capable of polymerizing, to thereby initiate polymerization of the reactive monomer onto the precursor molecule; (iii) adding additional reactive monomers to the precursor molecule to form one or more polymer chains; (iv) allowing said adding to continue until a desired length of the one or more polymer chains is reached; (v) terminating the reaction, thereby resulting in a polymeric reagent comprised of the functional group or protected form thereof; and (vi) optionally, when the functional group is in the protected form, deprotecting the functional group.

Another method for forming polymeric reagents is provided comprising the steps of (i) providing a precursor molecule comprised of a protected secondary alcohol or thiol and at least one anionic site suitable for initiating polymerization; (ii) contacting the anionic site of the precursor molecule with a reactive monomer capable of polymerizing, to thereby initiate polymerization of the reactive monomer onto the precursor molecule; (iii) adding additional reactive monomers to the precursor molecule to form one or more polymer chains; (iv) allowing said contacting to continue until a desired length of the one or more polymer chains is reached; (v) terminating the reaction, thereby resulting in an intermediate comprised of the protected secondary alcohol or thiol; (vi) deprotecting the protected secondary alcohol or thiol of the intermediate to form an unprotected secondary alcohol or thiol; (vii) oxidizing the unprotected secondary alcohol or thiol to provide a polymeric reagent comprised of a ketone when the precursor molecule comprised a secondary alcohol or a thione when the precursor molecule comprised a secondary thiol; and (viii) optionally further modifying the ketone or thione to result in a functional group selected from the group consisting of ketone, ketone hydrate, thione, monothiohydrate, dithiohydrate, hemiketal, monothiohemiketal, dithiohemiketal, ketal, and dithioketal.

In another embodiment of the invention, a method comprising the steps of (i) providing a precursor molecule comprised of at least one isocyanate moiety and a functional group or a protected form thereof, wherein the functional group is selected from the group consisting of ketone, ketone hydrate, thione, monothiohydrate, dithiohydrate, hemiketal, monothiohemiketal, dithiohemiketal, ketal, and dithioketal; and (ii) contacting, under suitable reaction conditions, the precursor molecule and the water-soluble polymer segment bearing at least one hydroxyl group to thereby form a polymeric reagent comprising the functional group or protected form thereof, and (iii) optionally, when the functional group is in the protected form, deprotecting the functional group.

In another embodiment of the invention for providing polymeric reagent, a method is described comprising the steps of (i) providing a water-soluble polymer segment having at least one available nucleophilic group; (ii) providing a precursor molecule comprised of at least one activating group and a functional group or a protected form thereof, wherein the functional group is selected from the group consisting of ketone, ketone hydrate, thione, monothiohydrate, dithiohydrate, hemiketal, monothiohemiketal, dithiohemiketal, ketal, and dithioketal; (iii) contacting, under suitable reaction conditions, the precursor molecule with the water-soluble polymer segment, thereby forming a polymeric reagent comprising the functional group or protected form thereof; and (iv) optionally, when the functional group is in the protected form, deprotecting the functional group.

In yet another embodiment for making polymeric reagents, a method is provided comprising the steps of: (i) providing a water-soluble polymer segment having at least one available leaving group; (ii) providing a precursor molecule comprised of at least one nucleophilic group and a functional group or a protected form thereof, wherein the functional group is selected from the group consisting of ketone, ketone hydrate, thione, monothiohydrate, dithiohydrate, hemiketal, monothiohemiketal, dithiohemiketal, ketal, and dithioketal; (iii) contacting, under suitable reaction conditions, the precursor molecule with the water-soluble polymer segment, thereby forming a polymeric reagent comprising the functional group or protected form thereof; and (iv) optionally, when the functional group is in the protected form, deprotecting the functional group.

In still another embodiment of the invention, a method for making a polymeric reagent is provided wherein the method comprises the steps of reacting a water-soluble polymer segment having at least one alkoxide ion or thiolate ion with a precursor molecule comprised of at least one leaving group and a functional group or a protected form thereof, wherein the functional group is selected from the group consisting of ketone, ketone hydrate, thione, monothiohydrate, dithiohydrate, hemiketal, monothiohemiketal, dithiohemiketal, ketal, and dithioketal, thereby providing a polymeric reagent.

In still another embodiment of the invention, a method of preparing a conjugate is provided comprising the step of contacting a polymeric reagent as provided herein with an active agent under conditions suitable to provide a conjugate.

In still another embodiment of the invention, pharmaceutical preparations are provided comprising a conjugate of the invention in combination with a pharmaceutical excipient. The pharmaceutical preparations encompass all types of formulations and in particular those that are suited for injection, e.g., powders that can be reconstituted as well as suspensions and solutions.

In yet another embodiment, polymer-active agent conjugates are provided. Thus, for example, the invention provides a conjugate comprising a covalent bond between a nitrogen atom of an active agent to a secondary carbon atom, wherein the secondary carbon atom is attached through one or more atoms to a water-soluble polymer segment and the one or more atoms lacks a carbonyl moiety beta to the secondary carbon.

In an additional embodiment of the invention, a method for administering a conjugate is provided comprising the step of administering to a patient a conjugate provided herein. The conjugate is often provided as part of a pharmaceutical preparation. Any approach to administer the conjugate can be used and the invention is not limited in this regard. It is preferred, however, that the conjugate is administered via injection.

DETAILED DESCRIPTION OF THE INVENTION

I. Definitions and Overview

Figure 1:
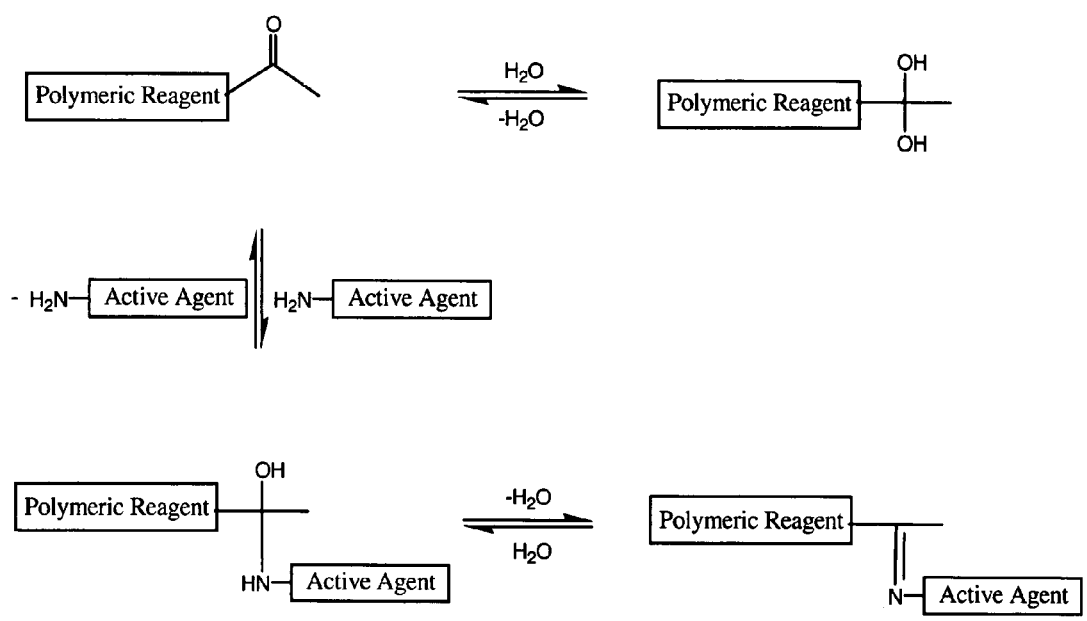
FIG. 1 is a schematic representation illustrating of the equilibria between a polymeric reagent bearing a ketone functional group and its hydrate in a conjugation reaction. A second equilibria representing condensation between a carbinolamine and the corresponding imine is also depicted.

Before describing the present invention in detail, it is to be understood that this invention is not limited to the particular polymers, synthetic techniques, active agents, and the like, as such may vary.

It must be noted that, as used in this specification and the claims, the singular forms "a," "an," and "the" include plural referents unless the context clearly dictates otherwise. Thus, for example, reference to "polymeric reagent" includes a single polymeric reagent as well as two or more of the same or different polymeric reagents, reference to a "conjugate" includes a single conjugate as well as two or more of the same of different conjugates, reference to an "excipient" includes a single excipient as well as two or more of the same or different excipients, and the like.

In describing and claiming the present invention, the following terminology will be used in accordance with the definitions described below.

"PEG," "polyethylene glycol" and "poly(ethylene glycol)" as used herein, are meant to encompass any water-soluble poly(ethylene oxide). Typically, PEGs for use in accordance with the invention comprise the following structure "—O(CH$_2$CH$_2$O)$_m$—" where (m) is 2 to 4000. As used herein, PEG also includes "—CH$_2$CH$_2$—O(CH$_2$CH$_2$O)$_m$—CH$_2$CH$_2$—" and "—(CH$_2$CH$_2$O)$_m$—," depending upon whether or not the terminal oxygens have been displaced. When the PEG further comprises a spacer moiety (to be described in greater detail below), the atoms comprising the spacer moiety, when covalently attached to a water-soluble polymer segment, do not result in the formation of an oxygen-oxygen bond (i.e., an "—O—O—" or peroxide linkage). Throughout the specification and claims, it should be remembered that the term "PEG" includes structures having various terminal or "end capping" groups and so forth. The term "PEG" also means a polymer that contains a majority, that is to say, greater than 50%, of —CH$_2$CH$_2$O— repeating subunits. With respect to specific forms, the PEG can take any number of a variety of molecular weights, as well as structures or geometries such as "branched," "linear," "forked," "multifunctional," and the like, to be described in greater detail below.

The terms "end-capped" and "terminally capped" are interchangeably used herein to refer to a terminal or endpoint of a polymer having an end-capping moiety. Typically, although not necessarily, the end-capping moiety comprises a hydroxy or C$_{1-20}$ alkoxy group, more preferably a C$_{1-10}$ alkoxy group, and more preferably a C$_{1-5}$ alkoxy group. Thus, examples of end-capping moieties include alkoxy (e.g., methoxy, ethoxy and benzyloxy), as well as aryl, heteroaryl, cyclo, heterocyclo, and the like. In addition, saturated, unsaturated, substituted and unsubstituted forms of each of the foregoing are envisioned. Moreover, the end-capping group can also be a silane. The end-capping group can also advantageously comprise a detectable label. When the polymer has an end-capping group comprising a detectable label, the amount or location of the polymer and/or the moiety (e.g., active agent) to which the polymer is coupled to can be determined by using a suitable detector. Such labels include, without limitation, fluorescers, chemiluminescers, moieties used in enzyme labeling, colorimetric (e.g., dyes), metal ions, radioactive moieties, and the like. Suitable detectors include photometers, films, spectrometers, and the like. The end-capping group can also advantageously comprise a phospholipid. When the polymer has an end-capping group comprising a phospholipid, unique properties (such as the ability to form organized structures with similarly end-capped polymers) are imparted to the polymer. Exemplary phospholipids include, without limitation, those selected from the class of phospholipids called phosphatidylcholines. Specific phospholipids include, without limitation, those selected from the group consisting of dilauroylphosphatidylcholine, dioleylphosphatidylcholine, dipalmitoylphosphatidylcholine, disteroylphosphatidylcholine, behenoylphosphatidylcholine, arachidoylphosphatidylcholine, and lecithin.

"Non-naturally occurring" means a polymer that in its entirety is not found in nature. A non-naturally occurring polymer may, however, contain one or more subunits or segments of subunits that are naturally occurring, so long as the overall polymer structure is not found in nature.

The term "water soluble" as in a "water-soluble polymer segment" and "water-soluble polymer" is any segment or polymer that is soluble in water at room temperature. Typically, a water-soluble polymer or segment will transmit at, least about 75%, more preferably at least about 95% of light, transmitted by the same solution after filtering. On a weight basis, a water-soluble polymer or segment thereof will preferably be at least about 35% (by weight) soluble in water, more preferably at least about 50% (by weight) soluble in water, still more preferably about 70% (by weight) soluble in water, and still more preferably about 85% (by weight) soluble in water. It is most preferred, however, that the water-soluble polymer or segment is about 95% (by weight) soluble in water or completely soluble in water.

"Nominal average molecular weight" in the context of a water-soluble, non-naturally occurring polymer of the invention such as PEG, refers to the mass average molecular weight, of the polymer, typically determined by size exclusion chromatography, light scattering techniques, or intrinsic velocity determination in 1,2,4-trichlorobenzene. The polymers of the invention are typically polydisperse, possessing low polydispersity values of preferably less than about 1.2, more preferably less than about 1.15, still more preferably less than about 1.10, yet still more preferably less than about 1.05, and most preferably less than about 1.03.

"Thiol derivative," in the context of a water-soluble, non-naturally occurring water soluble polymer, means such a polymer having at least one terminus that is a thiol group (—SH), a thiolate (—S—) or a protected thiol, that is to say, a thiol group in its protected form. Typical thiol protecting groups include thioether, thioester, or disulfide. Exemplary protecting groups for thiols can be found in Greene, T., and Wuts, Peter G. M., "PROTECTIVE GROUPS IN ORGANIC SYNTHESIS," Chapter 6, 3$^{rd}$ Edition, John Wiley and Sons, Inc., New York, 1999.

The terms "active" and "activated" when used in conjunction with a particular functional group, refers to a reactive functional group that reacts readily with an electrophile or a nucleophile on another molecule. This is in contrast to those groups that require strong catalysts or highly impractical reaction conditions in order to react (i.e., a "nonreactive" or "inert" group).

The terms "protected," "protecting group" and "protective group" refer to the presence of a moiety (i.e., the protecting group) that prevents or blocks reaction of a particular chemically reactive functional group in a molecule under certain reaction conditions. The protecting group will vary depending upon the type of chemically reactive group being protected as well as the reaction conditions to be employed and the presence of additional reactive or protecting groups in the molecule, if any. Protecting groups known in the art can be found in Greene, T. W., et al., PROTECTIVE GROUPS IN ORGANIC SYNTHESIS, 3rd ed., John Wiley & Sons, Inc., New York, N.Y. (1999).

As used herein, the term "functional group" or any synonym thereof is meant to encompass protected forms thereof.

An "organic radical," in the context describing a structure, a structural formula, a molecule, and so forth, refers to a carbon-containing moiety wherein a carbon atom provides a point of attachment. Exemplary organic radicals include, alkyl (e.g., lower alkyl), substituted alkyl (including heteroalkyl, and chain-substituted heteroalkyl), alkenyl, substituted alkenyl, alkynyl, substituted alkynyl, aryl, substituted aryl, heteroaryl, substituted heteroaryl, heterocyclicyl, substituted heterocyclicyl, and so forth.

A "nonaromatic-containing organic radical," in the context of describing a structure, a structural formula, a molecule, and so forth, refers to any "organic radical," as described above but excluding aryl, substituted aryl, heteroaryl, substituted heteroaryl, and alkyl or other groups that contain any aromatic group, e.g., aryl, substituted aryl, heteroaryl, substituted heteroaryl, and the like.

"Alkyl" refers to a hydrocarbon chain, typically ranging from about 1 to 15 atoms in length. Such hydrocarbon chains are preferably but not necessarily saturated and may be branched or straight chain, although typically straight chain is preferred. Exemplary alkyl groups include methyl, ethyl, propyl, butyl, pentyl, 1-methylbutyl, 1-ethylpropyl, 3-methylpentyl, and the like. As used herein, "alkyl" includes-cycloalkyl as well as cycloalkylene-containing alkyl.

"Lower alkyl" refers to an alkyl group containing from 1 to 6 carbon atoms, and may be straight chain or branched, as exemplified by methyl, ethyl, n-butyl, i-butyl, and t-butyl.

"Cycloalkyl" refers to a saturated or unsaturated cyclic hydrocarbon chain, including bridged, fused, or spiro cyclic compounds, preferably made up of 3 to about 12 carbon atoms, more preferably 3 to about 8 carbon atoms. "Cycloalkylene" refers to a cycloalkyl group that is inserted into an alkyl chain by bonding of the chain at any two carbons in the cyclic ring system.

"Alkoxy" refers to an —O—R group, wherein R is alkyl or substituted alkyl, preferably $C_{1-6}$ alkyl (e.g., methoxy, ethoxy, propyloxy, etc.).

As used herein, "alkenyl" refers to a branched or unbranched hydrocarbon group of 2 to 15 atoms in length, containing at least one double bond, such as ethenyl, n-propenyl, isopropenyl, n-butenyl, isobutenyl, octenyl, decenyl, tetradecenyl, and the like.

The term "alkynyl" as used herein refers to branched or unbranched hydrocarbon group of 2 to 15 atoms in length, containing at least one triple bond, and includes ethynyl, propynyl, butynyl, octynyl, decynyl, and so forth.

"Aryl" means one or more aromatic rings, each of 5 or 6 core carbon atoms. Aryl includes multiple aryl rings that may be fused, as in naphthyl, or unfused, as in biphenyl. Aryl rings may also be fused or unfused with one or more cyclic hydrocarbon, heteroaryl, or heterocyclic rings. As used herein, "aryl" includes heteroaryl.

"Heteroaryl" is an aryl group containing from one to four heteroatoms, wherein each heteroatom in the heteroaryl ring is preferably a sulfur, oxygen, or nitrogen atom. Heteroaryl rings may also be fused with one or more cyclic hydrocarbon, heterocyclic, aryl, or heteroaryl rings.

"Heterocyclicyl" or "heterocyclic" means a group of one or more rings of 5-12 atoms, preferably 5-7 atoms, with or without unsaturation or aromatic character and having at least one ring atom which is not a carbon. Preferred heteroatoms include sulfur, oxygen, and nitrogen.

The term "substituted" as in, for example, "substituted alkyl," refers to a moiety (e.g., an alkyl group) substituted with one or more non-interfering substituents, such as, but not limited to: $C_{3-8}$ cycloalkyl, e.g., cyclopropyl, cyclobutyl, and the like; halo, e.g., fluoro, chloro, bromo, and iodo; cyano; alkoxy; lower phenyl; substituted phenyl; and the like. "Substituted aryl" is aryl having one or more honinterfering groups as a substituent. For substitutions on a phenyl ring, the substituents may be in any orientation (i.e., ortho, meta, or para).

"Substituted heteroaryl" is heteroaryl having one or more noninterfering groups as substituents.

"Substituted heterocyclicyl" is a heterocyclicyl group having one or more side chains formed from noninterfering substituents.

"Noninterfering substituents" are those groups that, when present in a molecule, are typically nonreactive with other functional groups contained within the molecule.

"Electrophile" refers to an ion or atom or collection of atoms, that may be ionic, having an electrophilic center, i.e., a center that is electron seeking, capable of reacting with a nucleophile.

"Nucleophile" refers to an ion or atom or collection of atoms that may be ionic having a nucleophilic center, i.e., a center that is seeking an electrophilic center or with an electrophile.

A "physiologically cleavable" or "hydrolyzable" or "degradable" bond is a relatively weak bond that reacts with water (i.e., is hydrolyzed) under physiological conditions. Preferred are bonds that have a hydrolysis half-life at pH 8 and 25° C. of less than about 30 minutes. The tendency of a bond to hydrolyze in water will depend not only on the general type of linkage connecting two central atoms but also on the substituents attached to these central atoms. Appropriate hydrolytically unstable or weak linkages include, but are not limited to, carboxylate ester, phosphate ester, anhydrides, acyloxyalkyl ether, imines, and oligonucleotide bonds.

An "enzymatically degradable linkage" means a linkage that is subject to degradation by one or more enzymes.

A "hydrolytically stable" linkage or bond refers to a chemical bond, typically a covalent bond, that is substantially stable in water, that is to say, does not undergo hydrolysis under physiological conditions to any appreciable extent over an extended period of time. Examples of hydrolytically stable linkages include, but are not limited to, the following: carbon-carbon bonds (e.g., in aliphatic chains), ethers, amides, urethanes, and the like. Generally, a hydrolytically stable linkage is one that exhibits a rate of hydrolysis of less than about 1-2% per day under physiological conditions. Hydrolysis rates of representative chemical bonds can be found in most standard chemistry textbooks.

"Active agent," as described herein, includes any agent, drug, compound, composition of matter, or mixture that provides some pharmacologic, often beneficial, effect that can be demonstrated in-vivo or in vitro. This includes foods, food supplements, peptides, nutrients, nutriceuticals, drugs, vaccines, antibodies, vitamins, and other beneficial agents. As used herein, these terms further include any physiologically or pharmacologically active substance that produces a localized or systemic effect in a patient.

"Pharmaceutically acceptable excipient or carrier" refers to an excipient that may optionally be included in the compositions of the invention and that causes no significant adverse toxicological effects to thepatient. "Pharmacologically effective amount," "physiologically effective amount," and "therapeutically effective amount" are used interchangeably herein to mean the amount of a polymer-active agent conjugate that is needed to provide a desired level of active agent in the bloodstream or in the target tissue. The precise amount will depend upon numerous factors, e.g., the particular drug or therapeutic agent, the components and physical characteristics of the therapeutic composition, intended patient population, individual patient considerations, and the like, and can readily be determined by one skilled in the art, based upon the information provided herein.

"Multi-functional" means a polymer having 3 or more functional groups contained therein, where the functional groups may be the same or different. Multi-functional polymeric reagents of the invention will typically contain from about 3-100 functional groups, or from 3-50 functional groups, or from 3-25 functional groups, or from 3-15 functional groups, or from 3 to 10 functional groups, or will contain 3, 4, 5, 6, 7, 8, 9 or 10 functional groups within the polymer backbone.

A basic or acidic reactant described herein includes neutral, charged, and any corresponding salt forms thereof.

The term "patient," refers to a living organism suffering from or prone to a condition that can be prevented or treated by administration of an active agent, and includes both humans and animals.

"Optional" or "optionally" means that the subsequently described circumstance may or may not occur, so that the description includes instances where the circumstance occurs and instances where it does not.

The polymeric reagents described herein comprise a water-soluble polymer segment and a functional group. The functional group is selected from the group consisting of ketone, ketone hydrate, thione, monothiohydrate, dithiohydrate, hemiketal, monothiohemiketal, dithiohemiketal, ketal, and dithioketal. The functional group can be attached to the water-soluble polymer segment through a through a direct covalent bond. More typically, however, the functional group is attached to the water-soluble polymer segment through one or more atoms. Thus, in its most elemental form, the polymeric reagents described herein all share a core structure comprising:

POLY-------FG wherein POLY is a water-soluble polymer segment, FG is a functional group selected from the group consisting of ketone, ketone hydrate, thione, monothiohydrate, dithiohydrate, hemiketal, monothiohemiketal, dithiohemiketal, ketal, and dithioketal, and the dashed line represents a direct covalent bond or one or more atoms serving to attach the functional group to the water-soluble polymer segment. As will be seen in more detail below, the polymeric reagents described herein can have more complex structures.

Although not wishing to be bound by theory, it is believed that polymeric reagents bearing a ketone, ketone hydrate, thione, monothiohydrate, dithiohydrate, hemiketal, monothiohemiketal, dithiohemiketal, ketal, or dithioketal are more selective for use in conjugating to another substance (e.g., active agent) than a polymer bearing, for example, an aldehyde. One factor contributing to the increased selectivity of the polymeric reagents described herein is the relative stability associated with the functional group(s). As a result of being more stable, the functional group(s) of the polymeric reagent tend to only react with relatively more reactive moieties, thereby providing a greater degree of selectivity.

The increased stability of ketones, ketone hydrates, thiones, monothiohydrates, dithiohydrates, hemiketals, monothiohemiketals, dithiohemiketals, ketals, and dithioketals compared to other functional groups such as aldehydes is believed to be a function of two effects: electronic effects and steric effects. With respect to electronic effects, crowding at the functional group effectively provides the ability of the functional group to "share" the burden any ionization or "excess charge" that may occur during a reaction. Thus, for example, a ketone—having two carbon atoms attached on either side of a carbonyl carbon—can better absorb the electron-rich environment associated with a carbonyl moiety than the corresponding aldehyde, which has only one carbon.

With respect to steric effects, nucleophilc addition to the carbonyl group of both aldehydes and ketones changes the carbonyl carbon from $sp^2$ hybridization to $sp^3$ hybridization. The presence of a second—and relatively large—carbon atom associated with a ketone, however, slows the approach of the relatively bulky active agent to the $sp^2$ hybridized carbonyl carbon and sterically crowds the forming $sp^3$ hybridized carbon much more than the relatively small hydrogen associated with an aldehyde. As a consequence, the combination of both electronic and steric effects increases the activation energy of ketones and related functional groups by decreasing their starting energy state (i.e., by providing a stabilized carbonyl carbon, an electronic effect) and raising the energy of the transition state (i.e., the change from $sp^2$ to $sp^3$ hybridization, a steric effect). Thus, ketones and related functional groups are relatively more stable and hence less reactive.

Surprisingly, however, it has been found that the increased stability of ketone-, ketone hydrate-, thione-, monothiohydrate-, dithiohydrate-, hemiketal-, monothiohemiketal-, dithiohemiketal-, ketal-, or dithioketal-bearing polymeric reagents is advantageous. For example, an active agent may have several amine groups, each having its own reactivity toward a carbonyl moiety present on a polymeric reagent. By providing a relatively less reactive ketone-bearing polymeric reagent, conjugation will occur more preferentially between the least sterically hindered and most reactive amine(s) on the active agent and the carbonyl moiety of the ketone, thereby reducing the number of different conjugate forms.

Another advantage of the polymeric reagents described herein is that the functional group can be between two polymer chains (which may be linear), thereby providing the ability to attach two polymer chains through a single atom that is directly attached to an active agent, surface, or other moiety. Previously described branched polymeric reagents comprise a spacer moiety having a reactive group (e.g., aldehyde) for conjugation and separate and distinct branching atom that serves to link two polymer chains. In this way, the water-soluble polymer segments can be brought relatively closer to the active agent, thereby decreasing or eliminating entirely small "pendent" groups left behind on an active agent when a water-soluble polymer segment is cleaved from the conjugate.

II. Features of the Polymeric Reagents

A. The Functional Group ("FG")

As previously stated, the polymeric reagents of the invention are associated with a functional group selected from the group consisting of ketone, ketone hydrate, thione, monothiohydrate, dithiohydrate, hemiketal, monothiohemiketal, dithiohemiketal, ketal, and dithioketal. Structurally, each functional group ("FG") is shown below. In the structures, R stands for an organic radical, e.g., alkyl, and the "functional group carbon" is designated with an asterisk.

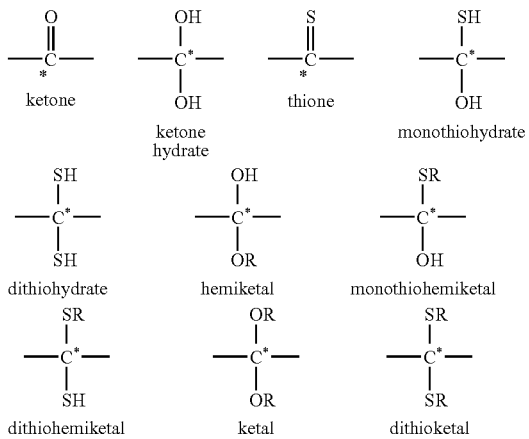

Although not shown, a carbon atom must be attached on each side of the functional group carbon in order to provide the named functional group.

Advantageously, the described functional groups are often easily transformed into each other. Thus, for example, some or all of a ketone can be transformed into a ketone hydrate by the addition of water. Moreover, in the presence of water, a ketone generally exists in an equilibrium with the corresponding hydrate. This is especially true with ketones having a proximate electron-withdrawing group. Because of equilibrium, as the amount of water in a ketone-containing system is decreased, the amount of the ketone hydrate species decreases. Thus, by controlling the amount of water in the system, it is possible to influence the amount (or ratio) of the two forms (e.g., ketone and ketone hydrate). Other factors, such as the presence or absence of electron-withdrawing and electron-donating groups and proximal steric hindrance, also influence the amount of and ratio between the two forms. Thione and monothiohydrate forms can also be provided in a similar fashion.

Usefully, conjugation reactions employing the presently described polymeric reagents can often proceed without regard to controlling the specific solvation status of the functional group. For example, it makes no difference whether the predominating species of the polymeric reagent is a ketone or a ketone hydrate; using one, the other, or both under conjugation conditions will result in the formation of polymer-active agent conjugates. While not wishing to be bound by theory, ketone hydrates—in equilibrium with the corresponding ketone—can be used because as the ketone species is being depleted during the conjugation reaction with the active agent, the equilibrium causes additional ketone hydrate species to be transformed into the corresponding ketone. The series of reactions is depicted in FIG. 1. As shown therein, two equilibria reactions are involved: the equilibria between the ketone and ketone hydrate in a polymeric reagent and the condensation processes involving an amine group on an active agent to form the carbinolamine and corresponding imine. Thus, while conjugation may proceed via the ketone, use of the corresponding ketone hydrate form will also result in formation of the desired conjugate. Again, while not wishing to be bound by theory, it is believed that increased stability of the hydrate form (as compared to the corresponding ketone form) corresponds to increased reactivity of the ketone form to conjugation to an active agent.

In addition, ketones can be converted into hemiketals through the addition of an alcohol. Again, as the amount of alcohol to a ketone-containing system is decreased, the amount of hemiketal species decreases. In this way, in equilibria reactions similar to those discussed above, it is possible to provide a hemiketal by adding alcohol to a ketone-containing system and providing a ketone by removing alcohol from a hemiketal-containing system. Moreover, in the presence of an acid catalyst, additional quantities of alcohol will transform a hemiketal into a ketal. In addition, ketones can be directly transformed into ketals by the addition of a diol, e.g., HO—$CH_2CH_2$—OH, in the presence of an acid catalyst. Advantageously, these and other ketals often serve as ketone protecting groups.

Figure 2:
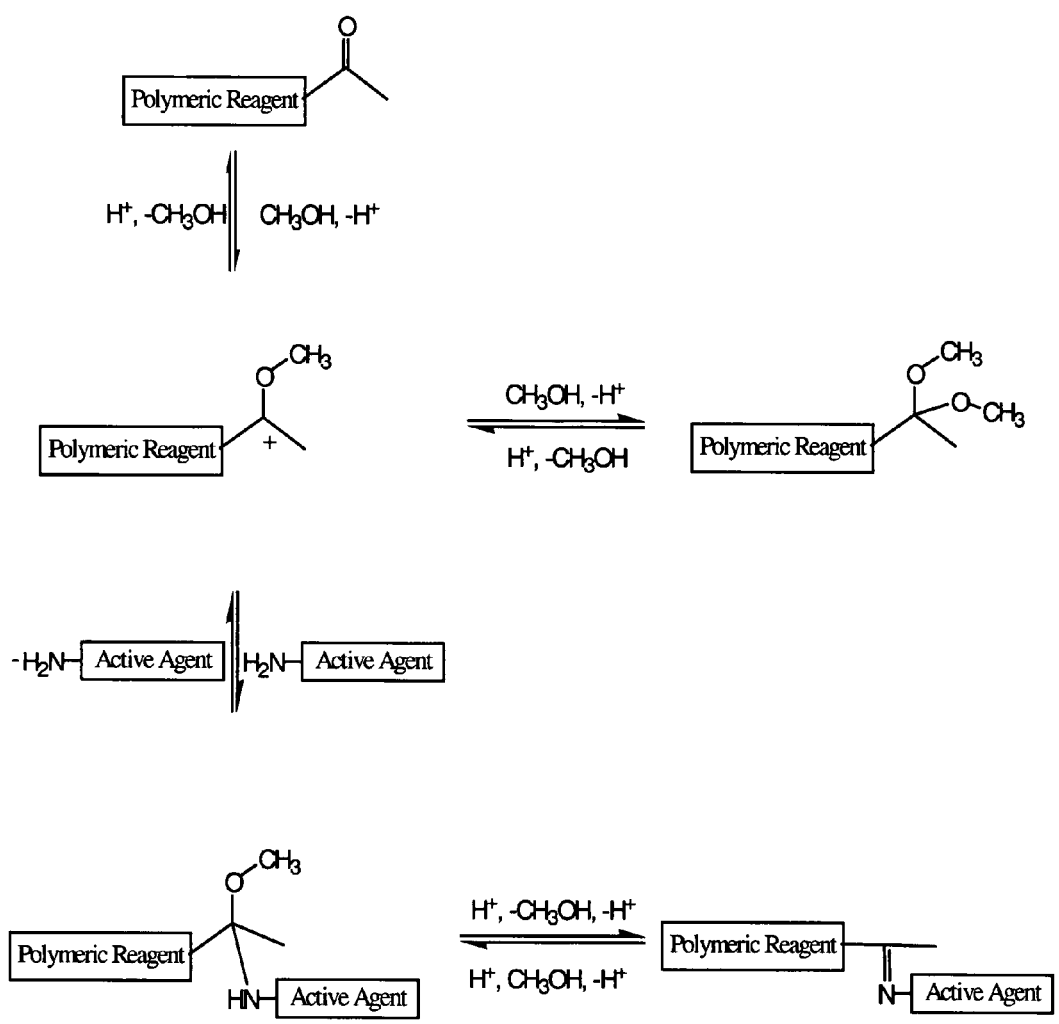
FIG. 2 is a schematic representation illustrating the formation of a ketal from a polymeric reagent bearing a ketone functional group, and of a conjugate from a polymeric reagent bearing ketal functional group.

FIG. 2 schematically depicts the formation of a ketal from a polymeric reagent bearing a ketone functional group, and of a conjugate from a polymeric reagent bearing a ketal functional group. In FIG. 2, a polymeric reagent bearing a ketone functional group can be initially converted into a reactive hemiketal intermediate, and then into the ketal (in this Figure, a dimethyl ketal). FIG. 2 also illustrates, through a series of equilibria, how ketals can be utilized directly in conjugation reactions with an amine-containing active agent.

In a similar way, thiones can be transformed into dithiohydrates (sometimes referred to as dithiosolvates) by solvating the thione in a sulfur-containing (e.g., hydrogen sulfide) environment. Thiones can also be transformed into dithiohemiketals in the presence of thiols, and into dithioketals in the presence of excess thiol. In a way analgous to ketones, thiones can be directly transformed into dithioketals by the addition of a dithiol, e.g., HS—$CH_2CH_2$—SH. Dithioketals often serve as thione protecting groups as well.

Although exemplary methods for transforming a given functional group into another functional group have been provided, the polymeric reagents are not limited in the manner in which the functional group is formed. Those of ordinary skill in the art know of other approaches for providing the functional groups described herein. Moreover, reference to any given functional group encompasses both the functional group per se, as well as to protected forms of the functional group.

B. The Water-Soluble Polymer Segment ("POLY," e.g., "$POLY^1$," "$POLY^2$," etc.)

The polymeric reagents of the invention also comprise at least one water-soluble polymer segment. Water-soluble polymer segments that are nonpeptidic and water-soluble, with from 2 to about 300 termini, are particularly useful in the invention. Examples of suitable water-soluble polymer segments include, but are not limited to, poly(alkylene glycols), such as poly(ethylene glycol) ("PEG"), copolymers of ethylene glycol and propylene glycol having water-solubility, poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazoline, poly(N-acryloylmorpholine), such as described in U.S. Pat. No. 5,629,384, and copolymers, terpolymers, and mixtures thereof. For purposes of the present invention, poly(propylene glycol) has insufficient water-solubility to act as a water-soluble polymer segment. Consequently, it is preferred that water-soluble polymer segments described herein do not contain propylene monomers.

It is preferred, however, that the water-soluble polymer segment is preferably, although not necessarily, a poly(ethylene glycol) ("PEG") or a derivative thereof. It should be understood, however, that related polymers are also suited for use in the practice of this invention and that the use of the term "PEG" or "poly(ethylene glycol)" is intended to be inclusive and not exclusive in this respect. Consequently, the term "PEG" includes poly(ethylene glycol) in any of its linear, branched or multi-arm forms, including alkoxy PEG, bifunctional PEG, forked PEG, branched PEG, pendant PEG, or PEG with degradable linkages therein, to be more fully described below.

In one form useful in the present invention, free or non-bound PEG is a linear polymer terminated at each end with hydroxyl groups:

HO—$CH_2CH_2$O—$(CH_2CH_2O)_{m'}$—$CH_2CH_2$—OH (m') typically ranges from zero to about 4,000.

The above polymer, alpha-, omega-dihydroxylpoly(ethylene glycol), can be represented in brief form as HO-PEG-OH where it is understood that the -PEG- symbol can represent the following structural unit:

—$CH_2CH_2$O—$(CH_2CH_2O)_{m'}$—$CH_2CH_2$— where (m') is as defined as above.

Another type of PEG useful in the present invention is methoxy-PEG-OH, or mPEG in brief, in which one terminus is the relatively inert methoxy group, while the other terminus is a hydroxyl group. The structure of mPEG is given below.

$CH_3$O—$CH_2CH_2$O—$(CH_2CH_2O)_{m'}$—$CH_2CH_2$—OH where (m') is as described above.

Multi-armed or branched PEG molecules, such as those described in U.S. Pat. No. 5,932,462, can also be used as the PEG polymer. For example, PEG can have the structure:

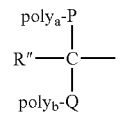

wherein:

$poly_a$ and $poly_b$ are PEG backbones (either the same or different), such as methoxy poly(ethylene glycol);

R" is a nonreactive moiety, such as H, methyl or a PEG backbone; and

P and Q are nonreactive linkages. In a preferred embodiment, the branched PEG polymer is methoxy poly(ethylene glycol) disubstituted lysine.

These polymers may be linear, or may be in any of the above-described forms (e.g., branched, forked, and the like).

In addition, the PEG can comprise a forked PEG. An example of a forked PEG is represented by the following structure:

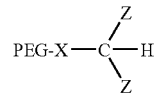

wherein: X is a spacer moiety and each Z is an activated terminal group linked to CH by a chain of atoms of defined length. International Application No. PCT/US99/05333, discloses various forked PEG structures capable of use in the present invention. The chain of atoms linking the Z functional groups to the branching carbon atom serve as a tethering group and may comprise, for example, alkyl chains, ether chains, ester chains, amide chains and combinations thereof.

The PEG polymer may comprise a pendant PEG molecule having reactive groups, such as carboxyl, covalently attached along the length of the PEG rather than at the end of the PEG chain. The pendant reactive groups can be attached to the PEG directly or through a spacer moiety, such as an alkylene group.

In addition to the above-described forms of PEG, the polymer can also be prepared with one or more weak or degradable linkages in the polymer, including any of the above described polymers. For example, PEG can be prepared with ester linkages in the polymer that are subject to hydrolysis. As shown below, this hydrolysis results in cleavage of the polymer into fragments of lower molecular weight:

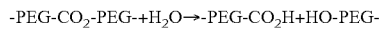

Other hydrolytically degradable linkages, useful as a degradable linkage within a polymer backbone, include: carbonate linkages; imine linkages resulting, for example, from reaction of an amine and an aldehyde (see, e.g., Ouchi et al. (1997) *Polymer Preprints* 38(1):582-3); phosphate ester linkages formed, for example, by reacting an alcohol with a phosphate group; hydrazone linkages which are typically formed by reaction of a hydrazide and an aldehyde; acetal linkages that are typically formed by reaction between an aldehyde and an alcohol; orthoester linkages that are, for example, formed by reaction between a formate and an alcohol; amide linkages formed by an amine group, e.g., at an end of a polymer such as PEG, and a carboxyl group of another PEG chain; urethane linkages formed from reaction of, e.g., a PEG with a terminal isocyanate group and a PEG alcohol; peptide linkages formed by an amine group, e.g., at an end of a polymer such as PEG, and a carboxyl group of a peptide; and oligonucleotide linkages formed by, for example, a phosphoramidite group, e.g., at the end of a polymer, and a 5' hydroxyl group of an oligonucleotide.

It is understood by those of ordinary skill in the art that the term poly(ethylene glycol) or PEG represents or includes all the above forms of PEG.

Although the nominal average molecular weight of the water-soluble polymer segment can vary, the nominal average molecular weight will satisfy one or more of the following values: greater than 100 Daltons; greater than 400 Daltons; greater than 500 Daltons, greater than 750 Daltons; greater than 900 Daltons; greater than 1,000 Daltons, greater than 1,400 Daltons; greater than 1,500 Daltons, greater than 1,900 Daltons; greater than 2,000 Daltons; greater than 2,200 Daltons; greater than 2,500 Daltons; greater than 3,000 Daltons; greater than 4,000 Daltons; greater than 4,900 Daltons; greater than 5,000 Daltons; greater than 6,000 Daltons; greater than 7,000 Daltons; greater than 7,500 Daltons, greater than 9,000 Daltons; greater than 10,000 Daltons; greater than 11,000 Daltons; greater than greater than 14,000 Daltons, greater than 15,000 Daltons; greater than 16,000 Daltons; 19,000 Daltons; greater than 20,000 Daltons; greater than 21,000 Daltons; greater than 22,000 Daltons, greater than 25,000 Daltons; and greater than 30,000 Daltons. It is understood that the maximum limit of molecular weight for any given water-soluble polymer segment useful herein is less than about 300,000 Daltons.

The nominal average molecular weight of the water-soluble polymer segment can also be expressed as being a value within a range of nominal average molecular weights. Exemplary ranges include: from about 100 Daltons to about 100,000 Daltons; from about 500 Daltons to about 80,000 Daltons; from about 1,000 Daltons to about 50,000 Daltons; from about 2,000 Daltons to about 25,000 Daltons; and from about 5,000 Daltons to about 20,000 Daltons.

Exemplary nominal average molecular weights for the water-soluble polymer segment include about 100 Daltons, about 200 Daltons, about 300 Daltons, about 400 Daltons, about 500 Daltons, about 600 Daltons, about 700 Daltons, about 750 Daltons, about 800 Daltons, about 900 Daltons, about 1,000 Daltons, about 2,000 Daltons, about 2,200 Daltons, about 2,500 Daltons, about 3,000 Daltons, about 4,000 Daltons, about 4,400 Daltons, about 5,000 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, about 20,000 Daltons, about 22,500 Daltons, about 25,000 Daltons, about 30,000 Daltons, about 40,000 Daltons, about 50,000 Daltons, about 60,000 Daltons, and about 75,000 Daltons.

With respect to PEG, wherein a structure corresponding to "—$CH_2CH_2O$—($CH_2CH_2O$)$_m$—$CH_2CH_2$—" can be provided, preferred values for (m) include: from about 3 to about 3,000; from about 10 to about 3,000; from about 15 to about 3,000; from about 20 to about 3,000; from about 25 to about 3,000; from about 30 to about 3,000; from about 40 to about 3,000; from about 50 to about 3,000; from about 55 to about 3,000; from about 75 to about 3,000; from about 100 to about 3,000; and from about 225 to about 3,000.

As used herein, the term "water-soluble polymer segment" includes those water-soluble polymer segments that are biocompatible and nonimmunogenic and specifically excludes any water-soluble polymer segments that are not biocompatible and nonimmunogenic. With respect to biocompatibility, a substance is considered biocompatible if the beneficial effects associated with use of the substance alone or with another substance (e.g., active agent) in connection with living tissues (e.g., administration to a patient) outweighs any deleterious effects as evaluated by a clinician, e.g., a physician. With respect to non-immunogenicity, a substance is considered nonimmunogenic if the intended use of the substance in vivo does not produce an undesired immune response (e.g., the formation of antibodies) or, if an immune response is produced, that such a response is not deemed clinically significant or important as evaluated by a clinician. It is particularly preferred that the water-soluble polymer segments described herein as well as conjugates are biocompatible and nonimmunogenic. As used herein, the term "water-soluble polymer segment" also excludes those water-soluble polymer segments made of monomers comprising one or more ketone moieties.

Those of ordinary skill in the art will recognize that the foregoing discussion concerning substantially water-soluble polymer segments is by no means exhaustive and is merely illustrative, and that all polymeric materials having the qualities described above are contemplated. As used herein, the term "polymeric reagent" generally refers to an entire molecule, which can comprise a water-soluble polymer segment and a functional group. The term "water-soluble polymer segment" is generally reserved for use in discussing one portion of a larger molecular structure such as a polymeric reagent, precursor molecule, conjugate, and so forth.

C. Attachment Through One or More Atoms

Each portion (e.g., functional group, active agent, water-soluble polymer segment, and so forth) of the polymeric reagent and other structures described herein can be directly attached to each other via a direct covalent bond. More typically, however, each portion is attached through one or more atoms serving to tether each portion together into a unified whole.

Preferred atoms through which the various portions of the polymeric reagents and other structures described herein include a chain of atoms made of carbon, nitrogen, oxygen, and/or sulfur atoms. Attached to this chain of atoms, can be one or more other atoms such as carbon, nitrogen, oxygen, sulfur, and hydrogen. The chain can be short and comprise as few as a chain of two to five atoms. Longer chains, for example, a chain of atoms of ten, fifteen, or more in length are also contemplated. Thus, a great number of different combinations of atoms are possible for attaching portions of the molecules described herein. Typically, however, three different groups of atoms are associated with linking the various portions of the polymeric reagents and other molecules described herein: a carbon chain; an electron withdrawing group; and a spacer moiety. Each will be discussed in turn.

(i) The Carbon Chain, (e.g.,

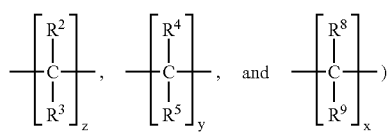

Optionally, one or more carbon chains is included in the polymeric reagent (as well as the corresponding conjugates, precursor molecules to form the polymeric reagents, and so forth). Typically, but not necessarily, the carbon chain is located immediately adjacent to the functional group of the polymeric reagent. Notwithstanding the absence of a carbon chain, however, a carbon atom (from, for example, a spacer moiety, organic radical, electron-withdraing group, and so forth) must be attached on each side of the functional group carbon.

When present, the carbon chain can have any number of carbon atoms so long as the overall polymeric reagent remains water soluble. Typically, however, there will be 1, 2, 3, 4, 5, 6, or 7 carbons in the carbon chain. Preferably, the polymeric reagent (as well as the corresponding precursor molecule, conjugate, and so forth) will lack a hydrocarbon chain of 8 carbons or greater. Thus, with respect to the various carbon chains structurally defined herein, each of (z), (y), and (x) can independently be zero, a positive integer, such as 1, 2, 3, 4, 5, 6, and 7, a positive integer from 1 to 7, a positive integer from 2 to 7, and so forth.

Due to its tetravalent character, each carbon in the carbon chain has two groups attached to it. As structurally defined herein, these groups have been designated as $R^2$, $R^3$, $R^4$, $R^5$, $R^8$ and $R^9$. Each of these groups, when present, is independently either hydrogen or an organic radical. A preferred form includes each occurrence of $R^2$, $R^3$, $R^4$, $R^5$, $R^8$ and $R^9$, when present, as hydrogen.

Exemplary classes of moieties from which any of $R^2$, $R^3$, $R^4$, $R^5$, $R^8$ and $R^9$ can independently be chosen from include H, alkyl, substituted alkyl, alkenyl, substituted alkenyl, alkynyl, substituted alkynyl, aryl, and substituted aryl. Although, as further explained below, aromatic moieties are preferably absent. Specific moieties from which any of $R^2$, $R^3$, $R^4$, $R^5$, $R^8$ and $R^9$ can independently be chosen from include H, methyl, ethyl, n-propyl, isopropyl, n-butyl, sec-butyl, isobutyl, tert-butyl, and vinyl. In addition, and two of $R^2$, $R^3$, $R^4$, $R^5$, $R^8$ and $R^9$ can be joined to form a cyclic ring system, which may bridge certain carbon chain atoms.

Another exemplary form includes defining the carbon chain as having an organic radical (e.g., a lower alkyl) attached to the carbon in the chain α to the functional group carbon. Advantageously, the presence of such an organic group in this position increases the selectivity of the polymeric reagent. While not wishing to be bound by theory, it is thought that the steric effects of the organic radical further increases the activation energy necessary for the functional group to react. An exemplary carbon chain (attached to a ketone having a terminal methyl group) showing the α carbon and a β carbon is provided below, wherein a methyl group is attached to the α carbon and all other substituents in the carbon chain are hydrogen.

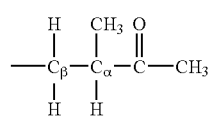

Preferably, when an organic radical is attached to a carbon α to the functional group carbon, the atom β to the functional group carbon is or is part of an electron-withdrawing group. Thus, exemplary arrangements are provided below wherein an oxygen atom is used as the electron-withdrawing group

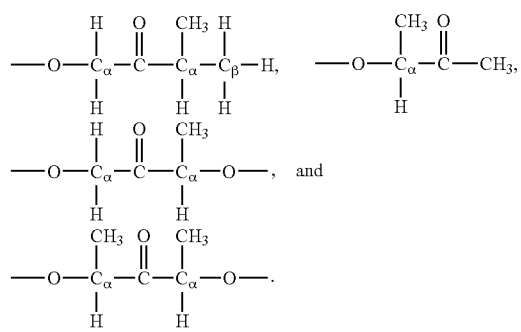

Although the above structures use oxygen as an electron-withdrawing group, electron-withdrawing groups other than oxygen (e.g., carbonyl) can be used.

When the carbon α to the functional group carbon bears an organic radical (e.g., methyl), the resulting polymeric reagent may comprise a chiral center. Specific chirality, however, is not explicitly illustrated herein with respect to any compound or structure comprising one or more chiral centers. Thus, the present discussion encompasses both the isomerically pure forms of any optically active compound described herein, as well as enantiomeric mixtures, including a racemic mixture, thereof.

Optionally, when two or more carbons are in the carbon chain, the carbon chain can include a carbon-carbon double bond. Such unsaturated groups can offer additional possibilities for reactions, such as the ability of the polymeric reagents to provide conjugate addition of a nucleophile to the β carbon of an α-β unsaturated ketone, as shown below.

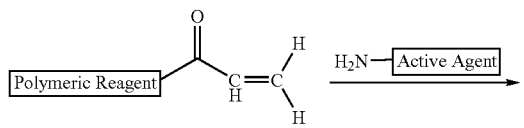

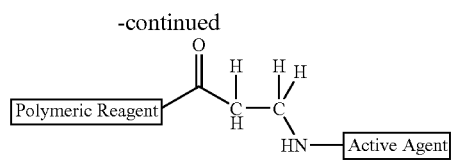

An α-β unsaturated ketone is often called an enone. Thus, while one or more carbon-carbon double bonds can be included at any position of the carbon chain, it is preferred that when a double bond is present, the double bond is located between the terminal α and β carbons relative to the functional group carbon (e.g., the carbonyl carbon). As will be discussed below, however, enones may preferably be absent from the polymeric reagents described herein.

(ii) The Electron Withdrawing Groups ("EW," e.g., "$EW^1$," "$EW^2$," "$EW^3$," etc.)

An electron-withdrawing group is optionally located within the polymeric reagent (or corresponding precursor molecule, conjugate, and so forth) and can comprise the atoms that serve to link various portions of a larger molecule together. An electron-withdrawing group is any atom or group of atoms including electronegative atom(s) and in some cases, having resonance interactions among some of the atoms in the electron-withdrawing group that create an enhanced electron-withdrawing effect. Electrons are attracted to the electronegative atom(s) of the electron-withdrawing group, thereby influencing the chemistry of a nearby functional group. The presence of an electron-withdrawing group adjacent (i.e., "α") to or within two to six atoms distant from the functional group carbon effectively destabilizes this carbon by withdrawing electrons, thereby increasing the overall reactivity of the functional group. Thus, for example, the presence of an electron-withdrawing group near a ketone group will increase its reactivity toward amines in a reductive amination reaction and other reactions wherein nucleophilic addition takes place.

It is preferred, however, that the presence and/or location of the electron-withdrawing group does not render the functional group overly reactive, thereby frustrating the ability to provide relative selectivity during, for example, conjugation reactions. One of ordinary skill in the art can determine whether any given electron-withdrawing group as well as whether the location of the electron-withdrawing group renders the functional group overly reactive. For example, conjugation techniques discussed herein can be performed using different polymeric reagents, each having a different electron-withdrawing group and/or an electron-withdrawing group at different distances from the functional group carbon. Those polymeric reagents providing desired reactivities as evidence through, for example, single conjugation to a protein, are not overly reactive.

Any electron-withdrawing group can be included and the invention is not limited in this regard. Generically, electron-withdrawing groups include —O—, —NH—, —NHC(O)—, —C(O)NH—, —OC(O)—, —OC(O)—, —OC(O)—NH—, —NH—OC(O)—, —C(O)—, —C(S)— and —C(OR)H—, wherein OR is an alkoxy or hydroxyl substituent. With respect to the structures then, electron-withdrawing groups designated as "$EW^1$" are preferably selected from the group consisting of —O—, —NH—, —NHC(O)—, —C(O)NH—, —OC(O)—, —OC(O)—, —OC(O)—NH—, —NH—OC(O)—, —C(O)—, —C(S)—, and —C(OR)H—, wherein OR is an alkoxy or hydroxyl substituent, while electron-withdrawing groups designated as "$EW^2$" and "$EW^3$" are each preferably independently selected from the group consisting of —O—, —NH—, —C(O)NH—, —NHC(O)—, —OC(O)—, —OC(O)—, —NH—OC(O)—, —OC(O)—NH—, —C(O)—, —C(S)— and —C(OR)H—, wherein OR is an alkoxy or hydroxy substituent. A preferred electron-withdrawing group is —C(O)—, either alone or as part of amide or carbamate. A particularly preferred electron-withdrawing group is —O—.

(iii) The Spacer Moiety ("X," e.g., "$X^1$," "$X^2$," "$X^3$," "$X^4$," "$X^5$," etc.)

Optionally, the polymeric reagents provided herein (as well as the corresponding precursor molecules, conjugates, and so forth) include a spacer moiety. Exemplary moieties suited for any spacer moiety designated as $X^1$ and $X^4$ are those independently selected from the group consisting of —O—, —S—, —C(O)—, —O—C(O)—, —C(O)—O—, —C(O)—NH—, —NH—C(O)—NH—, —O—C(O)—NH—, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—CH$_2$—C(O)—NH—, —C(O)—O—CH$_2$—, —CH$_2$—C(O)—O—CH$_2$—, —CH$_2$—CH$_2$—C(O)—O—CH$_2$—, —C(O)—O—CH$_2$—CH$_2$—, —NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$—, —CH$_2$—CH$_2$—NH—C(O)—CH$_2$—CH$_2$—, —C(O)—NH—CH$_2$—, —C(O)—NH—CH$_2$—CH$_2$—, —O—C(O)—NH—CH$_2$—, —O—C(O)—NH—CH$_2$—CH$_2$—, —O—C(O)—NH—CH$_2$—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—CH$_2$—C(O)—NH—CH$_2$—CH$_2$—NH—, —CH$_2$—CH$_2$—CH$_2$—C(O)—NH—CH$_2$—CH$_2$—NH—C(O)—, —CH$_2$—CH$_2$—CH$_2$—C(O)—NH—CH$_2$—CH$_2$—NH—C(O)—CH$_2$—, —CH$_2$—CH$_2$—CH$_2$—C(O)—NH—CH$_2$—CH$_2$—NH—C(O)—CH$_2$—CH$_2$—, —O—C(O)—NH—[CH$_2$]$_{0-6}$—(OCH$_2$CH$_2$)$_{0-2}$—, —C(O)—NH—(CH$_2$)$_{1-6}$—NH—C(O)—, —NH—C(O)—NH—(CH$_2$)$_{1-6}$—NH—C(O)—, —O—C(O)—CH$_2$—, —O—C(O)—CH$_2$—CH$_2$—, and —O—C(O)—CH$_2$—CH$_2$—CH$_2$—. Exemplary moieties suited for any spacer moiety designated as $X^2$, $X^3$, and $X^5$ include those independently selected from the group consisting of —O—, —S—, —C(O)—, —O—C(O)—, —C(O)—NH—, —NH—C(O)—NH—, —NH—C(O)—O—, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—, —O—CH$_2$—, —CH$_2$—CH$_2$—O—, —O—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—

—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —CH$_2$—NH—C(O)—, —CH$_2$—CH$_2$—NH—C(O)—, —CH$_2$—C(O)—NH—CH$_2$—, —NH—C(O)—CH$_2$—CH$_2$—, —CH$_2$—CH$_2$—CH$_2$—NH—C(O)—, —CH$_2$—C(O)—NH—CH$_2$—CH$_2$—, —CH$_2$—CH$_2$—C(O)—NH—CH$_2$—, —NH—C(O)—CH$_2$—CH$_2$—CH$_2$—, —CH$_2$—CH$_2$—CH$_2$—CH$_2$—NH—C(O)—, —CH$_2$—CR$_2$—CH$_2$—NH—C(O)—CH$_2$—, —CH$_2$—CH$_2$—NH—C(O)—CH$_2$—CH$_2$—, —CH$_2$—NH—C(O)—CH$_2$—CH$_2$—CH$_2$—, —CH$_2$—CH$_2$—NH—C(O)—CH$_2$—CH$_2$—CH$_2$—, —NH—C(O)—CH$_2$—CH$_2$—CH$_2$—, —NH—C(O)—CH$_2$—CH$_2$—CH$_2$—CH$_2$—, —CH$_2$—O—C(O)—, —CH$_2$—O—C(O)—CH$_2$—, —CH$_2$—O—C(O)—CH$_2$—CH$_2$—, —CH$_2$—CH$_2$—O—C(O)—, —CH$_2$—C(O)—NH—, —CH$_2$—C(O)—NH—CH$_2$—, —CH$_2$—C(O)—NH—CH$_2$—CH$_2$—, —CH$_2$—CH$_2$—C(O)—NH—, —CH$_2$—CH$_2$—C(O)—NH—CH$_2$—, —CH$_2$—CH$_2$—C(O)—NH—CH$_2$—CH$_2$—, —C(O)—NH—CH$_2$—, —C(O)—NH—CH$_2$—CH$_2$—, —CH$_2$—NH—C(O)—O—, —CH$_2$—CH$_2$—NH—C(O)—O—, —CH$_2$—CH$_2$—CH$_2$—NH—C(O)—O—, —CH$_2$—NH—, —CH$_2$—CH$_2$—NH—, —CH$_2$—NH—CH$_2$—, —CH$_2$—NH—CH$_2$—CH$_2$—, —CH$_2$—C(O)—, —CH$_2$—CH$_2$—C(O)—, —CH$_2$—C(O)—CH$_2$—, —CH$_2$—C(O)—CH$_2$—CH$_2$—, —CH$_2$—CH$_2$—C(O)—CH$_2$—CH$_2$—, —C(O)—CH$_2$—CH$_2$—, —NH—CH$_2$—CH$_2$—NH—C(O)—CH$_2$—CH$_2$—CH$_2$—, —C(O)—NH—CH$_2$—CH$_2$—NH—C(O)—CH$_2$—CH$_2$—CH$_2$—, —CH$_2$—C(O)—NH—CH$_2$—CH$_2$—NH—C(O)—CH$_2$—CH$_2$—CH$_2$—, —CH$_2$—C(O)—NH—CH$_2$—CH$_2$—NH—C(O)—CH$_2$—CH$_2$—, —(CH$_2$CH$_2$O)$_{0-2}$—(CH$_2$)$_{0-6}$—NH—C(O)—O—, —C(O)—NH—(CH$_2$)$_{1-6}$—NH—C(O)—, —C(O)—NH—(CH$_2$)$_{1-6}$—NH—C(O)—NH—, —CH$_2$—C(O)—O—, —CH$_2$—CH$_2$—C(O)—O—, and —CH$_2$—CH$_2$—CH$_2$—C(O)—O—.

In any of the above, a simple cycloalkylene group, e.g., 1,3- or 1,4-cyclohexylene, may replace any two, three, or four carbon alkylene group.

For purposes of the present disclosure, however, a series of atoms is not a spacer moiety when the series of atoms is immediately adjacent to a water-soluble polymer segment and the series of atoms is but another monomer, such that the proposed spacer moiety would represent a mere extension of the polymer chain. For example, given the partial structure "POLY-X—," and POLY is defined as "CH$_3$O(CH$_2$CH$_2$O)$_m$—" wherein (m) is 2 to 4000 and X is defined as a spacer moiety, the spacer moiety cannot be defined as "—CH$_2$CH$_2$O—" since such a definition would merely represent an extension of the polymer. In such a case, however, an acceptable spacer moiety could be defined as "—CH$_2$CH$_2$—."

D. Other Features

In addition to those features already described, the polymeric reagents (and corresponding precursor molecules and conjugates) can have other optional features.

For example, the entire polymeric reagent (as well as the organic radicals present in the polymeric reagent) preferably lacks an aromatic moiety. As used herein, an entity lacks an aromatic moiety when the entity is completely free of a conjugated system of π electrons that closes upon itself. Typical of aromatic moieties are those that comprise a benzene,

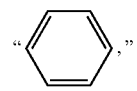

structure. The presence of an aromatic structure is undesired because such structures decrease water solubility and can result in harmful effects in vivo. For the same reasons, the polymeric reagents also preferably lack halogen atoms (e.g., F, Cl, Br and I) in their structures. The presence of either halogen atoms or aromatic moieties can be warranted in certain circumstances, however, such as in a method for making a polymeric reagent wherein protection groups include aromatic or halogen atoms. In addition, ionized forms of halogens can also be useful to form salts, which are not typically harmful in moderate amounts. As used herein, a polymeric reagent lacking a halogen atom does not include instances wherein the polymeric reagent (or conjugate formed therefrom) is in a salt form having a halogen counterion.

In addition, the polymeric reagents preferably lack a cyclic dienone. As used herein, a cyclic dienone is a ketone wherein the carbonyl carbon is part of a cyclic structure and the α,β carbons on either side of the carbonyl carbon are have a double bond. Schematically, the core structure of cyclic dienones can be generically represented as:

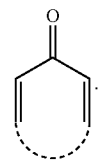

Exemplary cyclic dienones lacking in the polymeric reagents include the following:

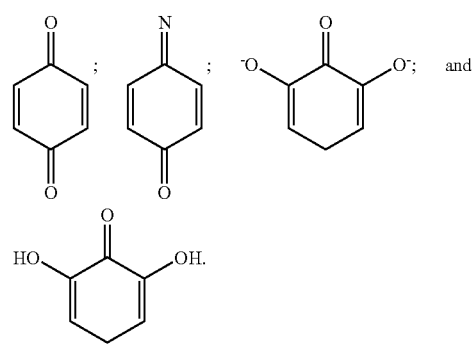

It is believed that the presence of such doubly α,β-unsaturated structures in a polymeric reagent may result in conjugate addition of a nucleophile. This approach to conjugation may not, however, have the same selectivity as, for example, reductive amination through a ketone. Consequently, the polymeric reagents preferably lack cyclic dienones. Moreover, it can also be the case that the polymeric reagents also lack an enone (i.e., an α,β-unsaturated ketone). When, however, an alternative conjugation approach is desired, an enone can be present.

In addition, the polymeric reagents also preferably lack other reactive groups that could impede the selectivity. For example, the polymeric reagents preferably lack a terminal oxylamine group (i.e., —ONH$_2$). In addition, the polymeric reagents also preferably lack a terminal hydrazine group (i.e., —NHNH$_2$).

In some cases, the polymeric reagents of the invention are not in certain forms. Thus, for example, the polymeric reagents are not in the following forms:

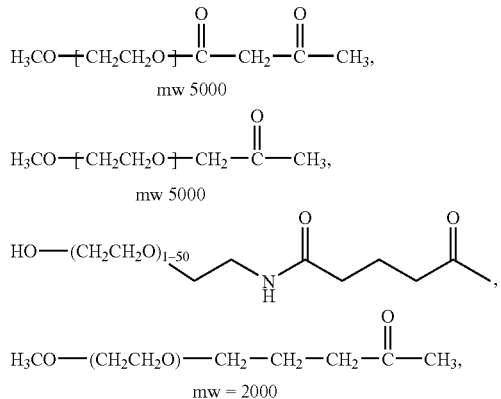

and ketal derivatives of any of the foregoing. It will be understood that "mw" refers to the weight average molecular weight of the ethylene oxide moiety, and that a range such as "1-50" provided adjacent to a monomer indicates that the moiety encompasses the monomer repeating from 1 to 50 times, inclusive.

E. Structurally Defined Polymeric Reagents

As will be described in further detail below, the polymeric reagents of the invention can be provided in a number of forms.

In some instances, the polymeric reagent is linear in form and comprises a single water-soluble polymer segment and a single functional group. An exemplary polymeric reagent of this form comprises the following structure:

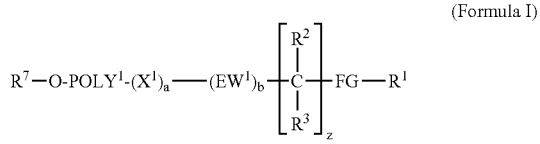
(Formula I)

wherein:

POLY$^1$ is a water-soluble polymer segment having a terminus defined as —O—R$^7$;

(a) is either zero or one;

(b) is either zero or one;

X$^1$, when present, is a spacer moiety;

EW$^1$, when present, is an electron-withdrawing group;

(z) is an integer from 2 to 7;

each occurrence of R$^2$ is independently H or a nonaromatic-containing organic radical;

each occurrence of R$^3$ is independently H or a nonaromatic-containing organic radical;

R$^7$ is H or a nonaromatic-containing organic radical;

FG is a functional group selected from ketone, ketone hydrate, thione, monothiohydrate, dithiohydrate, hemiketal, monothiohemiketal, dithiohemiketal, ketal, and dithioketal; and R$^1$ is a nonaromatic-containing organic radical;

and further wherein the

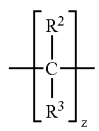

moiety optionally contains one or more double bonds, with the proviso that the polymeric reagent is neither

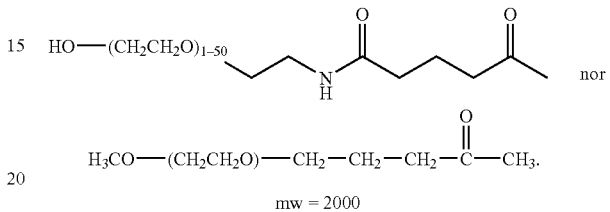

nor

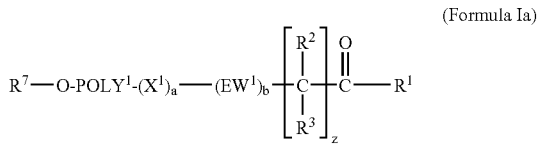

An exemplary polymeric reagent having a linear arrangement and a ketone has the following structure:

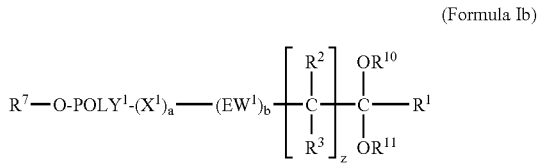
(Formula Ia)

wherein R$^7$, POLY$^1$, X$^1$, EW$^1$, R$^1$, R$^2$, R$^3$, (a), (b), and (z) are as previously defined with respect to Formula I.

The corresponding ketal has the following structure:

(Formula Ib)

wherein R$^7$, POLY$^1$, X$^1$, EW$^1$, R$^2$, R$^3$, (a), (b), (z) and R$^1$ are as previously defined with respect to Formula I, and further wherein R$^{10}$ is a organic radical (preferably nonaromatic), R$^{11}$ is an organic radical (preferably nonaromatic), or R$^{10}$ and R$^{11}$ combine to form a cyclic ketal (preferably nonaromatic, e.g., an alkylene such as an ethylene or substituted ethylene).

An exemplary polymeric reagent having a linear arrangement and a ketone hydrate has the following structure:

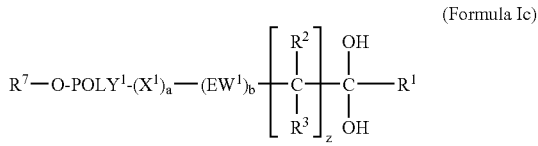
(Formula Ic)

wherein R$^7$, POLY$^1$, X$^1$, EW$^1$, R$^2$, R$^3$, R$^1$, (a), (b), and (z) are as previously defined with respect to Formula I.

More specific (although nonlimiting) examples polymeric reagents of this form include those selected from the group consisting of:

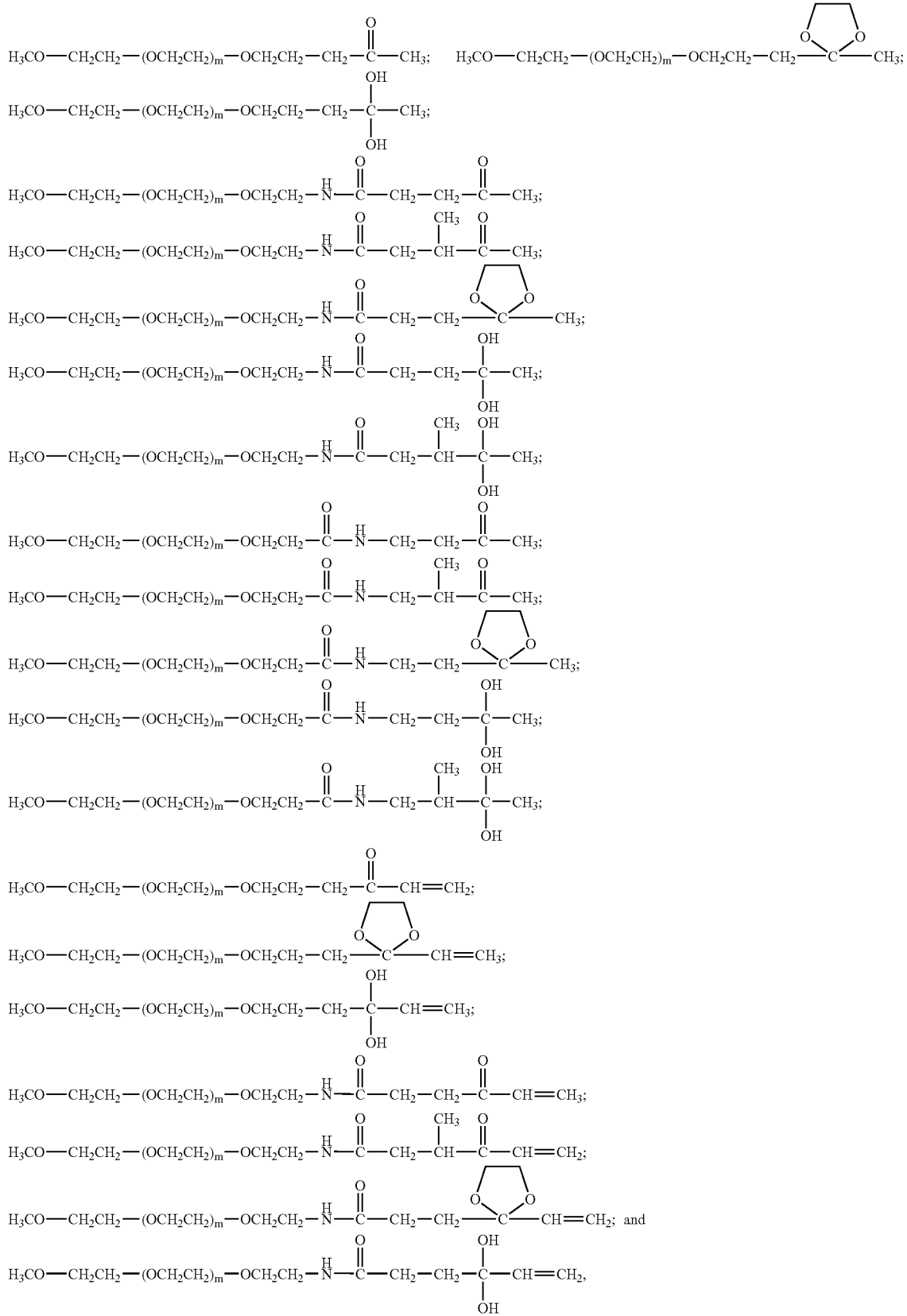
wherein (m) is from about 3 to about 3000.

Another example of a linear polymeric reagent of the invention is a polymeric reagent comprised of a carbon-containing functional group and a water-soluble polymer segment, wherein the carbon of the carbon-containing functional group is part of a cyclic structure and further wherein the cyclic structure is attached to the water-soluble polymer segment through either a direct covalent bond or through a spacer moiety, wherein the functional group is selected from the group consisting of ketone, ketone hydrate, thione, monothiohydrate, dithiohydrate, hemiketal, monothiohemiketal, dithiohemiketal, ketal, and dithioketal.

With respect to the cyclic structure, any nonaromatic ring can be used and the invention is not limited in this regard. Exemplary cyclic structures include: piperidinyl, e.g.,

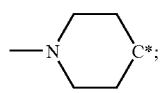

cyclohexyl, e.g.,

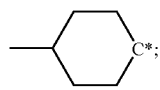

cyclopentyl, e.g.,

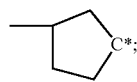

bicyclo[2,2,1]heptanyl, e.g.,

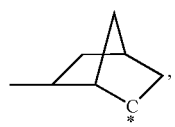

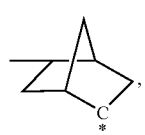 and 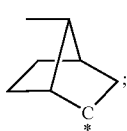

bicyclo[2,2,1]hexanyl, bicyclo[3,2,1]octanyl, bicyclo[3,3,1] nonanyl, cyclobutyl, e.g.,

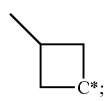

cylcoheptyl, e.g.,

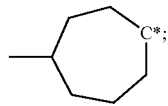

and cyclooctyl, e.g.,

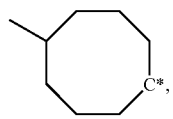

oxa and aza forms thereof and dioxa and diaza forms of any of the foregoing.

Preferably, when one or more heteroatoms are present in the cyclic structure, at least one heteroatom is situated in the alpha or beta position of the functional group carbon. Exemplary heteroatom-containing cyclic structures wherein a heteroatom is situated at a beta position include: oxacyclohexyl, e.g.,

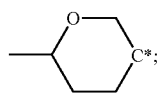

azacyclopentyl, e.g.,

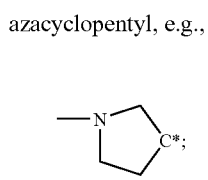

oxabicyclo[2,2,1]heptanyl, e.g.,

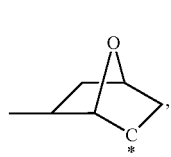

and dioxacyclooctyl, e.g.,

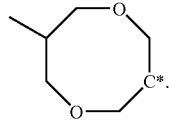

Although any carbon in the cyclic structure can be the functional group carbon, exemplary placements of the functional group carbon have been designated with an asterisk.

Diaza forms of cyclic structures, useful in reacting with polymeric active esters to form branched products, include the following:

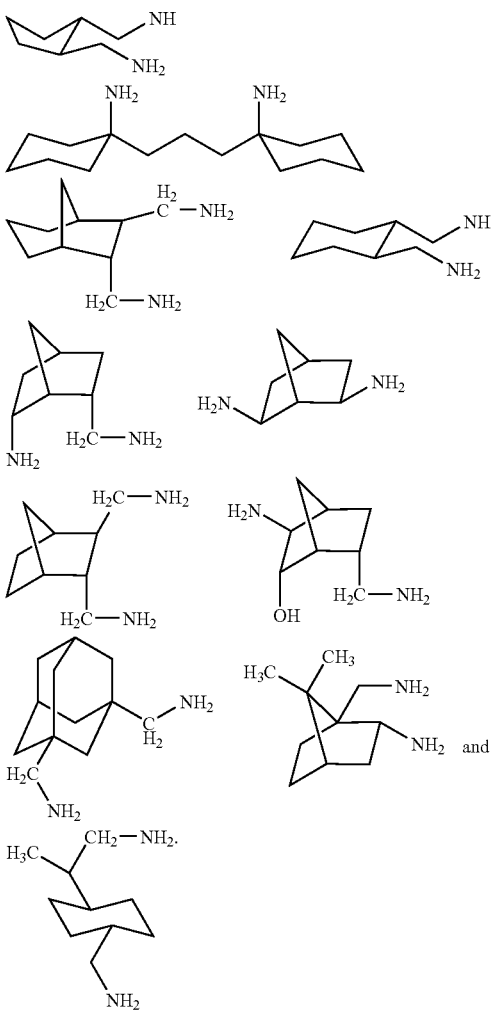

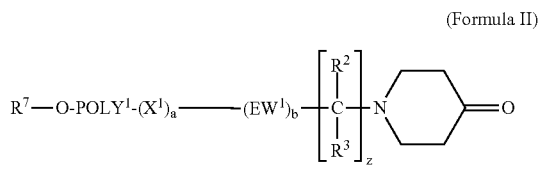

Again, any carbon in the cyclic structure can be the functional group carbon, wherein the functional group is selected from the group consisting of ketone, ketone hydrate, thione, monothiohydrate, dithiohydrate, hemiketal, monothiohemiketal, dithiohemiketal, ketal, and dithioketal.

Examples of polymeric reagents having a heteroatom in a cyclic structure comprising a ketone are shown in Formula II. The cyclic structure in Formula II comprises a piperidonyl cyclic moiety.

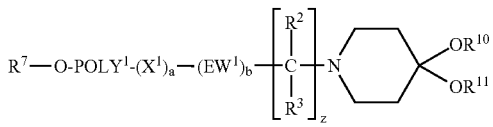
(Formula II)

wherein:

$POLY^1$ is a water-soluble polymer segment having a terminus defined as $-O-R^7$;

(a) is either zero or one;
(b) is either zero or one;
$X^1$, when present, is a spacer moiety;
$EW^1$, when present, is an electron-withdrawing group;
(z) is zero or a positive an integer;

each occurrence of $R^2$, when present, is independently H or an organic radical;

each occurrence of $R^3$, when present, is independently H or an organic radical; and $R^7$ is H or an organic radical.

The corresponding ketal derivative has the following structure:

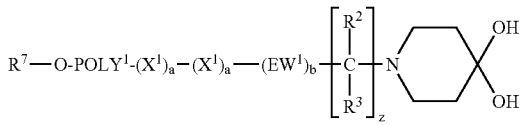
(Formula IIa)

wherein $R^7$, $POLY^1$, $X^1$, $EW^1$, $R^2$, $R^3$, (a), (b), and (z) are as previously defined with respect to Formula II, and further wherein $R^{10}$ is a organic radical (preferably nonaromatic), $R^{11}$ is an organic radical (preferably nonaromatic), or $R^{10}$ and $R^{11}$ combine to form a cyclic ketal (preferably nonaromatic, e.g., an alkylene such as an ethylene or substituted ethylene).

An exemplary polymeric reagent having a linear arrangement and a ketone hydrate has the following structure (Formula IIb)

$$R^7-O-POLY^1-(X^1)_a-(X^1)_a-(EW^1)_b\left[\begin{array}{c}R^2\\|\\C\\|\\R^3\end{array}\right]_z-N\begin{array}{c}OH\\OH\end{array}$$

wherein $R^7$, $POLY^1$, $X^1$, $EW^1$, $R^2$, $R^3$, (a), (b), and (z) are as previously defined with respect to Formula II.

When a cyclic structure containing a functional group is present in the polymeric reagent, it is particularly preferred that the cyclic structure is attached directly to an electron-withdrawing or a spacer moiety. Thus, for example, with respect to each of Formulas II, IIa, and IIb, it is preferred that (z) is zero. Furthermore, it is particularly preferred that the electron withdrawing group ($EW^1$) is carbonyl. Thus, preferred polymeric reagents taking this form are encompassed by the following structures

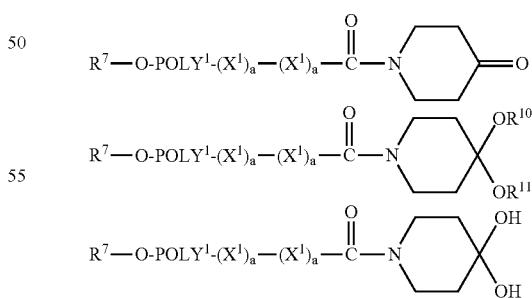

wherein (a), $R^7$, $POLY^1$, and $X^1$ for each of Formulas IIc, IId, and IIe are as previously defined with respect to Formula II, and $R^{10}$ and $R^{11}$ for Formula IId are as previously defined with respect to Formula IIa.

Exemplary polymeric reagents of this form include, but are not limited to, the following:

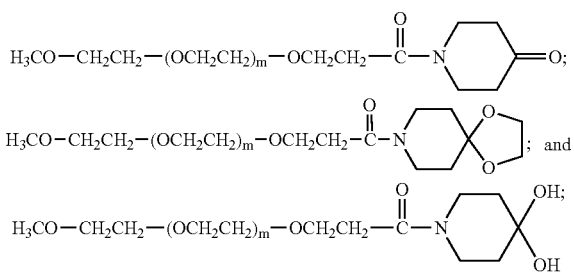

wherein (m) is from about 3 to about 3000.

In some instances, the polymeric reagent is linear in form and comprises a single water-soluble polymer segment and more than one functional group. An exemplary polymeric reagent of this form comprises the following structure:

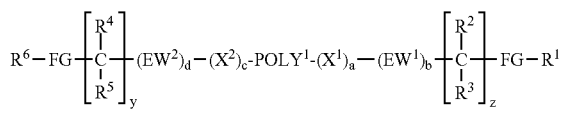
(Formula III)

wherein:

$POLY^1$ is a water-soluble polymer segment having a molecular weight of greater than 2,200 Daltons;
(a) is either zero or one;
(b) is either zero or one;
(c) is either zero or one;
(d) is either zero or one;
$X^1$, when present, is a spacer moiety;
$X^2$, when present is a spacer moiety;
$EW^1$, when present, is an electron-withdrawing group;
$EW^2$, when present, is an electron-withdrawing group;
(z) is zero or a positive integer from 1 to 7;
(y) is zero or a positive integer from 1 to 7;
each occurrence of $R^2$, when present, is independently H or an organic radical;
each occurrence of $R^3$, when present, is independently H or an organic radical;
each occurrence of $R^4$, when present, is independently H or an organic radical;
each occurrence of $R^5$, when present, is independently H or an organic radical;
FG-$R^1$ is either (i) a functional group selected from the group consisting of ketone, ketone hydrate, thione, monothiohydrate, dithiohydrate, hemiketal, monothiohemiketal, dithiohemiketal, ketal, and dithioketal having a terminus defined as $R^1$, wherein $R^1$ is an organic radical, or (ii) a nondienone cyclic structure wherein a functional group selected from the group consisting of ketone, ketone hydrate, thione, monothiohydrate, dithiohydrate, hemiketal, monothiohemiketal, dithiohemiketal, ketal, and dithioketal is part of the cyclic structure; and
FG-$R^6$ is either (i) a functional group selected from the group consisting of ketone, ketone hydrate, thione, monothiohydrate, dithiohydrate, hemiketal, monothiohemiketal, dithiohemiketal, ketal, and dithioketal having a terminus defined as $R^6$, wherein $R^6$ is an organic radical, or (ii) a nondienone cyclic structure wherein a functional group selected from the group consisting of ketone, ketone hydrate, thione, monothiohydrate, dithiohydrate, hemiketal, monothiohemiketal, dithiohemiketal, ketal, and dithioketal is part of the cyclic structure.

A particularly preferred polymeric reagent of this form comprises the following structure:

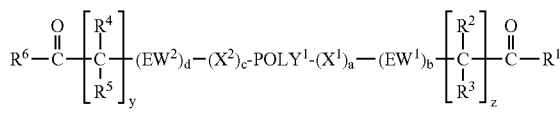
(Formula IIIa)

wherein $POLY^1$, (a), (b), (c), (d), $X^1$, $X^2$, $EW^1$, $EW^2$, (z), (y), $R^1$, $R^2$, $R^3$, $R^4$, $R^5$, and $R^6$ are as previously defined with respect to Formula III.

A corresponding ketal-containing version of Formula (IIIa) comprises the following structure:

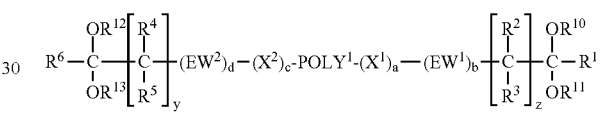
(Formula IIIb)

wherein $POLY^1$, (a), (b), (c), (d), $X^1$, $X^2$, $EW^1$, $EW^2$, (z), (y), $R^1$, $R^2$, $R^3$, $R^4$, $R^5$, and $R^6$ area as previously defined with respect to Formula (III), and further wherein $R^{10}$ is an organic radical (preferably nonaromatic), $R^{11}$ is an organic radical (preferably nonaromatic), $R^{12}$ is an organic radical (preferably nonaromatic), $R^{13}$ is an organic radical (preferably nonaromatic), or $R^{10}$ and $R^{11}$ combine to form a cyclic ketal (preferably nonaromatic, e.g., an alkylene such as ethylene or substituted ethylene), and $R^{12}$ and $R^{13}$ combine to form a cyclic ketal (preferably nonaromatic, e.g., an alkylene such as ethylene or substituted ethylene).

The corresponding ketone hydrate of Formula III comprises the following structure:

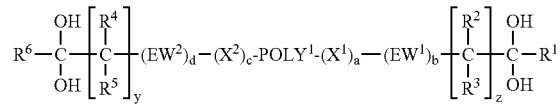
(Formula IIIc)

wherein $POLY^1$, (a), (b), (c), (d), $X^1$, $X^2$, $EW^1$, $EW^2$, (z), (y), $R^1$, $R^2$, $R^3$, $R^4$, $R^5$, and $R^6$ are as previously defined with respect to Formula III.

Exemplary forms of the polymeric reagents in accordance with Formula III include:

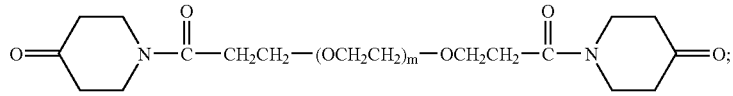

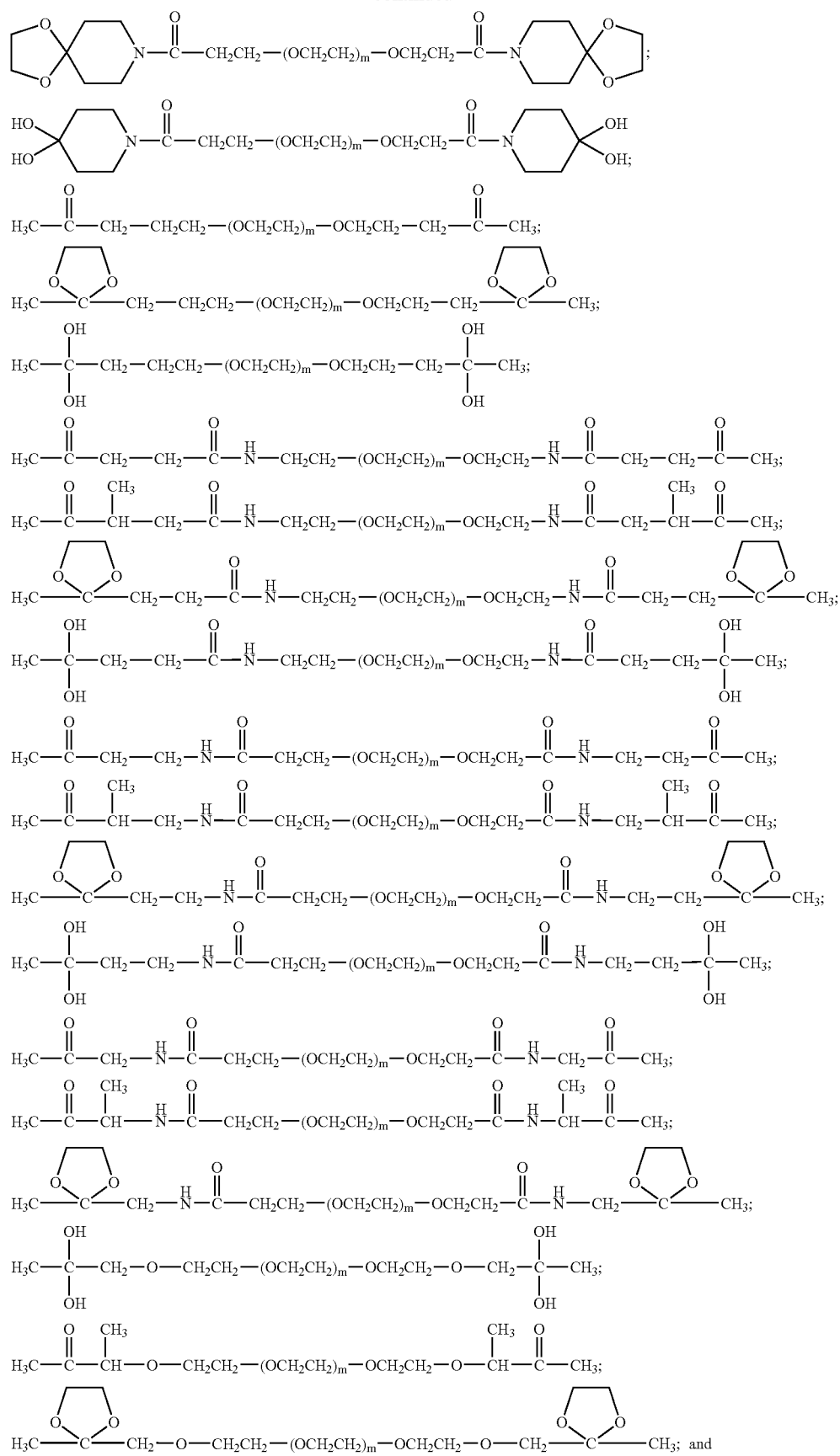

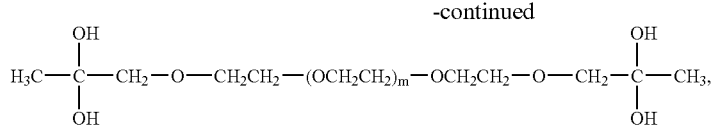

wherein (m) is from about 55 to about 3000.

Another class of reagents that may advantageously contain a ketone group or one of its forms are heterobifunctional polymeric reagents. Of most use are those that react with different types of biomolecules. For example, one may have a ketone that would react with an amine group in a protein or polypeptide and a maleimide functional group that would react with a thiol group in a different protein or polypeptide. An exemplary form of the aforementioned heterobifunctional polymeric reagent is shown below,

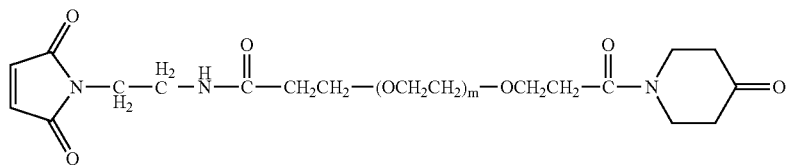

wherein (m) is from about 3 to about 3000.

These and other heterobifunctional forms wherein one functional group of the polymeric reagent is selected from the group consisting of ketone, ketone hydrate, thione, monothiohydrate, dithiohydrate, hemiketal, monothiohemiketal, dithiohemiketal, ketal, and dithioketal, are encompassed within the present invention.

Advantageously, the polymeric reagents of the invention can comprise more than a single water-soluble polymer segment. Often, such polymeric reagents are conventionally referred to as "branched." As will be seen in further detail below, branching can be effected in the currently described polymers at the functional group carbon or at a point other than the functional group carbon. Branching effected at the functional group carbon provides a linear and branched polymeric reagent, thereby providing a "V" arrangement. Branching effected by a moiety other than the functional group carbon is typically nonlinear and the resulting polymeric reagent is often in the form of a letter "Y."

An exemplary branched polymeric reagent (linear or otherwise) is comprised of a first water-soluble polymer segment, a second water-soluble polymer segment, and a functional group selected from the group consisting of ketone, ketone hydrate, thione, monothiohydrate, dithiohydrate, hemiketal, monothiohemiketal, dithiohemiketal, ketal, and dithioketal, wherein each of the first and second water-soluble polymer segments are attached, either through a direct covalent bond or through one or more atoms, to the functional group and further wherein when the functional group is a ketone, ketone hydrate, hemiketal or ketal: (a) the polymeric reagent lacks an aromatic moiety; or (b) each water-soluble polymer segment in the polymeric reagent has a weight average molecule weight of 1000 Daltons or greater.

Thus, for example, the branched polymeric reagents of the invention include those comprising the following structure:

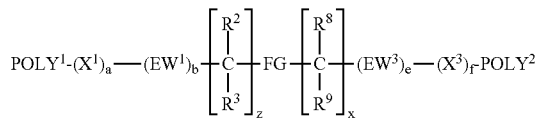

wherein:
POLY$^1$ is the first water-soluble polymer segment;
POLY$^2$ is the second water-soluble polymer segment;
(a) is either zero or one;
(b) is either zero or one;
(e) is either zero or one;
(f) is either zero or one;
X$^1$, when present, is a spacer moiety;
X$^3$, when present is a spacer moiety;
EW$^1$, when present, is an electron-withdrawing group;
EW$^3$, when present, is an electron-withdrawing group;
(z) is zero or a positive integer from 1 to 7;
(x) is zero or a positive integer from 1 to 7;
each occurrence of R$^2$, when present, is independently H or an organic radical;
each occurrence of R$^3$, when present, is independently H or an organic radical;
each occurrence of R$^8$, when present, is independently H or an organic radical;
each occurrence of R$^9$, when present, is independently H or an organic radical; and
FG is the functional group selected from ketone, ketone hydrate, thione, monothiohydrate, dithiohydrate, hemiketal, monothiohemiketal, dithiohemiketal, ketal, and dithioketal.

A ketone-containing polymeric reagent of Formula IV comprises the following structure:

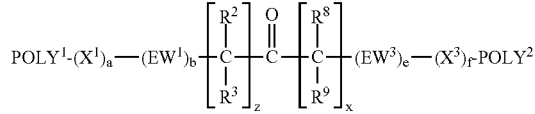

wherein POLY$^1$, POLY$^2$, (a), (b), (e), (f), (z), (x), X$^1$, EW$^1$, EW$^3$, and X$^3$ are as previously defined with respect to Formula IV.

The ketal-containing version of Formula IV comprises the following structure:

(Formula IVb)

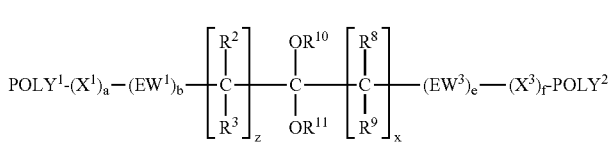

wherein POLY$^1$, POLY$^2$, (a), (b), (e), (f), (z), (x), X$^1$, EW$^1$, EW$^3$, and X$^3$ are as previously defined with respect to Formula IV, and further wherein R$^{10}$ is a organic radical (preferably nonaromatic), R$^{11}$ is an organic radical (preferably nonaromatic), or R$^{10}$ and R$^{11}$ combine to form a cyclic ketal (preferably nonaromatic, e.g., an alkylene such as an ethylene or substituted ethylene).

Exemplary polymeric reagents of Formula IV wherein the functional group is a ketone hydrate comprise the following structure:

(Formula IVc)

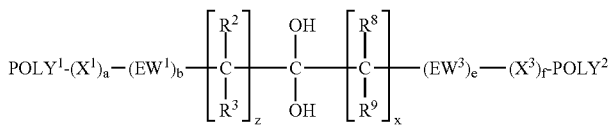

wherein POLY$^1$, POLY$^2$, (a), (b), (e), (f), (z), (x), X$^1$, EW$^1$, EW$^3$, and X$^3$ are as previously defined.

As is evident from the polymeric reagents of Formulas IV, IVa, IVb, and IVc, the functional group carbon serves as the branching point through which each of two water-soluble polymer segments is ultimately attached. In this way, the polymeric reagent has a form resembling the letter "V" or a flattened form thereof. Each water-soluble polymer segment can also be further branched, thereby providing a polymeric reagent with four or more water-soluble polymer segments.

The functional group carbon of a branched polymeric reagent can also be a part of a more complex moiety, as shown below:

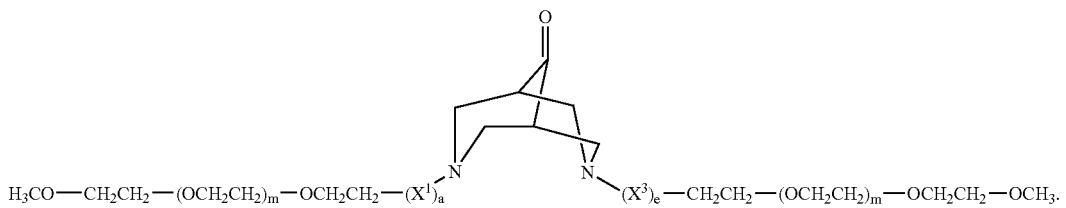

wherein (m) is from about 3 to about 3000, (a) is either zero or one, (e) is either zero or one, X$^1$ is a spacer moiety when present, and X$^3$ is a spacer moiety when present. Diaza cyclic structures other than the 3,7-diaza-bicyclo[3.3.1]nonan-9-one shown above can also provide a moiety suitable for branching.

In some instances of the branched polymeric reagent forms of the present invention, a moiety other than the functional group carbon serves as the branching moiety. In such a case, however, the branching moiety must provide at least three attachment sites, one attachment site providing a linkage (either directly or through one or more atoms) to each of the functional group, the first water-soluble polymer segment, and the second water-soluble polymer segment.

A preferred branching moiety to provide branched polymeric reagents of the invention comprises the following structure

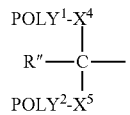

wherein each of POLY$^1$ and POLY$^2$ is a water-soluble polymer segment (either the same or different), R" is a nonreactive moiety, such as H, methyl, or a water-soluble polymer segment; and each of X$^4$ and X$^5$ is a spacer moiety (either the same or different).

Preferred branched moieties are selected from the group consisting of

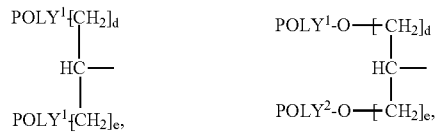

-continued

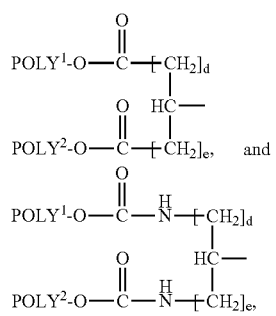

wherein, in each instance, POLY¹ and POLY² are as previously defined, (d) is zero, 1, 2, or 3, and (e) is zero, 1, 2, or 3.

An example of a branched structure of this type is comprised of the following structure:

(Formula V)

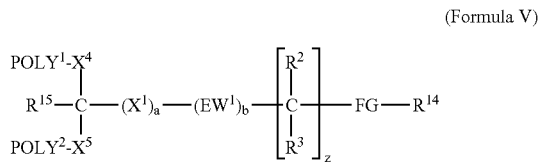

wherein:
POLY¹ is the first water-soluble polymer segment;
POLY² is the second water-soluble polymer segment;
(a) is either zero or one;
(b) is either zero or one;
$X^1$, when present, is a spacer moiety;
$X^4$ is a spacer moiety;
$X^5$ is a spacer-moiety;
$EW^1$, when present, is an electron-withdrawing group;
(z) is zero or a positive integer from 1 to 7;
each occurrence of $R^2$, when present, is independently H or an organic radical;
each occurrence of $R^3$, when present, is independently H or an organic radical;
$R^{15}$ is H or a noninterfering organic radical; and
FG-$R^{14}$ is either (i) a functional group selected from the group consisting of ketone, ketone hydrate, thione, monothiohydrate, dithiohydrate, hemiketal, monothiohemiketal, dithiohemiketal, ketal, and dithioketal having a terminus defined as $R^{14}$, wherein $R^{14}$ is an organic radical, or (ii) a cyclic structure wherein a functional group selected from the group consisting of ketone, ketone hydrate, thione, monothiohydrate, dithiohydrate, hemiketal, monothiohemiketal, dithiohemiketal, ketal, and dithioketal is part of the cyclic structure.

In some instances, FG-$R^{14}$ represents a functional group selected from the group consisting of ketone, ketone hydrate, thione, monothiohydrate, dithiohydrate, hemiketal, monothiohemiketal, dithiohemiketal, ketal, and dithioketal having a terminus defined as $R^{14}$, wherein $R^{14}$ is an organic radical. Thus, exemplary forms of FG-$R^{14}$ (as well as FG-$R^1$ and FG-$R^6$) include

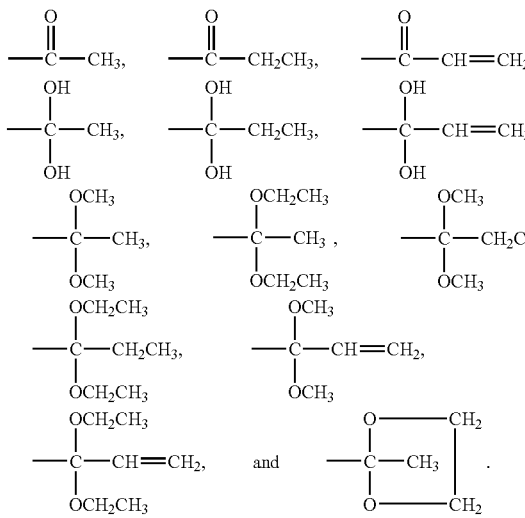

In other instances, FG-$R^{14}$ represents a cyclic structure wherein a functional group selected from the group consisting of ketone, ketone hydrate, thione, monothiohydrate, dithiohydrate, hemiketal, monothiohemiketal, dithiohemiketal, ketal, and dithioketal is part of the cyclic structure.

Exemplary polymeric reagents wherein the cyclic structure is a piperidonyl structure comprise the following:

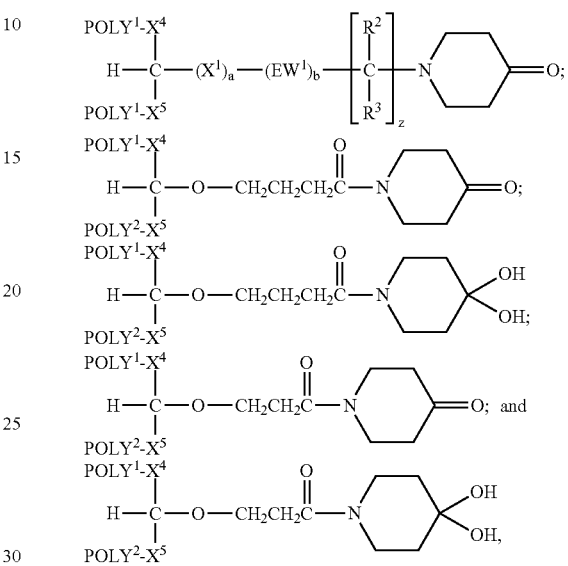

wherein in each instance, POLY¹, POLY², $R^2$, $R^3$, $X^1$, $X^4$, $X^5$, (a), $EW^1$, and (b) are as previously defined with respect to Formula V.

Exemplary branched polymers suitable for use as a water-soluble polymer segment herein are described in U.S. Pat. No. 5,932,462 and are based on a disubstituted lysine residue. Two specific examples of lysine-based branched polymers include an ester-containing version:

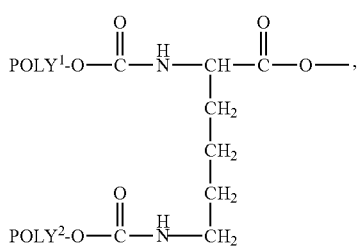

an amide-containing version:

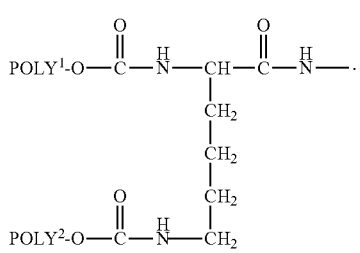

Thus, for example, polymeric reagents encompassed by the following structure result by substituting PEG for each of POLY¹ and POLY² and using the amide-containing, lysine-based branched structure as the branching moiety with respect to Formula V:

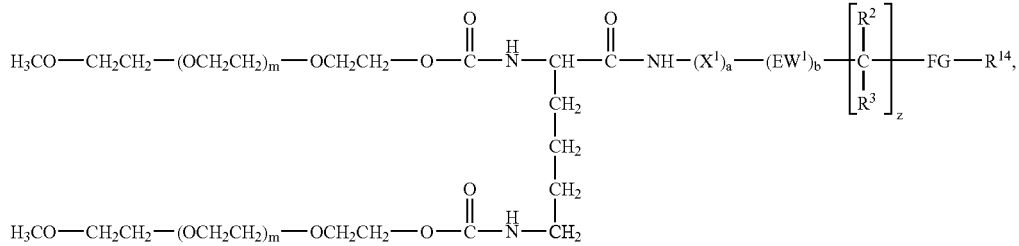

wherein each of (a), (b), (z), $X^1$, $EW^1$, $R^2$, $R^3$, $R^{14}$, FG, is as previously defined with respect to Formula V, and (m) is from 3 to about 3,000.

In addition, polymeric reagents encompassed by the following structure result by substituting PEG for each of POLY¹ and POLY² and using the amide-containing, lysine-based branched structure as the branching moiety with respect to Formula IV:

polymer. Thus, for example, a polymeric reagent comprising two water-soluble polymer segments wherein each segment has a nominal average molecular weight of about 5,000 Daltons will have a total molecular weight of about 10,000 Daltons.

In the context of delivering a conjugate formed from a polymeric derivative comprised of two or more water-soluble segments, individual water-soluble polymer segments can be cleaved in vivo. As one or more water-soluble polymer segments are cleaved from the conjugate, the smaller size of the resulting conjugate often results in improved clearance of the

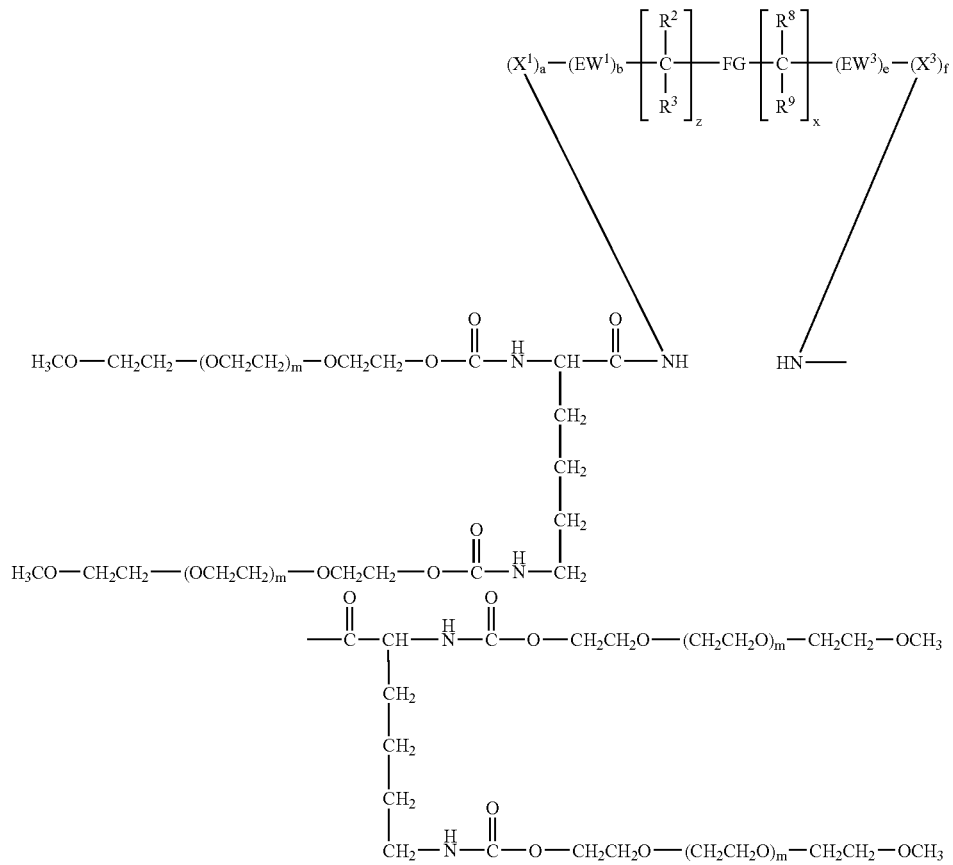

wherein each of $R^2$, $R^3$, $R^8$, $R^9$, (a), (b), (e), (f), (z), (x), $X^1$, $EW^1$, FG, $EW^3$, and $X^3$ are as previously defined, and (m) is from 3 to about 3000.

Polymeric reagents comprising two or more water-soluble polymer segments advantageously provide higher molecular weight species without having to use a relatively long single conjugate from the body. By selecting the molecular weight (i.e., size) of the water-soluble polymer segment and/or cleavable linkage in the polymeric reagent, it is possible to modulate the clearance profile of a conjugate. One of ordinary skill in the art can determine the proper molecular weight of the water-soluble polymer segment as well as the cleavable linkage based on routine experimentation by, for example, preparing a variety of polymeric reagents with different water-soluble polymer segments weights and cleavable linkages, conjugating each of the polymeric reagents with an active agent, administering each of the conjugates to a patient, and then obtaining the clearance profile (e.g., through periodic blood or urine sampling). Thereafter, it is possible to determine which polymeric reagent (based on the corresponding conjugate) provides the desired clearance profile.

The polymeric reagents can also take other forms. For example, the polymeric reagent can be comprised of a functional group attached, either through a direct covalent bond or through one or more atoms, to a water-soluble polymer segment, wherein: (a) the functional group is selected from the group consisting ketone, ketone hydrate, thione, monothiohydrate, dithiohydrate, hemiketal, monothiohemiketal, dithiohemiketal, ketal, and dithioketal of thione, monothiohydrate, dithiohydrate, monothiohemiketal, dithiohemiketal, and dithioketal, and (b) the polymeric reagent lacks saturated hydrocarbon segments having 8 carbon atoms or more. It is preferred, that the functional group is selected from the group consisting of thione, monothiohydrate, dithiohydrate, monothiohemiketal, dithiohemiketal, and dithioketal.

The polymeric reagents of the invention can be provided in the form of a composition. Typically a composition comprises two or more of the same or different polymeric reagents in addition to one or more optional components. While it may be impossible in some contexts to remove all undesirable components of a composition, it is preferred that the compositions of the polymeric reagents described herein are free or substantially free of undesirable components. Examples of undesirable components will be known to those of ordinary skill and are often dependent upon the intended uses of the composition and/or polymeric reagent. Specific examples, however, typically include impurities, components that would cause harm (i.e., be toxic) if administered to a patient, unreacted materials remaining from previous synthetic steps, and so forth.

Preferably, the composition will be substantially free or, more preferably, entirely free of oxidation side products. Compositions can often be rendered substantially free or entirely free of oxidation side products by purifying a composition through, for example, chromatography, to remove any undesired oxidation side products. Another approach is to provide the polymeric reagent and any other components comprising the composition without using an oxidation step. In addition, care must be taken not to allow atmospheric oxygen to react with the composition or any of its components, thereby allowing for the creation of oxidation side products in the composition. In the present context, a composition that is substantially free of oxidation side products is at least 75% (by weight) free of oxidation side products, more preferably at least 85% (by weight) free of oxidation side products, still more preferably at least 90% (by weight) free of oxidation side products, yet more preferably at least 95% free of oxidation side products, even more preferably at least 98% (by weight) of oxidation side products, with at least 99.9% (by weight) free of oxidation side products being most preferred.

Among other problems, oxidation side products can render a polymeric-reagent composition unsuited for use as a reagent in a conjugation reaction. For example, an oxidation side product can be a cleaved portion of a water-soluble polymer segment such as PEG, which can occur when a water-soluble polymer segment has been exposed to oxidizing conditions. In addition, an oxidation side product can be an oxidizing agent itself, which was not completely removed following a synthetic step. The agent can continue to oxidize the products of the composition, thereby initiating undesired chain cleavage of the water-soluble polymer segment. Thus, oxidation side products are preferably absent from the compositions described herein.

Thus, the invention also encompasses compositions comprising a polymeric reagent comprised of a functional group attached, either through a direct covalent bond or through one or more atoms, to a water-soluble polymer segment, wherein the composition is substantially free of oxidation side products.

An example of a polymeric reagent that can (although not necessarily) be a component of a composition that is substantially free of oxidation side products is comprised of the following structure:

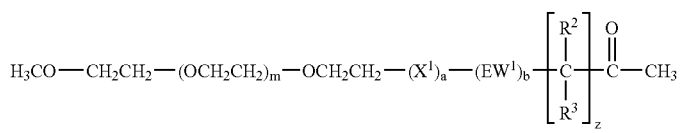

(Formula VI)

wherein:
(a) is either zero or one;
(b) is either zero or one;
$X^1$, when present, is a spacer moiety;
$EW^1$, when present, is an electron-withdrawing group;
(z) is from 1 to 7;
each occurrence of $R^2$ is independently H or a nonaromatic-containing organic radical;
each occurrence of $R^3$ is independently H or a nonaromatic-containing organic radical; and
(m) is from 3 to about 3000, more preferably from 11 to about 3000,
wherein the composition is substantially free of oxidation side products, β-keto esters,

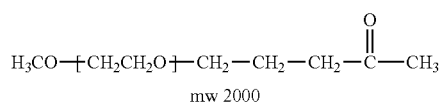

and a ketal derivative of

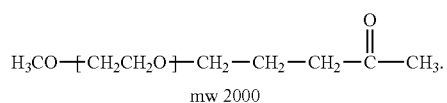

The functional groups other than ketone discussed herein, (i.e., ketone hydrate, thione, monothiohydrate, dithiohydrate, hemiketal, monothiohemiketal, dithiohemiketal, ketal, and dithioketal) can be substituted for the ketone functional group in Formula VI.

III. Methods for Making Polymeric Reagents

Before discussing the various methods for making polymeric reagents, it must be pointed out that the methods, at times, rely on the use of a protected form of a functional group. Some functional groups, such as ketals, may not require protecting. Moreover, some functional groups serve as a protected form for another functional group associated with the presently described polymeric reagent (e.g., ketals often serve as a protected form for ketones). Those of ordinary skill in the art know suitable protecting forms for each of the functional groups associated with the presently described polymeric reagents. For example, protected forms of a ketone include ketals (either cyclic or of a diether type). A ketal can be formed by reacting a ketone with an alcohol, diol, thiol, or dithiol in the presence of an acid catalyst. The ketal so formed (as well as other ketals) can be transformed into a ketone by acid hydrolysis. Other protected forms, as well as protecting and deprotecting the various functional groups discussed herein, are provided in Greene et al. supra.

The various steps for making a polymeric reagent are carried out in a suitable solvent. One of ordinary skill in the art can determine whether any specific solvent is appropriate for any given reaction step. Often, however, the solvent is preferably a nonpolar solvent or a polar aprotic solvent. Nonlimiting examples of nonpolar solvents include benzene, xylene, dioxane, tetrahydrofuran (THF), t-butyl alcohol and toluene. Particularly preferred nonpolar solvents include toluene, xylene, dioxane, tetrahydrofuran, and t-butyl alcohol. Exemplary polar aprotic solvents include, but are not limited to, DMSO (dimethyl sulfoxide), HMPA (hexamethylphosphoramide), DMF (dimethylformamide), DMA (dimethylacetamide), and NMP (N-methylpyrrolidinone).

The polymeric reagents of the invention can be synthesized using a variety of routes. It should be noted that common techniques discussed with respect to one method often apply to similar techniques discussed in other methods. Consequently, discussion of any specific technique for a given method is not limited to that method and therefore applies to each method utilizing that technique.

In some routes, the polymeric reagent is formed via a polymerization approach. Thus, for example, a polymeric reagent can be formed by a method comprising the steps of:

(i) providing a precursor molecule comprised of at least one active anionic site suitable for initiating polymerization and a functional group or a protected form thereof, wherein the functional group is selected from the group consisting of ketone, ketone hydrate, thione, monothiohydrate, dithiohydrate, hemiketal, monothiohemiketal, dithiohemiketal, ketal, and dithioketal;

(ii) contacting the anionic site of the precursor molecule with a reactive monomer capable of polymerizing, to thereby initiate polymerization of the reactive monomer onto the precursor molecule;

(iii) adding additional reactive monomers to the precursor molecule to form one or more polymer chains;

(iv) allowing said adding to continue until a desired length of the one or more polymer chains is reached;

(v) terminating the reaction, thereby resulting in a polymeric reagent comprised of the functional group or protected form thereof; and (vi) optionally, when the functional group is in the protected form, deprotecting the functional group.

The anionic site serves as an initiator site for polymerization and is typically, although not necessarily, an alkoxide moiety. Alkoxide moieties are advantageously obtained by subjecting the corresponding alcohol to a deprotonating base, thereby removing the hydrogen atom from the alcohol to yield the desired alkoxide moiety.

In order to form a polymeric reagent corresponding to Formula IV, a precursor molecule comprising the following structure can be used:

(Formula VIIa)

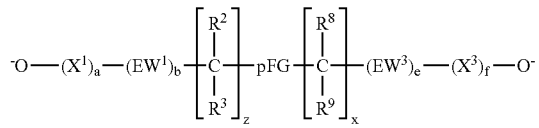

wherein (a), (b), (e), (f), (x), (z), $EW^1$, $EW^3$, $R^2$, $R^3$, $R^8$, and $R^9$ are as previously defined with respect to Formula IV, and further wherein pFG is a functional group or a protected form thereof, wherein the functional group is selected from the group consisting of ketone, ketone hydrate, thione, monothiohydrate, dithiohydrate, hemiketal, monothiohemiketal, dithiohemiketal, ketal, and dithioketal.

Polymeric reagents corresponding to Formula I can be formed through a method comprising this approach wherein the precursor molecule comprises the following structure:

(Formula VIIb)

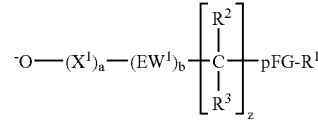

wherein (a), (b), (z), $EW^1$, $R^1$, $R^2$, and $R^3$, are as previously defined with respect to Formula I (in the Summary of the Invention Section), and further wherein pFG is a functional group or a protected form thereof, wherein the functional group is selected from the group consisting of ketone, ketone hydrate, thione, monothiohydrate, dithiohydrate, hemiketal, monothiohemiketal, dithiohemiketal, ketal, and dithioketal.

If the diol corresponding to Formula VIIa is used or the alcohol corresponding to Formula VIIb is used (wherein a hydrogen atom is attached to each alkoxide moiety), an added step of removing the hydrogen (by, for example, treating the alcohol with a deprotonating base) is required in order to yield the alkoxide initiator sites. In addition, thiolates (i.e., —S⁻) can be used in the place of alkoxide moieties. In such a case then, the corresponding thiol or dithiol can be placed in a based to provide the necessary ionic site suited for polymerization.

Specific molecules suited for use as precursor molecules in this approach include the following:

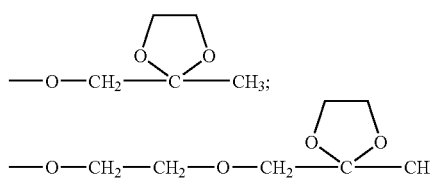

-continued

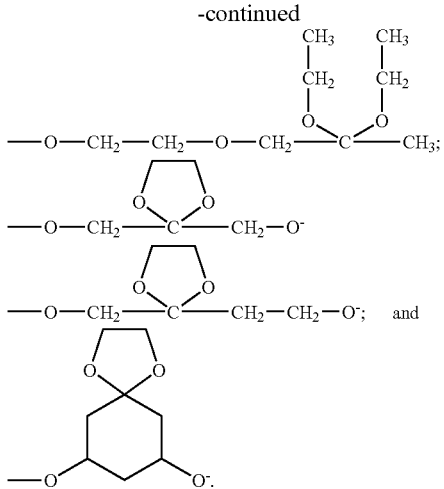

These and other molecules suited for use as precursor molecules can be obtained commercially (either as shown above or in their corresponding alcohol forms) and/or may be synthesized using conventional techniques.

Having provided a precursor molecule with an initiator site (e.g., an anionic site) suited for polymerization, the next step in this approach comprises the step of contacting the initiator site of the precursor molecule with a reactive monomer capable of polymerizing, to thereby initiate polymerization of the reactive monomer onto the precursor molecule. Any reactive monomer can be used to "grow" the polymer chain(s) so long as the resulting polymer chain is water soluble. It is particularly preferred, however, that the reactive monomer is ethylene oxide, thereby providing poly(ethylene oxide) chain(s). These and other polymerization techniques are known to those of ordinary skill in the art and are referenced in, for example, Odian, Chap. 7, Principles of Polymerization, $3^{rd}$ Ed., McGraw-Hill, 1991.

Once polymerization is initiated, additional reactive monomers are added to the precursor molecule to form one or more polymer chains. The addition of the reactive monomers effectively allows the one or more polymer chains to "grow." Growth of the polymer chain(s) continues until a desired molecular weight is achieved, at which time the reaction is terminated. Termination can occur through any of a number of art known methods. For example, neutralizing the reaction medium will halt the growth of the polymer chain(s). In addition, adding a specific weight or amount of the reactive monomer and allowing the polymerization to proceed until all reactive monomer is exhausted results in a polymer chain having a certain and determinable molecular weight. The result is a polymeric reagent comprising a functional group or protected form thereof.

Optionally and prior to carrying out an end-capping step, an electrophilically reactive polymer (either hydrophobic or hydrophilic) can be added to the polymer chain(s).

An added benefit of the ethoxylation route is that it allows for capping the living polymer end (i.e., the terminal of the polymer where additional monomers can be added) with various moieties including other polymers. This allows for the generation of polymers with different properties. Thus, it is possible to cap the already formed water-soluble polymer segment with a hydrophobic polymer and generate a final polymer having hydrophilic and hydrophobic regions. More importantly for many applications, it is possible to add an electrophilically reactive PEG derivative, thereby providing chain extension while, at the same time, adding a hydrolytically cleavable unit. The latter point is important with drug delivery of active agents, such as pharmacologically active proteins, which may have undesirable clearance profiles from the body. A generalized example of this chain extending capping comprises reacting a monosubstituted PEG derivative that gives a carbonate, urethane or similar functional group linkage with the living polymer. Attachment of the polymer, however, must not result in a polymer conjugate that is neither water-soluble nor immunogenic.

Having formed the water-soluble polymer segments in the polymeric reagent, an end-capping group optionally can be added using conventional techniques. For example, an alkyl halide (e.g., methyl halide or methyl p-toluenesulfonate) can be reacted with the exposed terminal (the terminal or termini distal to the functional group or protected form thereof) of the polymer chain. In addition, the one or more polymer chains can be capped with an additional polymer.

Optionally, when the polymeric reagent bears a protected form a functional group, the functional group can be removed using art known methods. For example, a ketal moiety (either cyclic or a diether type) can be removed by undergoing hydrolysis. Again, reference is made to Greene et al. supra for methods of removing other protecting groups.

An advantage of this ethoxylation-based approach for providing polymeric reagents having a central functional group a water-soluble polymer segment on each side of the functional group is the flexibility of molecular weight control and in the capping step. For example, one may polymerize to give a living polymer with an average molecular weight of 5,000 Daltons and cap the hydroxy end groups by adding a methylating reagent. This gives a polymer with a molecular weight of about 5,000 Daltons that has stable (relatively unreactive) end groups but with a functional moiety roughly in the center of the polymer derivative. In addition, one may cap the living polymer with chain extenders to give a higher molecular weight or with functionally reactive ether groups, such as benzyl to give a removable group that could lead to the potential of chemical modification of the end groups.

Another polymerization-based approach for making polymeric reagents involves the use of a protected secondary alcohol. In particular, this approach the method comprises the steps of (i) providing a precursor molecule comprised of a protected secondary alcohol or thiol and at least one anionic site suitable for initiating polymerization;

(ii) contacting the anionic site of the precursor molecule with a reactive monomer capable of polymerizing, to thereby initiate polymerization of the reactive monomer onto the precursor molecule;

(iii) adding additional reactive monomers to the precursor molecule to form one or more polymer chains;

(iv) allowing said contacting to continue until a desired length of the one or more polymer chains is reached;

(v) terminating the reaction, thereby resulting in an intermediate comprised of the protected secondary alcohol or thiol;

(vi) deprotecting the protected secondary alcohol or thiol of the intermediate to form an unprotected secondary alcohol or thiol;

(vii) oxidizing the unprotected secondary alcohol or thiol to provide a polymeric reagent comprised of a ketone when the precursor molecule comprised a secondary alcohol or a thione when the precursor molecule comprised a secondary thiol; and (viii) optionally further modifying the ketone or thione to result in a functional group selected from the group consisting of ketone, ketone hydrate, thione, monothiohydrate, dithiohydrate, hemiketal, monothiohemiketal, dithiohemiketal, ketal, and dithioketal.

Thus, with respect to steps (ii), (iii), (iv), (v), involving the use of polymerization techniques, the same polymerization techniques discussed above apply equally as well here. As above, the anionic site serves as an initiator site for polymerization and is typically, although not necessarily, an alkoxide moiety. Alkoxide moieties are advantageously obtained by subjecting the corresponding alcohol to a deprotonating base, thereby removing the hydrogen atom from the alcohol to yield the desired alkoxide moiety.

In order to form a branched polymeric reagent of Formula IV using this approach, the precursor molecule will comprise the following structure:

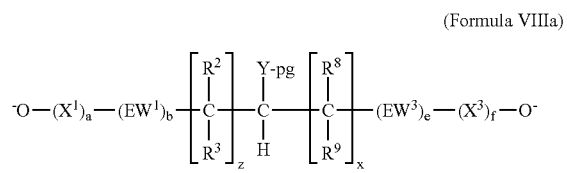

(Formula VIIIa)

wherein (a), (b), (e), (f), (x), (z), $X^1$, $X^3$, $EW^1$, $EW^3$, $R^2$, $R^3$, $R^8$, and $R^9$ are as previously defined with respect to Formula IV, and further wherein Y is oxygen or sulfur and "pg" is a protecting group for a secondary alcohol when Y is oxygen and a protecting group for a secondary thiol when Y is sulfur.

Polymeric reagents corresponding to Formula I can be formed through a method comprising this approach wherein the precursor molecule comprises the following structure:

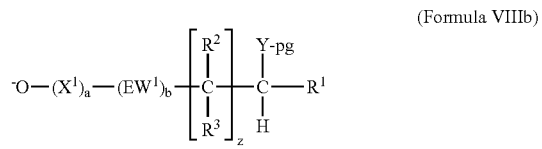

(Formula VIIIb)

wherein (a), (b), (z), $X^1$, $EW^1$, $R^1$, $R^2$, and $R^3$ are as previously defined with respect to Formula I (in the Summary of the Invention Section), and further wherein Y is oxygen or sulfur and "pg" is a protecting group for a secondary alcohol when Y is oxygen and a protecting group for a secondary thiol when Y is sulfur.

As previously indicated, the precursor molecule comprises a protected secondary alcohol or thiol. Any suitable, art-known protecting group suitable for protecting a secondary alcohol or thiol can be used, and include, for example, benzyl ether, methyoxymethyl ether (MOM), methylthiomethyl ether (MTM), tetrahydropyranyl ether (THP), 4-methoxytetrahydropyranyl ether, tetrahydrofuranyl ether, 1-ethoxyethyl ether, 1-methyl-1-methoxyethyl ether, 2-(phenylselenyl) ethyl ether, allyl ether, o-nitrobenzyl ether, triphenylmethyl ether, α-naphthyldiphenylmethyl ether, p-methyoxyphenyl-diphenylmethyl ether, 9-(9-phenyl-10-oxo)anthryl ether (tritylone), isopropyldimethylsilyl ether, t-butyldimethylsilyl ether (TBDMS), tribenzylsilyl ether, and triisopropylsilyl ether. A particularly preferred protecting group for use with the method is benzyl ether.

Specific molecules (in the corresponding alcohol forms) suited for use as precursor molecule in this approach include a monoprotected glycerol having the following formula:

CH$_2$—OH
|
CH—Y-(pg)
|
CH$_2$—OH.:

wherein Y is oxygen or sulfur, "pg" is a protecting group suitable for protecting a secondary alcohol when Y is oxygen or thiol when Y is sulfur.

A particularly preferred monoprotected glycerol is 2-benzyloxy-1,3-propanediol shown below:

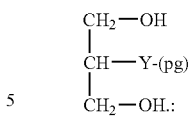

2-benzyloxy-1,3-propanediol

These and other monoprotected glycerols are available from commercial suppliers such as Sigma (St. Louis, Mo.) and/or can be synthesized using conventional techniques.

Having formed the water-soluble polymer segment, along with optionally additionally attaching an electrophilic polymer and optionally alkylating the terminal or termini of the water-soluble polymer segment or segments, the method comprises the step of deprotecting the protected secondary alcohol or thiol to form an unprotected secondary alcohol or thiol. The protecting group can be removed using art known methods. For example, the deprotecting step can be effected by exposing the intermediate to $H_2$ and a metal catalyst such as palladium, palladium oxide, nickel, platinum, or lead.

After the deprotecting step, the method comprises carrying out an oxidizing step, which can be performed in any conventional manner and the invention is not limited in this regard. Examples of suitable oxidizing techniques comprise contacting the intermediate to be oxidized with an oxidizing reagent selected from the group consisting of $KMnO_4$, $MnO_2$, $K_2Cr_2O_7$, $CrO_3$, pyridinium chlorochromate, pyridinium fluorochromate, pyridinium dichromate, $RuO_4$, $RuCl_3$, tetra-n-propylammonium perruthenate, dimethyl sulfoxide, N-chlorosuccinimide, $Ag_2CO_3$, $AG_2O$, and Dess-Martin periodinane reagents.

Other approaches for forming the polymeric reagents of the invention are not based on a polymerization approach. In one nonpolymerization approach for providing a polymeric reagent of the invention, the method comprises the steps of (i) providing a precursor molecule comprised of at least one isocyanate moiety and a functional group or a protected form thereof, wherein the functional group is selected from the group consisting of ketone, ketone hydrate, thione, monothiohydrate, dithiohydrate, hemiketal, monothiohemiketal, dithiohemiketal, ketal, and dithioketal; and (ii) contacting, under suitable reaction conditions, the precursor molecule and a water-soluble polymer segment bearing at least one hydroxyl or amine group to thereby form a polymeric reagent comprising the functional group or protected form thereof; and (iii) optionally, when the functional group is in the protected form, deprotecting the functional group.

In this third approach, a number of precursor molecules comprising at least one isocyanate moiety can a functional group or protected form thereof can be used.

In order to form a branched polymeric reagent of Formula IV using this approach, the reaction will comprise contacting:
(a) a precursor molecule comprised of the following structure:

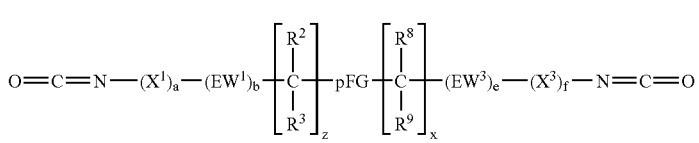
(Formula IXa)

wherein (a), (b), (e), (f), (x), (z), $X^1$, $X^3$, $EW^1$, $EW^3$, $R^2$, $R^3$, $R^8$, and $R^9$ are as previously defined with respect to Formula IV and further wherein pFG is a functional group or a protected form thereof, wherein the functional group is selected from the group consisting of ketone, ketone hydrate, thione, monothiohydrate, dithiohydrate, hemiketal, monothiohemiketal, dithiohemiketal, ketal, and dithioketal; with (b) a water-soluble polymer segment bearing one terminal hydroxyl group.

The water-soluble polymer segment will be added in at least a 2:1 molar to the isocyanate precursor molecule. It is preferred, however that an excess of the water-soluble polymer segment is present.

In order to form a polymeric reagent of Formula I using this approach, the reaction comprises contacting: (a) a precursor molecule comprised of the following structure:

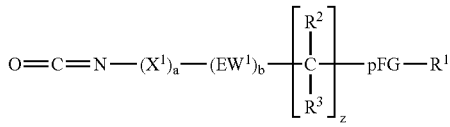
(Formula IXb)

wherein (a), (b), (z), $X^1$, $EW^1$, $R^1$, $R^2$, and $R^3$ are as previously defined with respect to Formula I (in the Summary of the Invention Section), and further wherein pFG is a functional group or a protected form thereof, wherein the functional group is selected from the group consisting of ketone, ketone hydrate, thione, monothiohydrate, dithiohydrate, hemiketal, monothiohemiketal, dithiohemiketal, ketal, and dithioketal; with (b) a water-soluble polymer segment bearing one terminal hydroxyl or amine group.

The water-soluble polymer segment will be added in at least a 1:1 molar ratio of water-soluble polymeric reagent to isocyanate precursor molecule. It is preferred, however that an excess of the isocyanate precursor molecule is present.

In order to form a homobifunctional polymeric reagent, the reaction will comprise contacting: (a) a precursor molecule of Formula IXb; with (b) a water-soluble polymer segment bearing two terminal hydroxyl groups. The water-soluble polymer segment is typically in no more than a 1:2 molar ratio to isocyanate precursor molecule.

In a fourth approach for preparing a polymeric reagent, a method is provided comprising the steps of (i) providing a water-soluble polymer segment having at least one available nucleophilic group; (ii) providing a precursor molecule comprised of at least one activating group and a functional group or a protected form thereof, wherein the functional group is selected from the group consisting of ketone, ketone hydrate, thione, monothiohydrate, dithiohydrate, hemiketal, monothiohemiketal, dithiohemiketal, ketal, and dithioketal; (iii) contacting, under suitable reaction conditions, the precursor molecule with the water-soluble polymer segment, thereby forming a polymeric reagent comprising the functional group or protected form thereof; and (iv) optionally, when the functional group is in the protected form, deprotecting the functional group.

The water-soluble polymer segment having at least one available nucleophilic group can be any polymer terminating in a nucleophilic group. Such polymers include, without limitation: polymers bearing a terminal amine (e.g., amine-terminated PEG, available from, for example, Nektar Therapeutics, Huntsville, Ala.). The activating group of the precursor molecule can be any suitable activating group as that term is understood by those of ordinary skill in the art, but an activating group selected from the group consisting of halide (e.g., fluoride, chloride, iodide), sulfonate esters (e.g., methansulfonate, p-toluenesulfonate, and so forth), and N-succinimidyl is preferred.

Branched polymeric reagents of Formula IV can be formed using this approach by contacting a water-soluble polymer segment having at least one available nucleophilic group; with a precursor molecule comprised of the following structure:

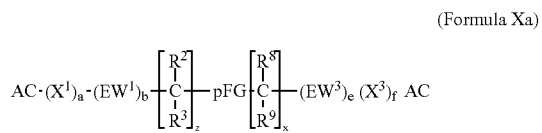
(Formula Xa)

wherein (a), (b), (e), (f), (x), (z), $X^1$, $X^3$, $EW^1$, $EW^3$, $R^2$, $R^3$, $R^8$, and $R^9$ are as previously defined with respect to Formula IV, and further wherein each AC is an activating group and pFG is a functional group or a protected form thereof, wherein the functional group is selected from the group consisting of ketone, ketone hydrate, thione, monothiohydrate, dithiohydrate, hemiketal, monothiohemiketal, dithiohemiketal, ketal, and dithioketal.

The water-soluble polymer segment is added in at least a 2:1 molar ratio to the precursor molecule. Preferably, however, an excess of the water-soluble polymer segment is added.

Polymeric reagents of Formula I can also be prepared using this approach. Thus, a water-soluble polymer segment having at least one available nucleophilic group is contacted with a precursor molecule comprised of the following structure:

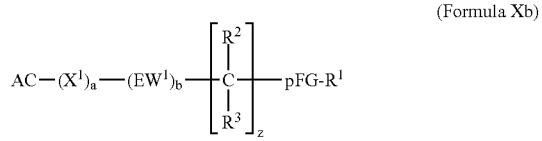
(Formula Xb)

wherein (a), (b), (z), $X^1$, $EW^1$, $R^1$, $R^2$, and $R^3$ are as previously defined with respect to Formula I (in the Summary of the Invention Section), and further wherein AC is an activating group and pFG is a functional group or a protected form thereof, wherein the functional group is selected from the group consisting of ketone, ketone hydrate, thione, monothiohydrate, dithiohydrate, hemiketal, monothiohemiketal, dithiohemiketal, ketal, and dithioketal. The water-soluble polymer segment having at least one available nucleophilic group is added in amount equaling at least a 1:1 molar ratio of water-soluble polymer segment to the precursor molecule. It is preferred, however, that an excess of the water-soluble segment is present.

A homobifunctional polymeric reagent can also be prepared by reacting a water-soluble polymer segment having at least two available nucleophilic groups with a precursor molecule having a structure corresponding to Formula Xb. In this instance, the molar ratio of water-soluble polymer segment to precursor molecule is typically no more than 1:2, and typically an excess of the precursor molecule is present.

A fifth approach for making a polymeric reagent comprises the steps of:

(i) providing a water-soluble polymer segment having at least one available leaving group;

(ii) providing a precursor molecule comprised of at least one nucleophilic group and a functional group or a protected form thereof, wherein the functional group is selected from the group consisting of ketone, ketone hydrate, thione, monothiohydrate, dithiohydrate, hemiketal, monothiohemiketal, dithiohemiketal, ketal, and dithioketal;

(iii) contacting, under suitable reaction conditions, the precursor molecule with the water-soluble polymer segment, thereby forming a polymeric reagent comprising the functional group or protected form thereof; and (iv) optionally, when the functional group is in the protected form, deprotecting the functional group.

Preferred leaving groups on the water-soluble polymer segment include those that are primary (e.g., a primary halo), although leaving groups that are secondary may also be used. Examples of suitable leaving groups include halogens and sulfonate esters. Among the halogens, bromo, chloro, and iodo are preferred, with bromo and chloro being particularly preferred. With respect to sulfonate esters, methanesulfonate (abbreviated "Ms"), trifluoromethanesulfonate, trichloromethanesulfonate, 2,2,2-trifluoroethanesulfonate, 2,2,2-trichloroethanesulfonate, nonafluorobutanesulfonate, p-bromobenzenesulfonate, p-nitrobenzenesulfonate, and p-toluenesulfonate are particularly preferred, although other sulfonate esters and similarly constituted leaving groups known to those of ordinary skill in the art can be used as well.

With respect to the precursor molecule bearing, among other things, a nucleophilic group, the nucleophilic group can be any suitable nucleophilic group that can react with the leaving group(s) associated with water-soluble polymer segment. Typically, the nucleophilic group is alkoxide (R—O⁻) or thiolate (R—S⁻), derived from removing the hydrogen from the corresponding alcohol or thiol forms, respectively. Thus, precursor molecules comprising structures corresponding to Formulas VIIa and VIIb can be used. As previously indicated, specific examples of alkoxide moieties include the following:

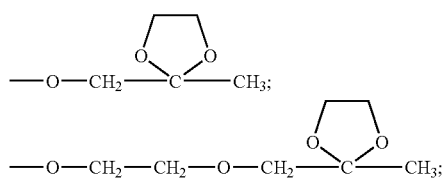

-continued

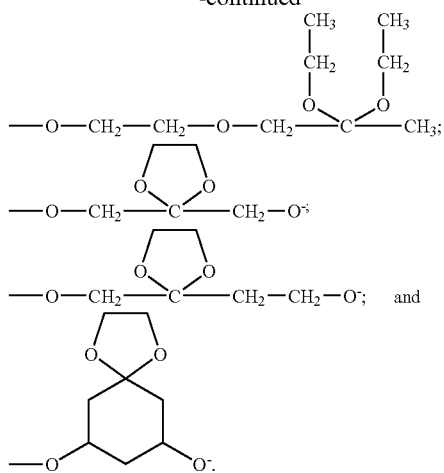

In a sixth approach for providing a polymeric reagent of the invention, a method is provided comprising the step of reacting a water-soluble polymer segment having at least one alkoxide ion or thiolate ion with a precursor molecule comprised of at least one leaving group and a functional group or a protected form thereof, wherein the functional group is selected from the group consisting of ketone, ketone hydrate, thione, monothiohydrate, dithiohydrate, hemiketal, monothiohemiketal, dithiohemiketal, ketal, and dithioketal, thereby providing a polymeric reagent.

Conveniently, the water-soluble polymer segment having at least one alkoxide or thiolate ion is prepared by combining a water-soluble polymer segment having at least one hydroxyl or thiol group in the presence of a suitable base. Thus, the base transforms POLY-OH into POLY-O⁻ and POLY-SH into POLY-S⁻. It is further believed that the water-soluble polymer, now bearing an alkoxide or thiolate moiety, in turn reacts via a $S_N2$ reaction mechanism with the precursor molecule comprised of a suitable leaving group. As will be recognized by those of ordinary skill in the art, this approach corresponds to Williamson ether synthesis, and the principles and techniques generally used in a Williamson ether synthesis are applicable here as well.

Nonlimiting examples of bases suitable to form alkoxides and thiolates include sodium, sodium hydroxide, potassium, potassium hydroxide, sodium hydride, potassium hydride, sodium methoxide, potassium methoxide, sodium tert-butoxide, potassium tert-butoxide, sodium carbonate, and potassium carbonate. Preferred bases for use in accordance with this step, however, include those selected from the group consisting of sodium, potassium, sodium hydride, potassium hydride, sodium methoxide, potassium methoxide, sodium tert-butoxide, and potassium tert-butoxide.

In addition, the water-soluble polymer segment having at least one alkoxide or thiolate ion can conveniently be provided via a polymerization reaction, as previously described. In this approach for providing the water-soluble polymer segment, it is preferred that the water-soluble polymer segment has at least one alkoxide or thiolate ion.

Generally, although not necessarily, an excess of the precursor molecule is allowed to react with the water-soluble polymer bearing at least one alkoxide or thiolate ion. Typically, the amount of the precursor molecule represents at least a molar equivalent to the number available hydroxyl and/or thiolate groups of the water-soluble polymer molecule. Heterofunctional polymer species (i.e., species bearing two or more different terminal functional groups) can be prepared by using nonstoichiometric amounts of the precursor molecule. That is, heterofunctional species are formed when the total number of moles of available hydroxyl or thiolate groups on the water-soluble polymer segment exceeds the total number of moles of the precursor molecule.

A water-soluble polymer segment bearing an alkoxide moiety can be prepared synthetically via a polymerization process. For example, an alkoxide salt such as sodium 2-methoxy ethanolate ($Na^+$:$^-OCH_2CH_2OCH_3$) can initiate polymerization of ethylene oxide. Assuming that the final monomer added to the polymer chain leaves a reactive group such as an alkoxide (as in the case of ethylene oxide), the polymer chain can then be reacted with the precursor molecule as discussed above.

Any water-soluble polymer having at least one hydroxyl or thiol group (to provide, for example, a water-soluble polymer having at least one alkoxide ion or thiolate ion, respectively) can be used. Although water-soluble polymers bearing only a single hydroxyl or thiol can be used, polymers bearing two, three, four, five, six, seven, eight, nine, ten, eleven, twelve or more hydroxyl and/or thiol moieties can be used. Advantageously, as the number of hydroxyl or thiol moieties on the water-polymer segment increases, the number of available sites for providing ketone, ketone hydrate, thione, monothiohydrate, dithiohydrate, hemiketal, monothiohemiketal, dithiohemiketal, ketal, and dithioketal moieties increases. Nonlimiting examples of the upper limit of the number of hydroxyl and/or thiol moieties associated with the water-soluble polymer segment include 500, 100, 80 and 40.

IV. Conjugates

The polymeric reagents described herein are useful for conjugation to biologically active agents or surfaces. Exemplary groups suited for reaction with the polymeric reagents described herein are primary amine groups (e.g., primary amines from the side chain of a lysine residue), alcohols (e.g., a primary alcohol from the side chain of a serine or threonine residue), hydrazines, and hydrazides. Additional functional groups are reactive with ketones (and related functional groups) and can be employed in conjugation reactions when present on another molecule, e.g., active agent. Such groups suited to react with the polymeric reagents described herein are known to those of ordinary skill in the art. Thus, the invention provides a method for making a conjugate comprising the step of contacting, under conjugation conditions, an active agent with a polymeric reagent comprising a functional group selected from the group consisting of ketone, ketone hydrate, thione, monothiohydrate, dithiohydrate, hemiketal, monothiohemiketal, dithiohemiketal, ketal, and dithioketal. Preferred polymeric reagents used in the conjugation reaction include those described herein (e.g., the polymeric reagents of Formulas I, II, III, IV, V, and VI).

Suitable conjugation conditions are those conditions of time, temperature, pH, reagent concentration, reagent functional group(s), available functional groups on the active agent, solvent, and the like sufficient to effect conjugation between a polymeric reagent and an active agent. As is known in the art, the specific conditions depend upon, among other things, the active agent, the type of conjugation desired, the presence of other materials in the reaction mixture, and so forth. Sufficient conditions for effecting conjugation in any particular case can be determined by one of ordinary skill in the art upon a reading of the disclosure herein, reference to the relevant literature, and/or through routine experimentation.

Exemplary conjugation conditions include carrying out the conjugation reaction at a pH of from about 4 to about 10, and at, for example, a pH of about 4.0, 4.5, 5.0, 5.5, 6.0, 6.5, 7.0, 7.5, 8.0, 8.5, 9.0, 9.5, or 10.0. The reaction is allowed to proceed from about 5 minutes to about 72 hours, preferably from about 30 minutes to about 48 hours, and more preferably from about 4 hours to about 24 hours. The temperature under which conjugation can take place is typically, although not necessarily, in the range of from about 0° C. to about 40° C., and is often at room temperature or less. The conjugation reactions are often carried out using a phosphate buffer solution, sodium acetate, or similar system.

With respect to reagent concentration, an excess of the polymeric reagent is typically combined with the active agent. In some cases, however, it is preferred to have stoichiometic amounts of reactive groups on the polymeric reagent to the reactive groups of the active agent. Thus, for example, two moles of a polymeric reagent having two ketone groups are combined for every mole of active agent. Exemplary ratios of polymeric reagent to active agent include molar ratios of about 1:1 (polymeric reagent:active agent), 1.5:1, 2:1, 3:1, 4:1, 5:1, 6:1, 8:1, or 10:1. The conjugation reaction is allowed to proceed until substantially no further conjugation occurs, which can generally be determined by monitoring the progress of the reaction over time.

Progress of the reaction can be monitored by withdrawing aliquots from the reaction mixture at various time points and analyzing the reaction mixture by SDS-PAGE or MALDI-TOF mass spectrometry or any other suitable analytical method. Once a plateau is reached with respect to the amount of conjugate formed or the amount of unconjugated polymer remaining, the reaction is assumed to be complete. Typically, the conjugation reaction takes anywhere from minutes to several hours (e.g., from 5 minutes to 24 hours or more). The resulting product mixture is preferably, but not necessarily purified, to separate out excess polymeric reagent, unconjugated reactants (e.g., active agent), and undesired multi-conjugated species. The resulting conjugates can then be further characterized using analytical methods such as MALDI, capillary electrophoresis, gel electrophoresis, and/or chromatography.

In another embodiment of the invention, a method is provided for preparing a polymer-active agent conjugate. Any conjugating method that employs a functional group selected from the group consisting of ketone, ketone hydrate, thione, monothiohydrate, dithiohydrate, hemiketal, monothiohemiketal, dithiohemiketal, ketal, and dithioketal can be used. A preferred conjugation approach for preparing polymer-active agent conjugates is reductive animation. While not wishing to be bound by theory, the reductive animation approach is believed to comprise nucleophilic addition of an amine-containing active agent to the functional group of a polymeric reagent, wherein the functional group is selected from the group consisting of ketone, ketone hydrate, thione, monothiohydrate, dithiohydrate, hemiketal, monothiohemiketal, dithiohemiketal, ketal, and dithioketal. With respect to reductive animation, preferred functional groups of the polymeric reagent include ketone, ketone hydrate, hemiketal, and ketal. Those of ordinary skill in the art are familiar with reductive animation techniques.

Figure 3:
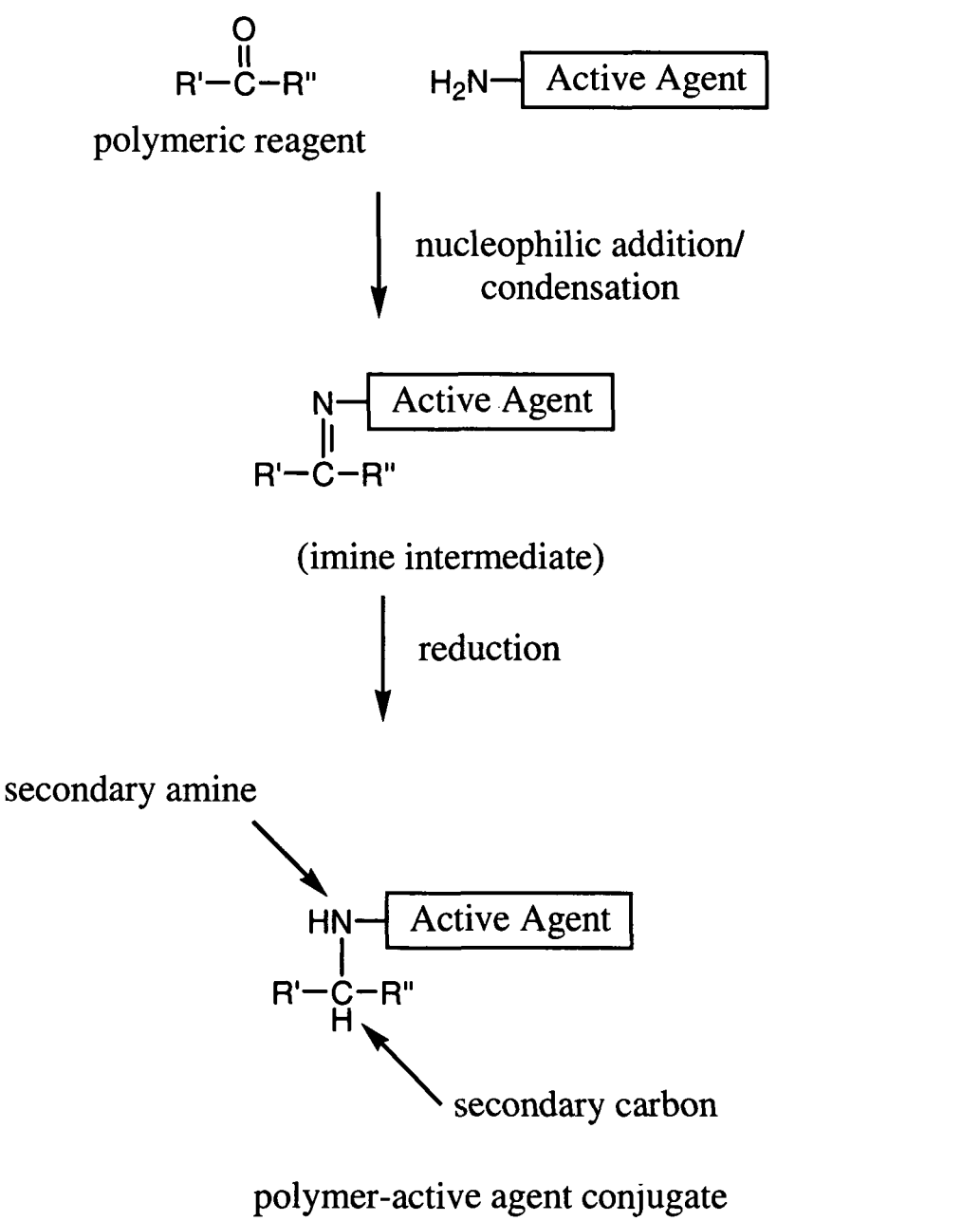
FIG. 3 is a schematic representation of a conjugation method according to the present invention.

Briefly, and without wishing to be bound by theory, an exemplary reductive animation (wherein the active agent bears an amine and the polymeric reagent comprises a ketone) first proceeds via a carbinolamine intermediate. The carbinolamine then dehydrates (condenses) to result in an imine. The imine, in turn, can then be reduced using a suitable reducing agent to form the polymer-active agent conjugate. An exemplary reducing agent is sodium cyano borohydride. In some instances, the reducing agents such as zinc in the presence of HCl, sodium borohydride, iron pentacarbonyl in the presence of alcoholic KOH, hydrogen ($H_2$) in the presence of a metal catalyst, and formic acid can be used. The reaction is schematically depicted in FIG. 3.

Of particular note is the linkage between the active agent and polymeric reagent: the amine of the active agent is attached to a secondary carbon atom of the polymeric reagent. Thus, in another embodiment of the invention, a conjugate is provided comprising a covalent bond between a nitrogen atom of an active agent and a secondary carbon atom derived from the polymeric reagent. A secondary carbon atom is a carbon atom that is directly bonded to two other carbons (represented as R' and R" in FIG. 3). With respect to the remaining part of the conjugate, the secondary carbon atom is attached, either directly or through one or more atoms, to a water-soluble polymer segment. Thus, the secondary carbon atom is attached to a first carbon atom (as in R' in FIG. 3) and a second carbon atom (as in R" in FIG. 3) wherein at least one of the first carbon atom or second carbon atom is attached, either directly or through one or more atoms, to a water-soluble polymer segment.

Depending on the polymeric reagent used to form the conjugate, the atom or atoms attached to the secondary carbon (other than the nitrogen from the active agent), will vary. In some instances, a methyl group is attached to the secondary carbon (i.e., one of the first carbon atom or second carbon atom attached to the secondary carbon atom is methyl). In other instances, a water-soluble polymer segment is attached to each one of the two carbon atoms (i.e., the first carbon atom and second carbon atom attached to the secondary carbon atom) attached to the secondary carbon atom, thereby providing two polymer-containing "arms" connected through the secondary carbon atom. In these instances, the conjugate comprises a second water-soluble polymer segment attached, either directly or though one or more atoms, to the secondary carbon atom. In still other instances, the water-soluble polymeric segment itself may be branched, such when a polymeric reagent shown in Formula V is conjugated to an active agent.

With respect to reductive amination, the conjugates preferably lack a hydroxyl moiety attached to the secondary carbon atom, which can result from direct addition (or "1,2 addition") of a nucleophile to, for example, a carbonyl of an α,β-unsaturated carbonyl. In addition, the conjugates preferably lack a carbonyl attached to a carbon adjacent to the secondary carbon atom (i.e., lacking a carbonyl β to the secondary carbon atom), which can result from conjugate addition (or "1,4 addition").

As shown in FIG. 3, a nitrogen from a primary amine-containing active agent (e.g., the primary amine from a lysine side chain of a protein, the N-terminal amine of a protein, and so forth) was used to form the conjugate. Conjugation via reductive animation can also occur when the active agent comprises a secondary amine. In this case, the resulting conjugate comprises a tertiary amine (derived from the active agent) linked to a secondary carbon (derived from the polymeric reagent).

Other approaches for conjugating the polymeric reagents to active agents can also be used. For example, polymeric reagents having an α,β-unsaturated functional group (e.g., an α,β-unsaturated ketone) can participate in direct addition, wherein a nucleophile (e.g., amine) can react by nucleophilic addition via direct addition (or "1,2 addition") to the functional group. In addition, these polymeric reagents can participate in conjugate addition (or "1,4 addition"), wherein the nucleophile becomes attached to the β carbon, and the α carbon accepts a proton from the solvent or from the conjugate acid of the nucleophile. The structure of the reagent will largely dictate how the reaction will occur. With an α,β-unsaturated ketone on the vinyl carbons and sterically hindered on the other alpha carbon, conjugate addition (1,4-addition) is expected to prevail.

Regardless of the approach used in their formation, the polymer-active agent conjugates can be purified to obtain/isolate different conjugated species. Alternatively, and more preferably for lower molecular weight (e.g., less than about 20,000 Dalton, more preferably less than about 10,000 Dalton) polymeric reagents used to form conjugates, the product mixture can be purified to obtain the distribution of water-soluble polymer segments per active agent. For example, the product mixture can be purified to obtain an average of anywhere from one to five PEGs per active agent (e.g., protein), typically an average of about 3 PEGs per active agent (e.g., protein). The strategy for purification of the final conjugate reaction mixture will depend upon a number of factors, including, for example, the molecular weight of the polymeric reagent employed, the particular active agent, the desired dosing regimen, and the residual activity and in vivo properties of the individual conjugate(s).

If desired, conjugates having different molecular weights can be isolated using gel filtration chromatography. That is to say, gel filtration chromatography is used to fractionate differently numbered polymer-to-active agent ratios (e.g., 1-mer, 2-mer, 3-mer, and so forth, wherein "1-mer" indicates 1 polymeric reagent to active agent, "2-mer" indicates two polymeric reagents to active agent, and so on) on the basis of their differing molecular weights (where the difference corresponds essentially to the average molecular weight of the water-soluble polymer segments). For example, in an exemplary reaction where a 100,000 Dalton protein is randomly conjugated to a ketone-containing PEG having a molecular weight of about 20,000 Daltons, the resulting reaction mixture may contain unmodified protein (having a molecular weight of about 100,000 Daltons), monoPEGylated protein (having a molecular weight of about 120,000 Daltons), diPEGylated protein (having a molecular weight of about 140,000 Daltons), and so forth.

While this approach can be used to separate PEG and other polymer-active agent conjugates having different molecular weights, this approach is generally ineffective for separating positional isomers having different polymer attachment sites within the protein. For example, gel filtration chromatography can be used to separate from each other mixtures of PEG 1-mers, 2-mers, 3-mers, and so forth, although each of the recovered PEG-mer compositions may contain PEGs attached to different reactive amino groups (e.g., lysine residues) within the active agent.

Gel filtration columns suitable for carrying out this type of separation include Superdex™ and Sephadex™ columns available from Amersham Biosciences (Piscataway, N.J.). Selection of a particular column will depend upon the desired fractionation range desired. Elution is generally carried out using a suitable buffer, such as phosphate, acetate, or the like. The collected fractions may be analyzed by a number of different methods, for example, (i) optical density (OD) at 280 nm for protein content, (ii) bovine serum albumin (BSA) protein analysis, (iii) iodine testing for PEG content (Sims et al. (1980) *Anal. Biochem,* 107:60-63), and (iv) sodium dodecyl sulfate polyacrylamide gel electrophoresis (SDS PAGE), followed by staining with barium iodide.

Separation of positional isomers is carried out by reverse phase chromatography using a reverse phase-high performance liquid chromatography (RP-HPLC) C18 column (Amersham Biosciences or Vydac) or by ion exchange chromatography using an ion exchange column, e.g., a Sepharose™ ion exchange column available from Amersham Biosciences. Either approach can be used to separate polymer-active agent isomers having the same molecular weight (positional isomers).

The polymeric reagents described herein can be attached, either covalently or noncovalently, to a number of entities including films, chemical separation and purification surfaces, solid supports, metal surfaces such as gold, titanium, tantalum, niobium, aluminum, steel, and their oxides, silicon oxide, macromolecules (e.g., proteins, polypeptides, and so forth), and small molecules. Additionally, the polymeric reagents can also be used in biochemical sensors, bioelectronic switches, and gates. The polymeric reagents can also be employed as carriers for peptide synthesis, for the preparation of polymer-coated surfaces and polymer grafts, to prepare polymer-ligand conjugates for affinity partitioning, to prepare cross-linked or non-cross-linked hydrogels, and to prepare polymer-cofactor adducts for bioreactors.

A biologically active agent for use in coupling to a polymeric reagent as presented herein may be any one or more of the following. Suitable agents can be selected from, for example, hypnotics and sedatives, psychic energizers, tranquilizers, respiratory drugs, anticonvulsants, muscle relaxants, antiparkinson agents (dopamine antagonists), analgesics, anti-inflammatories, antianxiety drugs (anxiolytics), appetite suppressants, antimigraine agents, muscle contractants, anti-infectives (antibiotics, antivirals, antifungals, vaccines) antiarthritics, antimalarials, antiemetics, anepileptics, bronchodilators, cytokines, growth factors, anti-cancer agents, antithrombotic agents, antihypertensives, cardiovascular drugs, antiarrhythmics, antioxicants, anti-asthma agents, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents.

More particularly, the active agent may fall into one of a number of structural classes, including but not limited to small molecules (preferably insoluble small molecules), peptides, polypeptides, proteins, antibodies, antibody fragments, polysaccharides, steroids, nucleotides, oligonucleotides, polynucleotides, fats, electrolytes, and the like. Preferably, an active agent for coupling to a polymer as described herein possesses a native amino group, or alternatively, is modified to contain at least one reactive amino group suitable for conjugating to a polymer described herein.

Specific examples of active agents suitable for covalent attachment include but are not limited to aspariginase, amdoxovir (DAPD), antide, becaplermin, calcitonins, cyanovirin, denileukin diftitox, erythropoietin (EPO), EPO agonists (e.g., peptides from about 10-40 amino acids in length and comprising a particular core sequence as described in WO 96/40749), dornase alpha, erythropoiesis stimulating protein (NESP), coagulation factors such as Factor V, Factor VII, Factor VIIa, Factor VIII, Factor IX, Factor X, Factor XII, Factor XIII, von Willebrand factor; ceredase, cerezyme, alpha-glucosidase, collagen, cyclosporin, alpha defensins, beta defensins, exedin-4, granulocyte colony stimulating factor (GCSF), thrombopoietin (TPO), alpha-1 proteinase inhibitor, elcatonin, granulocyte macrophage colony stimulating factor (GMCSF), fibrinogen, filgrastim, growth hormones human growth hormone (hGH), growth hormone releasing hormone (GHRH), GRO-beta, GRO-beta antibody, bone morphogenic proteins such as bone morphogenic protein-2, bone morphogenic protein-6, OP-1; acidic fibroblast growth factor, basic fibroblast growth factor, CD-40 ligand, heparin, human serum albumin, low molecular weight heparin (LMWH), interferons such as interferon alpha, interferon beta, interferon gamma, interferon omega, interferon tau, consensus interferon; interleukins and interleukin receptors such as interleukin-1 receptor, interleukin-2, interluekin-2 fusion proteins, interleukin-1 receptor antagonist, interleukin-3, interleukin-4, interleukin-4 receptor, interleukin-6, interleukin-8, interleukin-12, interleukin-13 receptor, interleukin-17 receptor; lactoferrin and lactoferrin fragments, luteinizing hormone releasing hormone (LHRH), insulin, pro-insulin, insulin analogues (e.g., mono-acylated insulin as described in U.S. Pat. No. 5,922,675), amylin, C-peptide, somatostatin, somatostatin analogs including octreotide, vasopressin, follicle stimulating hormone (FSH), influenza vaccine, insulin-like growth factor (IGF), insulintropin, macrophage colony stimulating factor (M-CSF), plasminogen activators such as alteplase, urokinase, reteplase, streptokinase, pamiteplase, lanoteplase, and teneteplase; nerve growth factor (NGF), osteoprotegerin, platelet-derived growth factor, tissue growth factors, transforming growth factor-1, vascular endothelial growth factor, leukemia inhibiting factor, keratinocyte growth factor (KGF), glial growth factor (GGF), T Cell receptors, CD molecules/antigens, tumor necrosis factor (TNF), monocyte chemoattractant protein-1, endothelial growth factors, parathyroid hormone (PTH), glucagon-like peptide, somatotropin, thymosin alpha 1, rasburicase, thymosin alpha 1 IIb/IIIa inhibitor, thymosin beta 10, thymosin beta 9, thymosin beta 4, alpha-1 antitrypsin, phosphodiesterase (PDE) compounds, VLA-4 (very late antigen-4), VLA-4 inhibitors, bisphosponates, respiratory syncytial virus antibody, cystic fibrosis transmembrane regulator (CFTR) gene, deoxyreibonuclease (Dnase), bactericidal/permeability increasing protein (BPI), and anti-CMV antibody. Exemplary monoclonal antibodies include etanercept (a dimeric fusion protein consisting of the extracellular ligand-binding portion of the human 75 kD TNF receptor linked to the Fc portion of IgG1), abciximab, adalimumab, afelimomab, alemtuzumab, antibody to B-lymphocyte, atlizumab, basiliximab, bevacizumab, biciromab, bertilimumab, CDP-571, CDP-860, CDP-870, cetuximab, clenoliximab, daclizumab, eculizumab, edrecolomab, efalizumab, epratuzumab, fontolizumab, gavilimomab, gemtuzumab ozogamicin, ibritumomab tiuxetan, infliximab, inolimomab, keliximab, labetuzumab, lerdelimumab, olizumab, radiolabeled lym-1, metelimumab, mepolizumab, mitumomab, muromonad-CD3, nebacumab, natalizumab, odulimomab, omalizumab, oregovomab, palivizumab, pemtumomab, pexelizumab, rhuMAb-VEGF, rituximab, satumomab pendetide, sevirumab, siplizumab, tositumomab, I$^{131}$tositumomab, trastuzumab, tuvirumab, visilizumab, tacrine, memantine, rivastigmine, galantamine, donepezil, levetiracetam, repaglinide, atorvastatin, alefacept, vardenafil, sildenafil, and valacyclovir.

Additional agents suitable for covalent attachment include, but are not limited to, adefovir, alosetron, amifostine, amiodarone, aminocaproic acid, aminohippurate sodium, aminoglutethimide, aminolevulinic acid, aminosalicylic acid, amsacrine, anagrelide, anastrozole, aripiprazole, asparaginase, anthracyclines, bexarotene, bicalutamide, bleomycin, buserelin, busulfan, cabergoline, capecitabine, carboplatin, carmustine, chlorambucin, cilastatin sodium, cisplatin, cladribine, clodronate, cyclophosphamide, cyproterone, cytarabine, camptothecins, 13-cis retinoic acid, all trans retinoic acid; dacarbazine, dactinomycin, daunorubicin, deferoxamine, dexamethasone, diclofenac, diethylstilbestrol, docetaxel, doxorubicin, dutasteride, epirubicin, estramustine, etoposide, exemestane, ezetimibe, fexofenadine, fludarabine, fludrocortisone, fluorouracil, fluoxymesterone, flutamide, fondaparinux, fulvestrant, gamma-hydroxybutyrate, gemcitabine, epinephrine, L-Dopa, hydroxyurea, idarubicin, ifosfamide, imatinib, irinotecan, itraconazole, goserelin, letrozole, leucovorin, levamisole, lisinopril, lovothyroxine sodium, lomustine, mechlorethamine, medroxyprogesterone, megestrol, melphalan, mercaptopurine, metaraminol bitartrate, methotrexate, metoclopramide, mexiletine, mitomycin, mitotane, mitoxantrone, naloxone, nicotine, nilutamide, nitisinone, octreotide, oxaliplatin, pamidronate, pentostatin, pilcamycin, porfimer, prednisone, procarbazine, prochlorperazine, ondansetron, palonosetron, oxaliplatin, raltitrexed, sirolimus, streptozocin, tacrolimus, pimecrolimus, tamoxifen, tegaserod, temozolomide, teniposide, testosterone, tetrahydrocannabinol, thalidomide, thioguanine, thiotepa, topotecan, treprostinil, tretinoin, valdecoxib, celecoxib, rofecoxib, valrubicin, vinblastine, vincristine, vindesine, vinorelbine, voriconazole, dolasetron, granisetron; formoterol, fluticasone, leuprolide, midazolam, alprazolam, amphotericin B, podophylotoxins, nucleoside antivirals, aroyl hydrazones, sumatriptan, eletriptan, macrolides such as erythromycin, oleandomycin, troleandomycin, roxithromycin, clarithromycin, davercin, azithromycin, flurithromycin, dirithromycin, josamycin, spiromycin, midecamycin, loratadine, desloratadine, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, grepafloxacin, gatifloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin; aminoglycosides such as gentamicin, netilmicin, paramecin, tobramycin, amikacin, kanamycin, neomycin, and streptomycin, vancomycin, teicoplanin, rampolanin, mideplanin, colistin, daptomycin, gramicidin, colistimethate; polymixins such as polymixin B, capreomycin, bacitracin, penems; penicillins including penicllinase-sensitive agents like penicillin G, penicillin V; penicllinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefmetazole, ceftazidime, loracarbef, and moxalactam, monobactams like aztreonam; and carbapenems such as imipenem, meropenem, and ertapenem, pentamidine isetionate, albuterol sulfate, lidocaine, metaproterenol sulfate, beclomethasone diprepionate, triamcinolone acetamide, budesonide acetonide, fluticasone, ipratropium bromide, flunisolide, cromolyn sodium, and ergotamine tartrate; taxanes such as paclitaxel; SN-38, and tyrphostines.

Preferred small molecules for coupling to a polymer as described herein are those having at least one naturally occurring amino group. Preferred molecules such as these include aminohippurate sodium, amphotericin B, doxorubicin, aminocaproic acid, aminolevulinic acid, aminosalicylic acid, metaraminol bitartrate, pamidronate disodium, daunorubicin, levothyroxine sodium, lisinopril, cilastatin sodium, mexiletine, cephalexin, deferoxamine, and amifostine.

Preferred peptides or proteins for coupling to a polymer as described herein include EPO, IFN-α, IFN-β, consensus IFN, Factor VIII, Factor IX, GCSF, GMCSF, hGH, insulin, FSH, and PTH.

The above exemplary biologically active agents are meant to encompass, where applicable, analogues, agonists, antagonists, inhibitors, isomers, and pharmaceutically acceptable salt forms thereof. In reference to peptides and proteins, the invention is intended to encompass synthetic, recombinant, native, glycosylated, and non-glycosylated forms, as well as biologically active fragments thereof. In addition, the term "active agent" is intended to encompass the active agent prior to conjugation as well as the active agent "residue" following conjugation.

V. Pharmaceutical Preparations

The present invention also includes pharmaceutical preparations comprising a conjugate as provided herein in combination with a pharmaceutical excipient. Generally, the conjugate itself will be in a solid form (e.g., a precipitate), which can be combined with a suitable pharmaceutical excipient that can be in either solid or liquid form.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The preparation can also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the preparation as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant can be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines (although preferably not in liposomal form), fatty acids and fatty esters;

steroids, such as cholesterol; and chelating agents, such as EDTA, zinc and other such suitable cations.

Acids or bases can be present as an excipient in the preparation. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The pharmaceutical preparations encompass all types of formulations and in particular those that are suited for injection, e.g., powders that can be reconstituted as well as suspensions and solutions. The amount of the conjugate (i.e., the conjugate formed between the active agent and the polymer described herein) in the composition will vary depending on a number of factors, but will optimally be a therapeutically effective dose when the composition is stored in a unit dose container (e.g., a vial). In addition, the pharmaceutical preparation can be housed in a syringe. A therapeutically effective dose can be determined experimentally by repeated administration of increasing amounts of the conjugate in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, preferably from about 5%-98% by weight, more preferably from about 15-95% by weight of the excipient, with concentrations less than 30% by weight most preferred.

These foregoing pharmaceutical excipients along with other excipients are described in "Remington: The Science & Practice of Pharmacy", 19$^{th}$ ed., Williams & Williams, (1995), the "Physician's Desk Reference", 52$^{nd}$ ed., Medical Economics, Montvale, N.J. (1998), and Kibbe, A. H., Handbook of Pharmaceutical Excipients, 3$^{rd}$ Edition, American Pharmaceutical Association, Washington, D.C., 2000.

The pharmaceutical preparations of the present invention are typically, although not necessarily, administered via injection and are therefore generally liquid solutions or suspensions immediately prior to administration. The pharmaceutical preparation can also take other forms such as syrups, creams, ointments, tablets, powders, and the like. Other modes of administration are also included, such as pulmonary, rectal, transdermal, transmucosal, oral, intrathecal, subcutaneous, intra-arterial, and so forth.

As previously described, the conjugates can be administered injected parenterally by intravenous injection, or less preferably by intramuscular or by subcutaneous injection. Suitable formulation types for parenteral administration include ready-for-injection solutions, dry powders for combination with a solvent prior to use, suspensions ready for injection, dry insoluble compositions for combination with a vehicle prior to use, and emulsions and liquid concentrates for dilution prior to administration, among others.

VI. Methods of Administering

The invention also provides a method for administering a conjugate as provided herein to a patient suffering from a condition that is responsive to treatment with conjugate. The method comprises administering, generally via injection, a therapeutically effective amount of the conjugate (preferably provided as part of a pharmaceutical preparation). The method of administering may be used to treat any condition that can be remedied or prevented by administration of the particular conjugate. Those of ordinary skill in the art appreciate which conditions a specific conjugate can effectively treat. The actual dose to be administered will vary depend upon the age, weight, and general condition of the subject as well as the severity of the condition being treated, the judgment of the health care professional, and conjugate being administered. Therapeutically effective amounts are known to those skilled in the art and/or are described in the pertinent reference texts and literature. Generally, a therapeutically effective amount will range from about 0.001 mg to 100 mg, preferably in doses from 0.01 mg/day to 75 mg/day, and more preferably in doses from 0.10 mg/day to 50 mg/day.

The unit dosage of any given conjugate (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted.

One advantage of administering the conjugates of the present invention is that individual water-soluble polymer portions can be cleaved off. Such a result is advantageous when clearance from the body is potentially a problem because of the polymer size. Optimally, cleavage of each water-soluble polymer portion is facilitated through the use of physiologically cleavable and/or enzymatically degradable linkages such as urethane, amide, carbonate or ester-containing linkages. In this way, clearance of the conjugate (via cleavage of individual water-soluble polymer portions) can be modulated by selecting the polymer molecular size and the type functional group that would provide the desired clearance properties. One of ordinary skill in the art can determine the proper molecular size of the polymer as well as the cleavable functional group. For example, one of ordinary skill in the art, using routine experimentation, can determine a proper molecular size and cleavable functional group by first preparing a variety of polymer derivatives with different polymer weights and cleavable functional groups, and then obtaining the clearance profile (e.g., through periodic blood or urine sampling) by administering the polymer derivative to a patient and taking periodic blood and/or urine sampling. Once a series of clearance profiles have been obtained for each tested conjugate, a suitable conjugate can be identified.

It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the art to which the invention pertains.

All articles, books, patents and other publications referenced herein are hereby incorporated by reference in their entireties.

VII. Experimental

The practice of the invention will employ, unless otherwise indicated, conventional techniques of organic synthesis and the like, which are within the skill of the art. Such techniques are fully explained in the literature. See, for example, J. March, Advanced Organic Chemistry: Reactions Mechanisms and Structure, 4th Ed. (New York: Wiley-Interscience, 1992), supra.

In the following examples, efforts have been made to ensure accuracy with respect to numbers used (e.g., amounts, temperatures, etc.) but some experimental error and deviation should be accounted for. Unless indicated otherwise, temperature is in degrees C and pressure is at or near atmospheric pressure at sea level. All reagents were obtained commercially unless otherwise indicated. All molecular weights are in terms of weight average molecular weight and are expressed in units of Daltons ("Da") unless otherwise noted. The following abbreviations are used herein and elsewhere in the specification:

DCC—dicyclohexyl carbodiimide
HOBT—1-hydroxybenzotriazole
MALDI-TOF—matrix-assisted laser desorption/ionization-time of flight
SDS-PAGE—sodium dodecyl sulfate-polyacrylamide gel electrophoresis
K—when used in the context of describing molecular weight, e.g., (2K), indicates thousand
NMR—nuclear magnetic resonance

Example 1

Method A: mPEG(2K Da)-Methyl Ketone with α Ether Bond

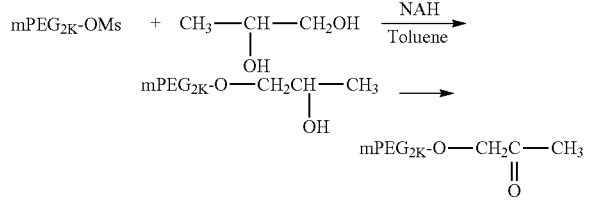

Formation of mPEG (2K Da)-2-Hydroxypropane

To an azeotropically dried solution of mPEG$_{2K}$ Mesylate (mPEG$_{2K}$OMS, Nektar Therapeutics, 2 g, 1 mmole) in 50 mL of anhydrous toluene, 1,2-propanediol (1.522 g, 20 mmole) and sodium hydride (60% in mineral oil, 0.800 g, 20 mmole) were added. The reaction mixture was stirred for 20 hours at 80° C. under nitrogen atmosphere. The insoluble precipitate was filtered off and the filtrate was concentrated under vacuum to dryness. The crude product was dissolved in 3 mL of dichloromethane and precipitated with 100 mL of isopropyl alcohol-diethyl ether (1:1) mixture. The final product was collected using vacuum filtration and dried under vacuum overnight. Yield: 1.4 g. NMR (d$_6$-DMSO): 1.01 ppm (d, —CH$_3$, 3H), 3.24 ppm (s, —OCH$_3$, 3H), 3.51 ppm (s, polymer backbone), 4.54 ppm (d, —OH, 1H).

Formation of mPEG (2K Da)-methyl Ketone

To a stirred suspension of molecular sieves 4A (0.5 g), potassium carbonate (0.34 g, 2.46 mmol), and N-chlorosuccinimide (0.037 g, 0.277 mmol) in 5 mL of anhydrous dichloromethane were successively added mPEG (2K Da)-2-Hydroxypropane (0.5 g, 0.25 mmol) and N-tert-butylbenzenesulfenamide (0.009 g, 0.050 mmol) at 0° C. The reaction mixture was stirred at the same temperature for 2 hours. Next, the solvent was evaporated to dryness under reduced pressure. The residue was dissolved in 20 mL water, the pH was adjusted to 4.5 with 10% of H$_3$PO$_4$, and the desired product was extracted with dichloromethane (20 mL×2). The extract was dried with anhydrous sodium sulfate, concentrated under vacuum, and precipitated with 20 ml of a mixture of isopropyl alcohol and diethyl ether (1:1). The precipitated product was collected through vacuum filtration and dried under vacuum overnight. Yield: 0.35 g NMR (d$_6$-DMSO): 2.04 ppm (s, —CH$_3$, 3H), 3.24 ppm (s, —OCH$_3$, 3H), 3.51 ppm (s, polymer backbone), 4.11 ppm (s, —OCH$_2$(C=O)—, 2H).

Depending on the conditions, the ketone exists in variable amounts of ketone and ketone hydrate. The ketone and ketone hydrate are in equilibrium in the presence of water, both of which can be used (either alone or in combination) to form polymer-active agent conjugates.

PEGylation of Lysozyme

Lysozyme (3.0 mg) was dissolved in 1 mL of 20 mM sodium phosphate buffer (pH 7.5) and MPEG (2K Da)-methyl ketone (8.4 mg, 20 fold molar excess) was added. After 15 minutes, 0.159 M solution of NaCNBH$_3$ (66 µL, 50 fold molar excess) was then added and the solution was stirred for 17 hours at room temperature. Analysis of the reaction mixture by SDS-PAGE showed that PEGylated lysozyme was formed.

This example is repeated several times using different sizes of polymer. First, mPEG mesylate of different sizes are used in place of mPEG$_{2K}$ mesylate to provide a variety of mPEG methyl ketones having different sizes. Specifically, the following different sizes of mPEG mesylate are used: mPEG$_{5K}$ mesylate; mPEG$_{10K}$ mesylate; and mPEG$_{20K}$ mesylate. Once the mPEG methyl ketones having a variety of different sizes are formed, each is conjugated to lysozyme using the procedure described above. Results similar those obtained for the mPEG$_{2K}$ methyl ketone are obtained.

Example 2 mPEG (5K Da)-Methyl Ketone

Method B: mPEG (5K Da)-Methyl Ketone with α Ether Bond

Formation of Ethyl 2-benzyloxylactate

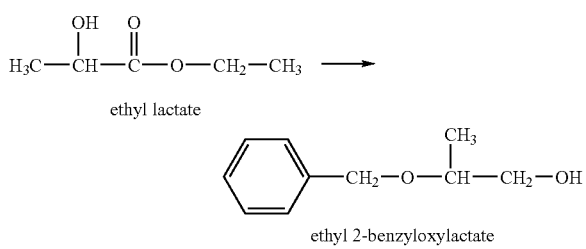

Trifluoromethanesulfonic acid (1.0 mL) was added gradually to a stirred mixture of ethyl lactate (8.90 g, 75 mmole), benzyl 2,2,2-trichloroacetimidate (22.7 g, 90 mmole), anhydrous cyclohexane (100 mL), and anhydrous dichloromethane (50 mL). The mixture was stirred overnight at room temperature under argon atmosphere. The mixture was filtered, and the filtrate was washed with saturated solution of sodium hydrogen carbonate (250 mL), and with distilled water (250 mL). Then, the solution was dried with anhydrous sodium sulfate and the solvents were distilled under reduced pressure using a rotary evaporator. The residue was subjected to fractional vacuum distillation giving 9.6 g of colorless product. NMR (CDCl$_3$): 1.21 ppm (t, —CH$_2$CH$_3$, 3H), 1.32 ppm (d, —CH$_2$—, 3H), 4.13 ppm (m, —CH— and —CH$_2$ CH$_3$, 3H), 4.50 ppm (m, —CH$_2$—, 2H), 7.32 ppm (m, 5H).
Formation of 2-benzyloxy-1-propanol A solution of ethyl 2-benzyloxylactate (9.5 g, 45.6 mmole) in anhydrous tetrahydrofuran (30 mL) was added dropwise during 30 minutes to a stirred solution of lithium aluminum hydride (1.06 g, 28 mmole) in anhydrous tetrahydrofuran (56 mL) at room temperature under argon atmosphere. Next, the mixture was stirred for 3 hours at 60° C. After cooling to 30° C., freshly prepared saturated solution of sodium sulfate (10 mL) was slowly added. The mixture was filtered and the solvent was distilled under reduced pressure. The residue was dissolved in dichloromethane (100 mL) and the solution was dried with anhydrous magnesium sulfate. The solvent then was distilled under reduced pressure. The residue was subjected to fractional vacuum distillation giving 6.2 g of colorless liquid product. NMR (d$_6$-DMSO): 1.90 ppm (d, —CH$_3$, 3H), 3.20-3.50 ppm (bm, —CH— and —CH$_2$—, 3H), 4.53 ppm (s, —CH$_2$—, 2H), 4.63 ppm (t, —OH, 1H), 7.33 ppm (m, 5H).
Formation of mPEG (5 K Da)-mesylate A solution of mPEG (5K Da)-OH (25.0 g, 5 mmole) in toluene (150 mL) was azeotropically dried by distilling off toluene under reduced pressure. The dried mPEG (5K Da)-OH was dissolved in a mixture of anhydrous toluene (150 mL) and anhydrous dichloromethane (30 mL). Next, triethylamine (0.9 mL, 6.5 mmole) and methanesulfonyl chloride (0.45 mL, 5.8 mmole) were added and the mixture was stirred overnight at room temperature under nitrogen atmosphere. The solvents were then distilled off under reduced pressure. Thereafter, the residue was dissolved in dichloromethane (40 mL) and 650 mL isopropyl alcohol was added. The mixture was stirred for 30 minutes at 0° C. and a precipitated product was filtered off and dried under vacuum to yield 22 g of the mesylate derivative shown by NMR to be 100% substituted.
Formation of mPEG (5K Da)-2-benzyloxypropane

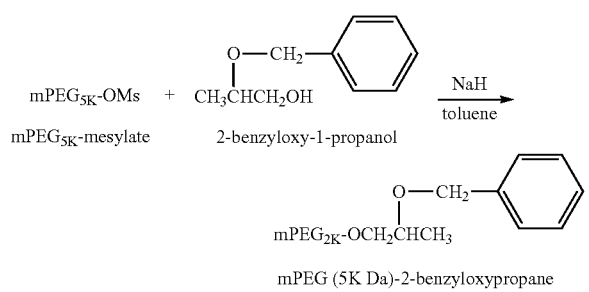

A solution of mPEG (5K Da)-mesylate (15 g, 3 mmole) in toluene (150 mL) was azeotropically dried by distilling off toluene under reduced pressure. The dried mPEG (5K Da)-mesylate was dissolved in anhydrous toluene (150 mL), and 2-benzyloxy-1-propanol (1.5 g, 9 mmole), and sodium hydride (60% dispersion in mineral oil, 0.36 g, 9 mmole) were added and the reaction mixture was stirred at 85° C. overnight under a nitrogen atmosphere. After cooling to room temperature, the mixture was filtered and the solvent was distilled off under reduced pressure. The residue was dissolved in dichloromethane (20 mL) and precipitated with 350 mL isopropyl alcohol at 0-5° C. The precipitated product was filtered off and dried under reduced pressure. Yield: 12.7 g. NMR (d$_6$-DMSO): 1.10 ppm (d, —CH$_3$, 3H), 3.24 ppm (s, —OCH$_3$, 3H), 3.51 ppm (s, polymer backbone), 4.53 ppm (s, —CH$_2$—, 2H), 7.33 ppm (m, 5H).
Formation of mPEG (5K Da)-2-hydroxypropane

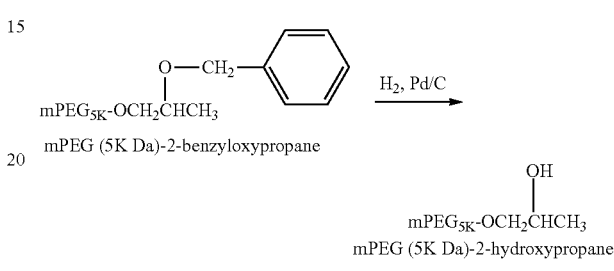

A mixture of mPEG (5K Da)-2-benzyloxypropane (8.8 g), ethyl alcohol (120 mL), and palladium (10% on active carbon, 0.8 g) was hydrogenated overnight under 45 psi of hydrogen. The mixture was filtered and the solvent was distilled off under reduced pressure. The crude product was dissolved in dichloromethane (15 mL) and precipitated with 300 mL isopropyl alcohol at 0-5° C. The precipitated product was filtered off and dried under reduced pressure. Yield: 6.1 g. NMR (d$_6$-DMSO): 1.01 ppm (d, —CH$_3$, 3H), 3.24 ppm (s, —OCH$_3$, 3H), 3.51 ppm (s, polymer backbone), 4.54 ppm (d, —OH, 1H).
Formation of mPEG (5K Da)-Methyl Ketone

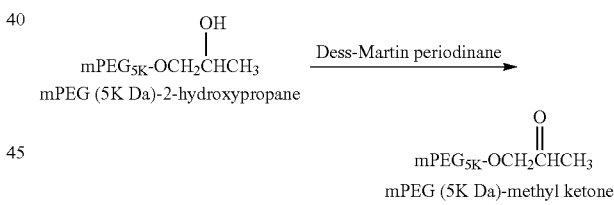

mPEG (5K Da)-2-Hydroxypropane (4.0 g) was added to a solution of Dess-Martin periodinane (0.44 g) in dichloromethane (20 mL) and the mixture was stirred for 6 hours at room temperature. Next, the solvent was distilled off under reduced pressure. The residue was then dissolved in warm isopropyl alcohol (100 mL), and ethyl ether (50 mL) was added. The mixture was stirred for 15 minutes. The precipitated product was filtered off and dried under reduced pressure. Yield: 3.2 g. NMR (d$_6$-DMSO): 2.04 ppm (s, —CH$_3$, 3H), 3.24 ppm (s, —OCH$_3$, 3H), 3.51 ppm (s, polymer backbone), 4.11 ppm (s, —OCH$_2$(C=O)—, 2H).

Depending on the conditions, the ketone exists in variable amounts of ketone and ketone hydrate. The ketone and ketone hydrate are in equilibrium in the presence of water, both of which can be used (either alone or in combination) to form polymer-active agent conjugates.
PEGylation of Lysozyme Lysozyme (3.0 mg) was dissolved in 1 mL of 20 mM sodium phosphate buffer (pH 7.5) and mPEG (5K Da)-methyl ketone (7.5 mg) was added. After 15 minutes, 0.1 M solution of NaCNBH$_3$ (42 µL) was added and the solution was stirred for 18 hours at room temperature. Analysis of the reaction mixture by SDS-PAGE showed that PEGylated lysozyme was formed.

This example is repeated several times using different sizes of polymer. First, mPEG mesylate of different sizes are used in place of mPEG$_{5K}$ mesylate to provide a variety of mPEG methyl ketones having different sizes. Specifically, the following different sizes of mPEG mesylate are used: mPEG$_{2K}$ mesylate; mPEG$_{10K}$ mesylate; and mPEG$_{20K}$ mesylate. Once the mPEG methyl ketones having a variety of different sizes are formed, each is conjugated to lysozyme using the procedure described above. Results similar those obtained for the mPEG$_{5K}$ methyl ketone are obtained Example 3 mPEG (5K Da)-Piperidone and its Corresponding Ketone Hydrate

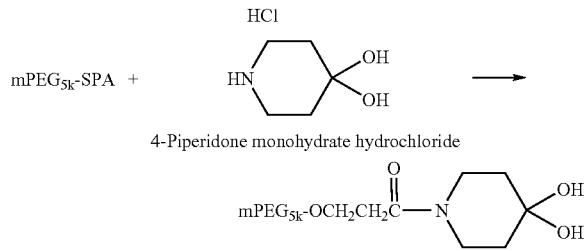

Formation of mPEG-piperidone

To a solution of the succinimidyl ester of mPEG (5K Da)-propionic acid (Nektar Therapeutics, mPEG$_{5K}$-SPA, 1.0 g, 2 mmole,) in dichloromethane (20 mL), triethylamine (0.084 mL, 6 mmole) and 4-piperidone monohydrate hydrochloride (0.077 g, 5 mmole) were added. The reaction mixture was stirred at room temperature under nitrogen atmosphere overnight. Insoluble precipitate was filtered and filtrate was evaporated to dryness. The crude product was dissolved in dichloromethane and precipitated with isopropyl alcohol. The final product was collected through vacuum filtration and dried under vacuum overnight. Yield: 0.88 g. NMR (d$_6$-DMSO): 2.32 ppm (t, —C$\underline{H}_2$—C(OH)$_2$—C$\underline{H}_2$—), 2.42 ppm (t, —C$\underline{H}_2$—C(OH)$_2$C$\underline{H}_2$—), 2.66 ppm (t, —OCH$_2$C$\underline{H}_2$CON—), 3.24 ppm (s, —OCH$_3$), 3.51 ppm (s, polymer backbone).

Depending on the conditions, the ketone hydrate exists in variable amounts of ketone hydrate and ketone. The ketone hydrate and ketone are in equilibrium in the presence of water, both of which can be used (either alone or in combination) to form polymer-active agent conjugates.

PEGylation of Lysozyme

The protein lysozyme is used as a model to demonstrate the ability of the a given polymeric reagent to form conjugations with a protein. Lysozyme is a 129 amino acid secretory enzyme containing six lysine residues, each having a side chain terminating in an amine residue. Amine residues represent potential attachment sites for the polymeric reagents of the invention.

Lysozyme from chicken egg white (3 mg, Sigma, St. Louis, Mo., product number L-6876) was dissolved in 1 ml of 20 mM sodium phosphate buffer (pH 7.5, J. T. Baker, Phillipsburg, N.J.). m-PEG$_{5K}$-Ketone of Example 3 (21 mg, a 20-fold molar excess to the lysozyme) was added into the lysozyme solution. The vial was placed on a Roto Mix™ orbital shaker (Thermolyne Corp., Dubuque, Iowa) set at slow speed to allow reaction to proceed at room temperature. After 15 minutes, 0.066 mL of 159 mM aqueous NaCNBH$_3$ (available from, for example, Aldrich, St. Louis, Mo., product number 15,615-9) was added. This amount of NaCNBH$_3$ represented a 50-fold molar excess to the lysozyme. Aliquots (20 µL) were withdrawn at timed intervals (17 hours and 41 hours) from the reaction mixture and were analyzed by SDS-PAGE using a precast gel electrophoresis system based on a 10% Tris-HCl Ready Gel™ precast gel (both available from Bio-Rad Laboratories, Hercules, Calif.) and MALDI-TOF Mass Spectroscopy using an OmniFLEX® MALDI-TOF Mass Spectrometer (Bruker Daltonics, Inc., Bellerica, Mass.). SDS-PAGE analysis indicated the presence of PEG derivatives of lysozyme having 1, 2, and 3 PEG moieties attached. MALDI-TOF mass spectrometry displayed peaks for three PEGylated derivatives of lysozyme at 19,660 Da, 25,069 Da, and 30,568 Da, differing in mass by approximately 5000 Da. The mass of unmodified lysozyme by MALDI-TOF was 14,198 Da.

This example is repeated several times using different sizes of polymer. First, mPEG-SPA of different sizes are used in place of mPEG$_{5K}$-SPA to provide a variety of MPEG piperidones having different sizes. Specifically, the following different sizes of mPEG-SPA are used: mPEG$_{2K}$-SPA; mPEG$_{10K}$-SPA; and mPEG$_{20K}$-SPA. Once the mPEG-piperidones having a variety of different sizes are formed, each is conjugated to lysozyme using the procedure described above. Results similar those obtained for the mPEG$_{5K}$-piperidone are obtained.

Example 4 mPEG Methyl Ketone

Method C: mPEG (5K Da) Methyl Ketone with β Carbamido Group

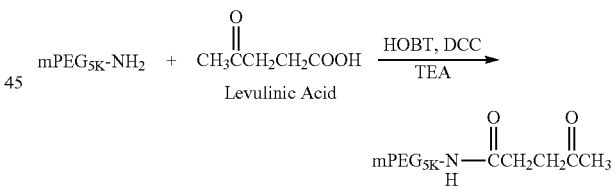

Levulinic acid (0.07 g, 6 mmole) was dissolved in anhydrous dichloromethane (20 mL). Next, mPEG (5K Da)-amine (Nektar Therapeutics, 2.0 g, 4 mmole), triethylamine (0.028 mL, 2 mmoles), 1-hydroxybenzotriazole (0.027 g, 2 mmole), and 1,3-dicyclohexylcarbodiimide (0.12 g, 6 mmole) were added. The reaction mixture was stirred at room temperature under nitrogen atmosphere overnight. Insoluble precipitate was filtered off and the filtrate was evaporated to dryness. The crude product was dissolved in dichloromethane and precipitated with isopropyl alcohol (50 mL). The final product was collected through vacuum filtration and dried under vacuum overnight. Yield: 1.72 g. NMR (d$_6$-DMSO): 2.28 ppm (t, —NH—COC$\underline{H}_2$COCH$_3$, 2H), 2.32 ppm (s, —CH$_3$, 3H), 2.62 ppm (t, —NH—COCH$_2$C$\underline{H}_2$COCH$_3$, 2H), 3.16 ppm (q. —CH$_2$C$\underline{H}_2$NH—CO—, 2H), 3.24 ppm (s, —OCH$_3$, 3H), 3.51 ppm (s, polymer backbone), 7.87 ppm (t, —N$\underline{H}$—CO—CH$_2$—, 1H).

Depending on the conditions, the ketone exists in variable amounts of ketone and ketone hydrate. The ketone and ketone hydrate are in equilibrium in the presence of water, both of which can be used (either alone or in combination) to form polymer-active agent conjugates.

PEGylation of Lysozyme

Lysozyme (3.0 mg) was dissolved in 1 mL of 20 mM sodium phosphate buffer (pH 7.5) and mPEG (5K Da)-Ketone (21 mg, 20 fold excess) prepared from this example was added. After stirring for 15 minutes, 0.159 M solution of $NaCNBH_3$ (66 μL, 50 fold molar excess) was added and the solution was stirred 20 h at room temperature. Analysis of the reaction mixture by SDS-PAGE showed that PEGylated lysozyme was formed.

This example is repeated several times using different sizes of polymer. First, mPEG-amine of different sizes are used in place of $mPEG_{5K}$-amine to provide a variety of differently sized mPEG methyl ketones with a β carbamido group. Specifically, the following different sizes of mPEG-amine are used: $mPEG_{2K}$-amine; $MPEG_{10K}$-amine; and $mPEG_{20K}$-amine. Once the differently sized mPEG methyl ketones with a β carbamido group are formed, each is conjugated to lysozyme using the procedure described above. Results similar those obtained for the $mPEG_{5K}$ methyl ketone with a β carbamido group are obtained.

Example 5

PEG2 Ketone (Linkerless PEG2 Ketone) via Ethoxylation: PEG2(6K Da) Ketone

Formation of 2-benzyloxy-1,3-bis(ω-hydroxypoly(ethylene glycol))propane

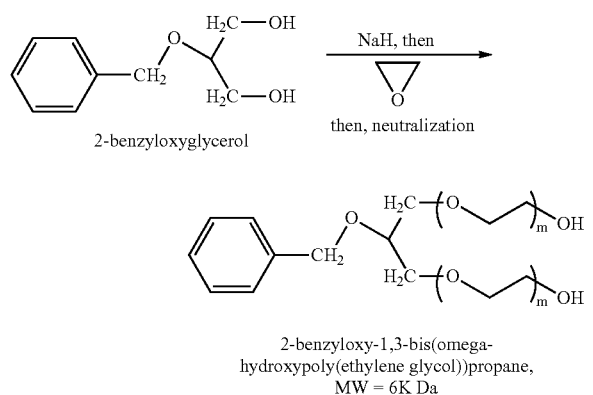

2-Benzyloxyglycerol, available from Sigma-Aldrich (St. Louis, Mo.) was ethoxylated to form 2-benzyloxy-1,3-bis(ω-hydroxypoly(ethylene glycol))propane, MW=6K Da. The variable (m) in the above structures is a number to provide a polymer weight of 3,000 Daltons, thereby providing a total weight of essentially 6,000 Daltons. NMR analysis of the product confirmed its structure and HPLC and GPC analysis confirmed its purity and molecular weight. This polymer was used at the raw material for the ketone formed by the reaction scheme shown below.

Methylation of 2-benzyloxy-1,3-bis(ω-hydroxypoly(ethylene glycol))propane, MW=6K Da

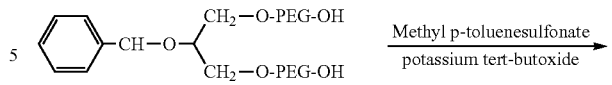

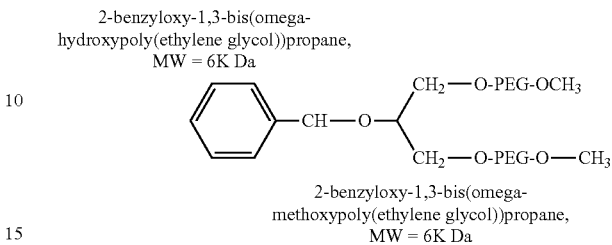

2-benzyloxy-1,3-bis(ω-hydroxypoly(ethylene glycol)) propane, MW=6K Da (10 g, 1.67 mmol) in 400 mL of toluene was azeotropically dried by distilling off toluene under reduced pressure. The residue was redissolved in 700 mL of anhydrous toluene. To the solution were added potassium tert-butoxide (1.0 M solution in tert-butanol, 16 mL, 16.7 mmol) and methyl p-toluenesulfonate (3.5 mL, 23.3 mmol). The reaction mixture was stirred at 45° C. under nitrogen atmosphere overnight. The mixture was filtered and the filtrate was evaporated to dryness under reduced pressure. The residue was dissolved in 500 mL of $H_2O$, NaCl (50 g) was added and the pH of the solution was adjusted to 7.5. The product was extracted with dichloromethane (250 mL×2). The extract was dried with magnesium sulfate, concentrated under vacuum and the product was precipitated with a mixture of isopropyl alcohol and diethyl ether (7:3, 500 mL). Next, the product was dried under vacuum overnight. Yield: 7.8 g. NMR (d6-DMSO): 3.24 ppm (s, —$OCH_3$, 6H), 3.51 ppm (s, polymer backbone), 4.61 ppm (s, —$OCH_2C_6H_5$, 2H), 7.33 ppm (m, —$OCH_2\underline{C_6H_5}$, 5H), Formation of 2-hydroxy-1,3-bis(ω-methoxypoly(ethylene glycol))propane

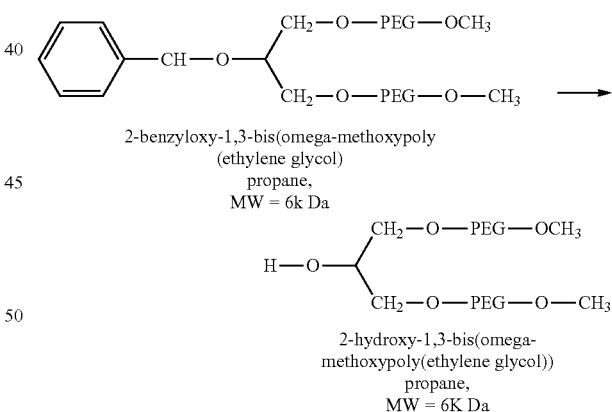

2-Benzyloxy-1,3-bis(ω-methoxypoly(ethylene glycol)) propane, MW=6K Da (5.0 g, 0.83 mmol) was dissolved in 100 mL of ethyl alcohol, and $Pd(OH)_2$ (5% on active carbon, 0.25 g), and cyclohexene (0.84 mL, 8.3 mmol) were added. The suspension was refluxed for 2 hours. The catalyst was filtered and filtrate was evaporated to dryness. The residue was dissolved in dichloromethane (5 mL) and precipitated with 300 mL of diethyl ether. The final product was collected through vacuum filtration and dried under vacuum overnight. Yield: 4.6 g. NMR ($d_6$-DMSO): 3.24 ppm (s, —$OCH_3$, 6H), 3.51 ppm (s, polymer backbone), 4.76 ppm (d, —CH—$\underline{OH}$, 1H).

Formation of mPEG2-(6K Da)-Ketone

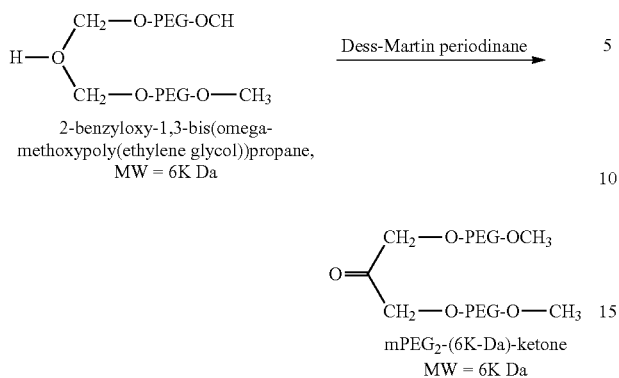

PEGylation of Lysozyme

2-Hydroxy-1,3-bis(ω-methoxypoly(ethylene glycol))propane, MW=6K Da (4.0 g, 0.67 mmol) was added to a stirred solution of Dess-Martin periodinane (0.37 g, 0.867 mmol) in dichloromethane (20 mL). The reaction mixture was stirred for 6 hours at the room temperature. Thereafter, it was concentrated and the product was precipitated with a mixture of isopropyl alcohol and diethyl ether (2:1, 300 mL). The precipitate was collected through vacuum filtration and dried under vacuum overnight. Yield: 3.8 g. NMR ($d_6$-DMSO): 3.24 ppm (s, —$OCH_3$, 6H), 3.51 ppm (s, polymer backbone), 4.22 ppm (s, —O—$\underline{CH_2}$—C=O, 4H).

Depending on the conditions, the ketone exists in variable amounts of ketone and ketone hydrate. The ketone and ketone hydrate are in equilibrium in the presence of water, both of which can be used (either alone or in combination) to form polymer-active agent conjugates.

PEGylation of Lysozyme

Lysozyme (3.0 mg) was dissolved in 1 mL of 20 mM sodium phosphate buffer (pH 7.5) and mPEG2-(6K Da)-ketone (25 mg, 20 fold excess) was added. After 15 minutes, 0.159 M solution of $NaCNBH_3$ (105 μL, 50 fold molar excess) was added and the solution was stirred for 20 hours at room temperature. Analysis of the reaction mixture by SDS-PAGE showed that PEGylated lysozyme was formed.

This example is repeated several times using different sizes of mPEG2-(6K Da)-ketone. The following different sizes of mPEG2-(6K Da)-ketone are used: mPEG2-(10K Da)-ketone; mPEG2-(20K Da)-ketone; and mPEG2-(40K Da)-ketone. In each case, similar results to the mPEG2-(6K Da)-ketone are obtained.

Example 6 mPEG2(40K Da)-Piperidone and its Hydrate

Formation of mPEG2(40K)-Piperidone and its Hydrate

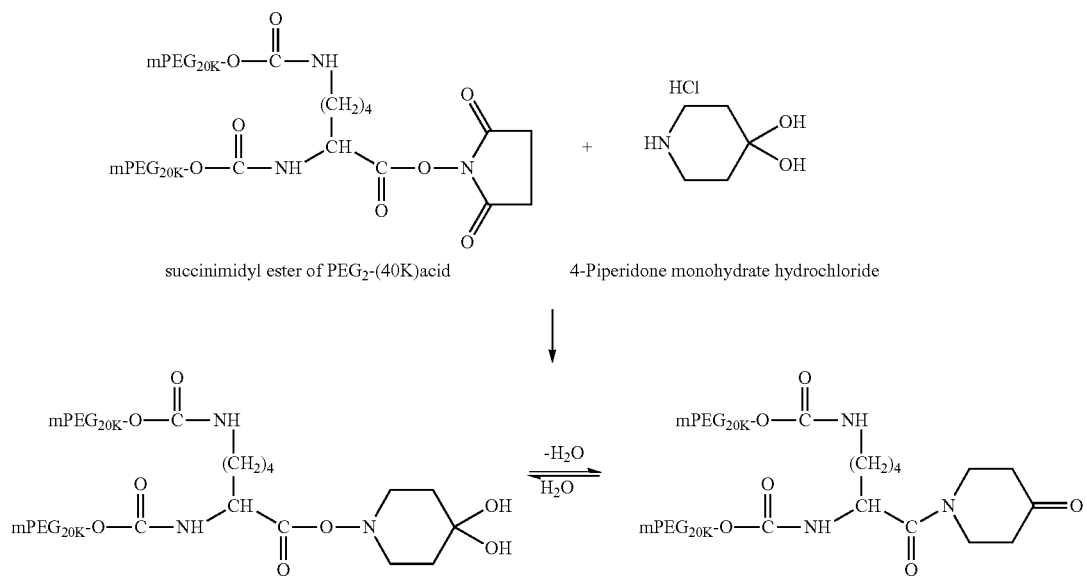

To a solution of succinimidyl ester of PEG2-(40K Da) acid (Nektar Therapeutics, 10 g, 0.25 mmole) in dichloromethane (200 mL), triethylamine (0.100 ml, 0.72 mmole) and 4-piperidone monohydrate hydrochloride (0.100 g, 0.65 mmole) were added. The reaction mixture was stirred at room temperature under nitrogen atmosphere overnight. Next the solvent was distilled off under reduced pressure. The residue was dissolved in dichloromethane and precipitated with a mixture of isopropyl alcohol and ethyl ether. The product was collected through vacuum filtration and dried under vacuum overnight. Yield: 9.5 g. NMR ($d_6$-DMSO): 2.33 ppm and 2.43 ppm (t, —$\underline{CH_2}$—C(OH)$_2$—$\underline{CH_2}$—, 4H), 3.24 ppm (s, —$OCH_3$, 6H), 3.51 ppm (s, polymer backbone), 4.36 ppm (m, —$\underline{CH_2}$OCONH—, 4H), 7.18 ppm (t, —NH— lysine, 1H), 8.04 ppm (d, —NH— lysine, 1H).

As shown schematically above, the ketone exists in variable amounts of ketone and ketone hydrate. The ketone and ketone hydrate are in equilibrium in the presence of water, both of which can be used (either alone or in combination) to form polymer-active agent conjugates.

PEGylation of Lysozyme

Lysozyme (3.0 mg) was dissolved in 1 ml of 20 mM sodium phosphate buffer (pH 7.5) and PEG2(40K Da)-piperidone (168 mg, 20 fold excess) was added. After 15 minutes, 0.159 M solution of NaCNBH$_3$ (66 µL, 50 fold molar excess) was added and the solution was stirred for 24 hours at room temperature. Analysis of the reaction mixture by SDS-PAGE showed that PEGylated lysozyme was formed.

Example 7

PEG2 Ketone: mPEG2(40K Da)-Ketone with two α Amido Linkers

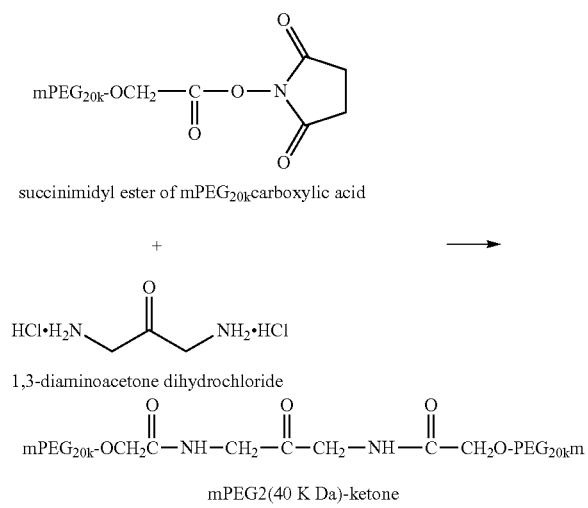

To a solution of succinimidyl ester of mPEG (20K Da) carboxylic acid (12 g, 0.6 mmole) in acetonitrile (50 ml), 1,3-diaminoacetone dihydrochloride monohydrate (0.054 g, 0.3 mmole), and 4-(dimethylamino)pyridine (0.909 g) were added. The reaction mixture was stirred for 48 hours at room temperature under nitrogen atmosphere. Next, the solvent was distilled off under reduced pressure. The residue was dissolved in dichloromethane and precipitated with a mixture of isopropyl alcohol and ethyl ether. The final product was collected through vacuum filtration and dried under vacuum overnight. Yield: 9.5 g. NMR (d$_6$-DMSO): 3.24 ppm (s, —OCH$_3$, 6H), 3.51 ppm (s, polymer backbone), 4.00 ppm (s, —OCH$_2$CONH—, 4H), 4.29 ppm (d, NH—CH$_2$(C=O)CH$_2$—NH—, 2H), 6.68 ppm (t, —NH—CH$_2$(C=O)CH$_2$—NH—, 2H).

Example 8 mPEG (5K Da) Methyl Ketone, Method A: mPEG (5K Da)-Methyl Ketone with an α Amido Linker

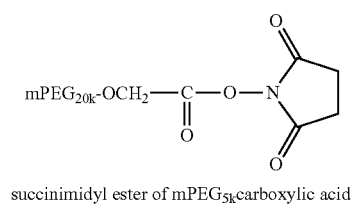

succinimidyl ester of mPEG$_{5k}$carboxylic acid

-continued

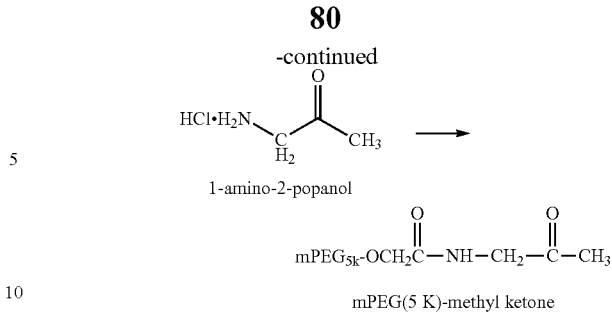

To a solution of succinimidyl ester of mPEG (5K Da) carboxylic acid (10 g, 2 mmole) in acetonitrile (100 mL), 1-amino-2-propanol (0.9 g, 12 mmole), and 4-(dimethylamino)pyridine (1.5 g) were added. The reaction mixture was stirred overnight at room temperature under nitrogen atmosphere. Next, the solvent was distilled off under reduced pressure. The residue was dissolved in 200 ml distilled water. NaCl (30 g) was added and the product was extracted with dichloromethane (80 and 40 mL). The extract was dried with anhydrous sodium sulfate and it was concentrated under reduced pressure. Thereafter, the product was precipitated with a mixture of isopropyl alcohol and ethyl ether and was collected through vacuum filtration and dried under vacuum overnight. Yield: 9.5 g.

The above product (7.0 g, 1.4 mmole) was dissolved in dichloromethane (70 mL) and Dess-Martin periodinane (1.17 g) was added. The reaction mixture was stirred overnight at room temperature under nitrogen atmosphere. Next, the reaction mixture was washed with 15%-NaCl solution (200 mL), dried with anhydrous sodium sulfate, and concentrated under reduced pressure. Thereafter, the product was precipitated with a mixture of isopropyl alcohol and ethyl ether giving 6.2 g of white solid after drying under reduced pressure. NMR (d$_6$-DMSO): 2.08 ppm (s, —CH$_3$, 3H), 3.24 ppm (s, —OCH$_3$, 3H), 3.51 ppm (s, polymer backbone), 3.94 ppm (s, —OCH$_2$CONH—, 2H), 3.97 ppm (d, —NHCH$_2$(C=O)—, 2H), 7.98 ppm (t, —NH—CH$_2$(C=O)—, 1H).

Depending on the conditions, the ketone exists in variable amounts of ketone and ketone hydrate. The ketone and ketone hydrate are in equilibrium in the presence of water, both of which can be used (either alone or in combination) to form polymer-active agent conjugates.

Example 9

PEG (5K Da)-α-Hydroxy-ω-2-Propanone Diethyl Ketal (with Alpha Ether Bond)

Formation of Ethyl Pyruvate Diethyl Ketal

A mixture of ethyl pyruvate (13.92 g, 0.120 moles), triethyl orthoformate (19.44 g, 0.131 moles), ethyl alcohol (9.0 g), and p-toluenesulfonic acid monohydrate (0.0432 g, 0.00227 moles) was stirred at 45° C. overnight under nitrogen atmosphere. Next, after cooling to room temperature, Na$_2$CO$_3$ (1.20 g) was added and the mixture was stirred for 15 minutes. The reaction mixture was then filtered and ethyl alcohol and residual triethyl orthoformate were distilled off under reduced pressure. The residue was subjected to fractional vacuum distillation giving 18.2 g of pure ethyl pyruvate diethyl ketal. NMR (d$_6$-DMSO): 1.27 ppm (t, —CH$_3$, ethyl (ketal), 6H) 1.34 ppm (t, —CH$_3$, ethyl (ester), 3H), 1.40 ppm (s, —CH$_3$—C—COO—, 3H), 3.45 ppm (q, —OCH$_2$CH$_3$, (ketal), 4H), 4.29 ppm (q, —OCH$_2$CH$_3$, (ester), 2H).

Formation of 2,2-Diethoxypropan-1-ol

A solution of ethyl pyruvate diethyl ketal (16.0 g, 0.084 moles) in ethyl ether (60 mL) was added dropwise during 30 min to a stirred solution of lithium aluminum hydride (1.90 g, 0.050 moles) in ethyl ether (150 mL). Next the mixture was stirred 1 h at room temperature under nitrogen atmosphere. Saturated solution of sodium sulfate (20 mL) was added and the mixture was stirred 15 min. Next the mixture was filtered, dried with anhydrous magnesium sulfate, and the solvent was distilled off. The residue was subjected to fractional vacuum distillation giving 9.5 g of pure 2,2-diethoxypropan-1-ol. NMR (d$_6$-DMSO): 1.17 ppm (t, —CH$_3$, ethyl (ketal), 6H), 1.31 ppm (s, —CH$_3$—C—CH$_2$OH, 3H), 3.37 ppm (q, —O CH$_2$CH$_3$, (ketal), 4H), 3.86 ppm (d, —CH$_2$OH, 2H), 4.45 ppm (t, —OH, 1H).

PEG (5K Da)-α-Hydroxy-ω-2-Propanone Diethyl Ketal

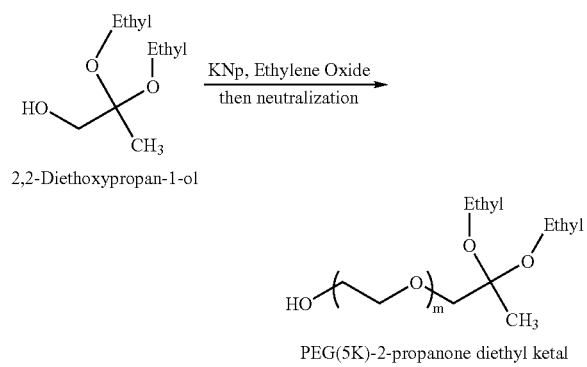

2,2-Diethoxypropan-1-ol

PEG(5K)-2-propanone diethyl ketal 2,2-Diethoxypropan-1-ol (0.366 g, 0.00247 moles), THF (200 mL), and potassium naphthalene 0.3 mol/L-tetrahydrofuran (THF) solution (20 mL, 0.006 moles) were added to a glass reactor and stirred for 3 minutes in an nitrogen atmosphere. Ethylene oxide (12.6 g 0.286 moles) was added to this solution and the reaction mixture was stirred for 48 hours at room temperature. Next, the mixture was purged with nitrogen and 0.1M phosphate buffer (pH=8, 150 ml) was added. The THF layer was separated and discarded. Naphthalene was removed from the solution by ethyl ether extraction. The product was extracted from the residue with dichloromethane (3×100 mL). The extract was dried with anhydrous sodium sulfate and concentrated to about 50 mL. Next, ethyl ether (300 mL) was added and the mixture was stirred for 15 minutes at 0° C. The precipitated product was filtered off and dried under reduced pressure. The variable (m) in the above structure is a number to provide a polymer weight of 5,000 Daltons. Yield 11.7 g. NMR (d$_6$-DMSO): 1.17 ppm (t, —CH$_3$, ethyl (ketal), 6H), 1.31 ppm (s, —CH$_3$ —C—CH$_2$O—, 3H), 3.51 ppm (s, polymer backbone), 4.57 ppm (t —OH, 1H).

PEGylation of Lysozyme

Lysozyme (3.0 mg) was dissolved in 1 mL of 20 mM sodium phosphate buffer (pH 5.0) and PEG (5K Da)-α-hydroxy-ω-2-propanone diethyl ketal (21 mg, 20 fold excess) was added. After 15 minutes, 0.159 M solution of NaCNBH$_3$ (66 µL, 50 fold molar excess) was added and the solution was stirred for 20 hours at room temperature. Analysis of the reaction mixture by SDS-PAGE showed that PEGylated lysozyme was formed.

This example is repeated several times using different sizes of PEG (5K Da)-α-hydroxy-ω-2-propanone diethyl ketal. The following different sizes of PEG-α-hydroxy-ω-propanone diethyl ketal are used: PEG (2K Da)-α-hydroxy-ω-2-propanone diethyl ketal; PEG (10K Da)-α-hydroxy-ω-2-propanone diethyl ketal; PEG (20K Da)-α-hydroxy-ω-2-propanone diethyl ketal; and PEG (40K Da)-α-hydroxy-ω-2-propanone diethyl ketal. In each case, similar results to the PEG (5K)-α-hydroxy-ω-2-propanone diethyl ketal are obtained.

Example 10

Preparation of Polymer-EPO Conjugate-Random PEGylation of EPO

Recombinant erythropoietin, "EPO" (produced in *E. coli*, mammalian cells such as Chinese hamster ovary cells, or another source) is coupled to mPEG (5K)-methyl ketone (prepared as described in Example 2).

EPO (~2 mg) is dissolved in 1 ml of 50 mM phosphate buffer (pH 7.6) and mPEG (5K) methyl ketone is added at 5× the molar EPO concentration. A reducing agent, NaCNBH$_3$, is added and the solution stirred for 24 hours at room temperature to couple the mPEG (5K)-methyl ketone reagent to the protein via an amine linkage.

The reaction mixture is analyzed by SDS-PAGE to determine the degree of PEGylation. Confirmation of the degree of PEGylation, 1-mer, 2-mers, etc. is done by Matrix Assisted Laser Desorption Ionization Time-of-Flight (MALDI-TOF) mass spectrometry. The displayed peaks for native and monoPEGylated species differ by approximately 5,000 Daltons. The resulting reaction mixture contains a mixture of native and monoPEGylated protein. Increasing the ratio of PEG reagent to protein increases the degree of polyPEGylation, that is to say, the formation of 2-mers, 3-mers, and so on.

The above demonstrates random PEGylation of an illustrative protein of the invention to yield a distribution of PEGylated EPO products. If desired, the reaction mixture can be further separated to isolate the individual isomers as described below.

PEG conjugates having different molecular weights are separated by gel filtration chromatography. The different PEG conjugates (1-mer, 2-mer, 3-mer, and so forth) are fractionated on the basis of their different molecular weights (in this case, varying by approximately 5,000 Daltons). Specifically, the separation is performed by using a serial column system suitable for effective separation of products in the molecular weight range observed, e.g., a Superdex™200 column (Amersham Biosciences). The products are eluted with 10 ml acetate buffer at a flow rate of 1.5 ml/min. The collected fractions (1 ml) are analyzed by OD at 280 nm for protein content and also using an iodine test for PEG content (Sims et al. (1980) *Anal Biochem.* 107:60-63). In addition, the results can be visualized by running an SDS PAGE gel, followed by staining with barium iodide. Fractions corresponding to the eluted peaks are collected, concentrated by ultrafiltration using a membrane, and lyophilized. This method results in separation/purification of conjugates having the same molecular weights but does not provide separation of conjugates having the same molecular weight but different PEGylation sites (i.e., positional isomers).

Separation of positional isomers is carried out by reverse phase chromatography using an RP-HPLC C18 column (Amersham Biosciences or Vydac). This procedure is effective for separating PEG-biomolecule isomers having the same molecular weight (positional isomers). The reverse-phase chromatography is carried out using a RP-HPLC C18 preparative column and eluted with a gradient of water/0.05% TFA (Eluent A) and acetonitrile/0.05% TFA (Eluent B).

Fractions corresponding to the eluted peaks are collected, evaporated to eliminate acetonitrile and TFA, followed by removal of solvent to isolate the individual positional PEG-isomers.

Example 11

Preparation of Polymer-EPO Conjugate—N-terminal PEGylation of EPO

Recombinant erythropoietin, "EPO" (produced in *E. coli*, mammalian cells such as Chinese hamster ovary cells, or another source) is coupled to mPEG (5K)-methyl ketone (prepared as described in Example 2).

EPO (~2 mg) is dissolved in 1 ml of 0.1 mM sodium acetate (pH 5) and mPEG (5K)-methyl ketone is added at 5× the molar EPO concentration. A reducing agent, NaCNBH$_3$, is added and the solution is stirred for 24 hours at 4° C. to couple the mPEG (5K)-methyl ketone reagent to the protein via an amine linkage.

The reaction mixture is analyzed by SDS-PAGE to determine the degree of PEGylation. Confirmation of the degree of PEGylation, 1-mer, 2-mers, and so one, is carried out by Matrix Assisted Laser Desorption Ionization Time-of-Flight (MALDI-TOF) mass spectrometry. The displayed peaks for native and mono-PEGylated species differ by approximately 5,000 Daltons. The resulting reaction mixture primarily contains a mixture of native and monoPEGylated protein. The monoPEGylated species are purified by column chromatography to remove free EPO and higher molecular weight species.

Confirmation of N-terminal PEGylation is carried out by peptide mapping. Increasing the ratio of PEG to protein increases the degree of PEGylation, yielding polyPEGylated protein.

The above demonstrates PEGylation of an illustrative protein of the invention to yield a predominantly N-terminal single PEGylated protein.

Example 12

N-terminal PEGylation of GCSF

Recombinant granulocyte colony stimulating factor, "GCSF" (produced in *E. coli*, mammalian cells such as Chinese hamster ovary cells, or another source) is coupled to mPEG (5K)-methyl ketone (prepared as described in Example 8).

GCSF (~2. mg) is dissolved in 1 ml of 0.1 mM sodium acetate (pH 5) and mPEG (5K)-methyl ketone (from Example 2) is added at 5× the molar GCSF concentration. The reducing agent, NaCNBH$_3$, is added and the solution stirred for 24 hours at 4° C. to couple the mPEG (5K)-methyl ketone reagent to the protein via an amine linkage.

The resulting reaction mixture is analyzed by SDS-PAGE to determine the degree of PEGylation. Confirmation of the degree of PEGylation, 1-mer, 2-mers, and so forth, is carried out by Matrix Assisted Laser Desorption Ionization Time-of-Flight (MALDI-TOF) mass spectrometry. The displayed peaks for native and mono-PEGylated species differ by approximately 5,000 Daltons. The resulting reaction mixture primarily contains a mixture of native and monoPEGylated GCSF. The monoPEGylated species are purified by column chromatography to remove free GCSF and higher molecular weight species. Confirmation of N-terminal PEGylation is conducted by peptide mapping. Increasing the ratio of PEG to protein increases the degree of PEGylation yielding polyPEGylated protein.

Example 13

N-terminal PEGylation of Interferon-α

Recombinant interferon-alfa, "IFN-α" (produced in *E. coli*, mammalian cells such as Chinese hamster ovary cells, or another source) is coupled to mPEG (5K Da)-methyl ketone (prepared as described in Example 8).

IFN-α (~2. mg) is dissolved in 1 ml of 0.1 mM sodium acetate (pH 5) and mPEG (5K Da)-methyl ketone is added at 5× the molar IFN-α concentration. A reducing agent, NaCNBH$_3$, is added and the solution stirred for 24 hours at 4° C. to couple the mPEG (5K Da)-methyl ketone reagent to the protein via an amine linkage.

The reaction mixture is analyzed by SDS-PAGE to determine the degree of PEGylation. Confirmation of the degree of PEGylation, 1-mer, 2-mers etc. is carried out by Matrix Assisted Laser Desorption Ionization Time-of-Flight (MALDI-TOF) mass spectrometry. The displayed peaks for native and monoPEGylated species differ by approximately 5,000 Daltons. The resulting reaction mixture primarily contains a mixture of native and monoPEGylated protein. The monoPEGylated species are purified by column chromatography to remove free interferon-α and higher molecular weight species. Confirmation of N-terminal PEGylation is conducted by peptide mapping. Increasing the ratio of PEG to protein increases the degree of PEGylation yielding polyPEGylated IFN-α.

Example 14

N-terminal PEGylation of Human Growth Hormone

Recombinant human growth hormone, "hGH" (produced in *E. coli*, mammalian cells such as Chinese hamster ovary cells, or another source) is coupled to mPEG2(40K Da)-ketone (prepared as described in Example 7).

hGH (~2 mg) is dissolved in 1 ml of 0.1 mM sodium acetate (pH 5) and mPEG$_2$(40K Da)-ketone is added at 5× the molar hGH concentration. A 5 to 20-fold molar excess of the reducing agent, NaCNBH$_3$, is added and the solution is stirred for 24 hours at 4° C. to couple the mPEG$_2$(40K)-ketone reagent to the protein via an amine linkage.

Progress of the reaction is analyzed by SDS-PAGE or MALDI-TOF mass spectrometry to determine the degree of PEGylation. Confirmation of the degree of PEGylation, 1-mer, 2-mers, and so forth, is carried out by Matrix Assisted Laser Desorption Ionization Time-of-Flight (MALDI-TOF) mass spectrometry. The displayed peaks for native and monoPEGylated and other species differ by approximately 40,000 Daltons. The resulting reaction mixture primarily contains a mixture of native and monoPEGylated protein. The monoPEGylated species are purified by column chromatography to remove free hGH and higher molecular weight species. Confirmation of N-terminal PEGylation is conducted by peptide mapping. Increasing the ratio of mPEG$_2$(40K)-ketone to protein increases the degree of PEGylation yielding a population of polyPEGylated hGH.

Example 15

N-terminal PEGylation of Interferon-β

Recombinant interferon-β, "IFN-β" (produced in *E. coli*, mammalian cells such as Chinese hamster ovary cells, or another source) is coupled to mPEG2(40K Da)-ketone (prepared as described in Example 7).

IFN-β (~2 mg) is dissolved in 1 ml of 0.1 mM sodium acetate (pH 5) and mPEG2(40K Da)-ketone is added at 5× the molar IFN-β concentration. A 5 to 20-fold molar excess of the reducing agent, NaCNBH$_3$, is added and the solution is stirred for 24 hours at 4° C. to couple the mPEG$_2$(40K Da)-ketone reagent to the protein via an amine linkage.

Progress of the reaction is analyzed by SDS-PAGE or MALDI-TOF mass spectrometry to determine the degree of PEGylation. Confirmation of the degree of PEGylation, 1-mer, 2-mers, and so forth, is carried out by Matrix Assisted Laser Desorption Ionization Time-of-Flight (MALDI-TOF) mass spectrometry. The displayed peaks for native and mono-PEGylated and other species differ by approximately 40,000 Daltons. The resulting reaction mixture primarily contains a mixture of native and monoPEGylated protein. The monoPEGylated species are purified by column chromatography to remove free IFN-β and higher molecular weight species. Confirmation of N-terminal PEGylation is conducted by peptide mapping. Increasing the ratio of mPEG2(40K Da)-ketone to protein increases the degree of PEGylation yielding a population of polyPEGylated IFN-β.

Example 16

N-terminal PEGylation of FSH

Recombinant follicle stimulating hormone, "FSH" (produced in *E. coli*, mammalian cells such as Chinese hamster ovary cells, or another source) is coupled to mPEG2(40K Da)-ketone (prepared as described in Example 7).

FSH (~2 mg) is dissolved in 1 mL of 0.1 mM sodium acetate (pH 5) and mPEG2(40K Da)-ketone is added at 5× the molar FSH concentration. A 5 to 20-fold molar excess of the reducing agent, NaCNBH$_3$, is added and the solution is stirred for 24 hour at 4° C. to couple the mPEG$_2$(40K Da)-ketone reagent to the protein via an amine linkage.

Progress of the reaction is analyzed by SDS-PAGE or MALDI-TOF mass spectrometry to determine the degree of PEGylation. Confirmation of the degree of PEGylation, 1-mer, 2-mers, and so forth, is carried out by Matrix Assisted Laser Desorption Ionization Time-of-Flight (MALDI-TOF) mass spectrometry. The displayed peaks for native and mono-PEGylated and other species differ by approximately 40,000 Daltons. The resulting reaction mixture primarily contains a mixture of native and monoPEGylated protein. The monoPEGylated species are purified by column chromatography to remove free FSH and higher molecular weight species. Confirmation of N-terminal PEGylation is conducted by peptide mapping. Increasing the ratio of mPEG2(40K Da)-ketone to protein increases the degree of PEGylation yielding a population of polyPEGylated FSH.

Example 17

N-terminal PEGylation of hGH

Recombinant human growth hGH (produced in *E. coli*, mammalian cells such as Chinese hamster ovary cells, or another source) is coupled to PEG (5K Da)-diethyl ketal (prepared as described in Example 9).

hGH (~2 mg) is dissolved in 1 mL of 0.1 mM sodium acetate (pH 5) and PEG (5K Da)-diethyl ketal is added at 5× the molar hGH concentration. A 5 to 20-fold molar excess of the reducing agent, NaCNBH$_3$, is added and the solution is stirred for 24 hours at 4° C. to couple the PEG (5K Da)-diethyl ketal reagent to the protein via an amine linkage.

Progress of the reaction is analyzed by SDS-PAGE or MALDI-TOF mass spectrometry to determine the extent of PEGylation. Confirmation of the degree of PEGylation, 1-mer, 2-mers, and so forth, is carried out by Matrix Assisted Laser Desorption Ionization Time-of-Flight (MALDI-TOF) mass spectrometry. The displayed peaks for native and monoPEGylated and other species differ by approximately 5,000 Daltons. The resulting reaction mixture, primarily contains a mixture of native and monoPEGylated protein, in particular due to the PEG (5K)-diethyl ketal reagent. The monoPEGylated species are purified by column chromatography to remove free hGH and higher molecular weight species. Confirmation of N-terminal PEGylation is conducted by peptide mapping.

Example 18

PEGylation of Amphotericin B

The amino group of a small molecule, amphotericin B, is modified by attachment of a mPEG (2K Da)-methyl ketone.

To a solution of amphotericin B HCl in deionized water is added a 2-fold molar excess of mPEG (2K Da)-methyl ketone (Example 1) dissolved in 0.1 M phosphate buffer at pH 6.5. To this mixture is added a solution of NaCNBH$_3$ (at a 1.5 to 10-fold molar excess) in phosphate buffer at pH 6.5, and the resulting solution is stirred at room temperature overnight under an argon atmosphere. Aliquots of the reaction mixture are withdrawn at various time intervals to monitor the progress of the reaction by $^1$H NMR. Upon completion, the reaction mixture is further diluted by addition of water, and NaCl is added to achieve saturation. The product is then extracted with dichloromethane, and the combined organic extracts are dried over anhydrous sodium sulfate, filtered to remove drying agent, and the solvent evaporated by rotary evaporation. The product is then precipitated by addition of diethyl ether, and dried under vacuum overnight. The recovered product is analyzed by gel permeation chromatography to determine the extent of conjugation.

The crude product is purified by cation exchange chromatography using Poros 50 HS cation exchange resin (PerSeptive BioSystems, Framingham, Mass.). Following washing of the column with deionized water, the product is eluted with 1N NaCl solution. The conjugate containing extracts are combined, and the product is extracted with dichloromethane. The organic solution is dried over anhydrous sodium sulfate, filtered, and the solvent evaporated by rotary evaporation. The purified conjugate is purified by the addition of diethyl ether.

If necessary, the product is further purified by reverse phase HPLC chromatography using a Betasil C18 column (Keystone Scientific).

What is claimed is:
1. A conjugate, wherein the conjugate has the structure

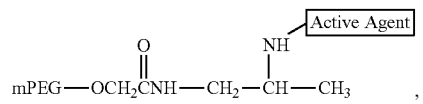

wherein mPEG is a methoxy capped poly(ethylene glycol) having a nominal average molecular weight of from about 2,500 Daltons to about 100,000 Daltons and

is an amine-containing active agent.

2. The conjugate of claim 1, wherein the mPEG has a nominal average molecular weight of from about 4,900 Daltons to about 40,000 Daltons.

3. The conjugate of claim 2, wherein the mPEG has a nominal average molecular weight of from about 9,900 Daltons to about 25,000 Daltons.

4. The conjugate of claim 1, wherein the mPEG has a nominal average molecular weight of about 5,000 Daltons.

5. The conjugate of claim 1, wherein the active agent is selected from erythropoietin, granulocyte macrophage colony stimulating factor (GMCSF), granulocyte colony stimulating factor (GCSF), interferon alpha, interferon beta, human growth hormone, amphotericin B, and follicle stimulating hormone.

6. The conjugate of claim 1, wherein the active agent is a polypeptide.

7. A pharmaceutical preparation comprising the conjugate of claim 1 and a pharmaceutically acceptable excipient.

* * * * *